United States Patent
Biagini et al.

(10) Patent No.: US 10,799,494 B2
(45) Date of Patent: Oct. 13, 2020

(54) COMBINATION OF RESPIRATORY ELECTRON TRANSPORT CHAIN INHIBITORS WITH A CYTOCHROME BD INHIBITOR

(71) Applicant: Liverpool School of Tropical Medicine, Liverpool (GB)

(72) Inventors: Giancarlo A. Biagini, Liverpool (GB); Stephen A. Ward, Liverpool (GB); Gemma L. Nixon, Liverpool (GB); Paul M. O'Neill, Liverpool (GB)

(*) Notice: Subject to any disclaimer, the term of this patent is extended or adjusted under 35 U.S.C. 154(b) by 0 days.

(21) Appl. No.: 16/062,443

(22) PCT Filed: Dec. 16, 2016

(86) PCT No.: PCT/GB2016/053972
§ 371 (c)(1),
(2) Date: Jun. 14, 2018

(87) PCT Pub. No.: WO2017/103615
PCT Pub. Date: Jun. 22, 2017

(65) Prior Publication Data
US 2019/0151305 A1    May 23, 2019

(30) Foreign Application Priority Data
Dec. 16, 2015  (GB) .................. 1522232.6

(51) Int. Cl.
*A61K 31/4709* (2006.01)
*A61K 31/47* (2006.01)
*A61P 31/06* (2006.01)
*A61K 31/437* (2006.01)
*A61K 31/4409* (2006.01)
*A61K 31/4439* (2006.01)
*A61K 31/5377* (2006.01)

(52) U.S. Cl.
CPC ........ *A61K 31/4709* (2013.01); *A61K 31/437* (2013.01); *A61K 31/4409* (2013.01); *A61K 31/4439* (2013.01); *A61K 31/47* (2013.01); *A61K 31/5377* (2013.01); *A61P 31/06* (2018.01)

(58) Field of Classification Search
CPC ................ A61K 2300/00; A61K 31/47; A61K 31/4709; A61K 31/437; A61K 31/4409; A61K 31/4439; A61K 31/5377; A61P 31/06
See application file for complete search history.

(56) References Cited

FOREIGN PATENT DOCUMENTS

WO    2012/069856 A1    5/2012

OTHER PUBLICATIONS

Weinstein EA, et al. (2005) Inhibitors of type II NADH:menaquinone oxidoreductase represent a class of antitubercular drugs. Proc Natl Acad Sci U S A 102(12):4548-4553.

(Continued)

*Primary Examiner* — Savitha M Rao

(57) ABSTRACT

The present invention relates to a combination therapeutic product comprising one or more respiratory electron transport chain inhibitors and a cytochrome bd inhibitor, as defined herein, or a pharmaceutically acceptable salt thereof. The present invention also relates to pharmaceutical compositions comprising the combination therapeutic product and to the use of the combination therapeutic product in the treatment of mycobacterial infections, such as tuberculosis.

12 Claims, 10 Drawing Sheets
Specification includes a Sequence Listing.

(56) References Cited

OTHER PUBLICATIONS

Figure 6:
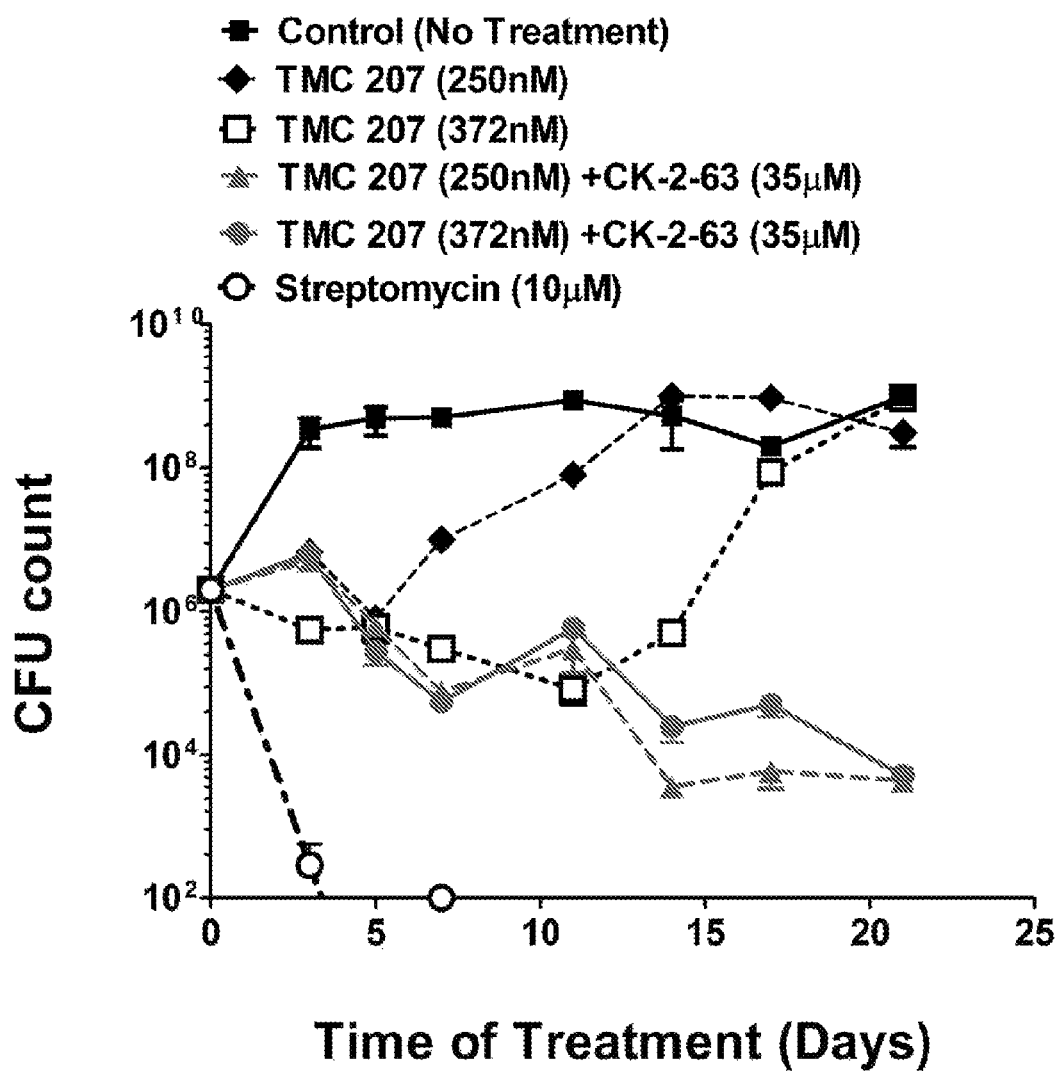

Koul A, et al. (2007) Diarylquinolines target subunit c of mycobacterial ATP synthase. Nat Chem Biol 3(6):323-324.
Koul A, et al. (2008) Diarylquinolines are bactericidal for dormant mycobacteria as a result of disturbed ATP homeostasis. J Biol Chem 283(37):25273-25280.
Rao SP, Alonso S, Rand L, Dick T, & Pethe K (2008) The protonmotive force is required for maintaining ATP homeostasis and viability of hypoxic, nonreplicating Mycobacterium tuberculosis. Proc Natl Acad Sci U S A 105(33):11945-11950.
Diacon AH, et al. (2009) the diarylquinoline TMC207 for multidrug-resistant tuberculosis. N Engl J Med 360(23):2397-2405.
Warman AJ, et al. (2013) Antitubercular pharmacodynamics of phenothiazines. J Antimicrob Chemother 68(4):869-880.
Wu Y (2002) How might qinghaosu (artemisinin) and related compounds kill the intraerythrocytic malaria parasite? A chemist's view. Accounts of chemical research 35(5):255-259.
Fisher N, Warman AJ, Ward SA, & Biagini GA (2009) Chapter 17 Type II NADH: quinone oxidoreductases of Plasmodium falciparum and Mycobacterium tuberculosis kinetic and high-throughput assays. Methods in enzymology 456:303-320.
Fisher N, et al. (2012) Cytochrome b mutation Y268S conferring atovaquone resistance phenotype in malaria parasite results in reduced parasite bc1 catalytic turnover and protein expression. J. Biol. Chem. 287(13):9731-9741.
Matsumoto Y, et al. (2006) Kinetic mechanism of quinol oxidation by cytochrome bd studied with ubiquinone-2 analogs. Journal of Biochemistry 139(4):779-788.
Biagini GA, et al. (2008) Acridinediones: selective and potent inhibitors of the malaria parasite mitochondrial bc1 complex. Molecular pharmacology 73(5):1347-1355.
Kuboyama M, Yong FC, & King TE (1972) Studies on cytochrome oxidase. J. Biol. Chem. 247(20):6375-6383.
Sirturo datasheet and safety information , https://www.sirturo.com/.
Hartkoorn RC, Chandler B, Owen A, et al. Differential drug susceptibility of intracellular and extracellular tuberculosis, and the impact of P-glycoprotein, Tuberculosis, 2007; 87(3): 248-55.
Berenbaum MC. A method for testing for synergy with any number of agents. The Journal of Infectious Diseases, 1978; 137(2): 122-30.
Rybniker, J. et al. (2015) Lansoprazole is an antituberculous prodrug targeting cytochrome bc1. Nature communications 6, 7659, doi:10.1038/ncomms8659.
PCT International Search Report and Written Opinion for PCT/GB2016/053972, completed on Apr. 3, 2017, 20 pages.
Ping Lu et al: "The cytochrome bd-type quinol oxidase is important for survival of Mycobacterium smegmatis under peroxide and antibiotic-induced stress", Scientific Reports, vol. 5, May 27, 2015 (May 27, 2015), p. 10333, XP055350705, SOI: 10.1038/srep10333, abstract, p. 5, paragraph 2-p. 6, paragraph 2, p. 6; figure 6, p. 6, paragraph 4, p. 7, paragraph 2-4.
M. Berney et al: "A Mycobacterium tuberculosis Cytochrome bd Oxidase Mutant is Hypersensitive to Bedaquiline", MBIO, vol. 5, No. 4, Jul. 15, 2014 (Jul. 15, 2014), pp. e01275-14, XP055350689, US, ISSN: 2150-7511, DOI: 10.1128/mBio.01275-14, abstract, p. 2, left-hand column, last line-right-hand column, line 8, p. 2; figure 1.
K. Arora et al: "Respiratory Flexibility in Response to Inhibition of Cytochrome c Oxidase in Mycobacterium tuberculosis", Antimicrobial Agents and Chemotherpay, vol. 58, No. 11, Aug. 25, 2014 (Aug. 25, 2014), pp. 6962-6965, XP055351336, ISSN: 0066-4804, DOI: 10.1128/AAC.03486-14, abstract, p. 6962; table 1.
Borisov V B et al: "Cytochromebdprotects bacteria against oxidative and nitrosative stress: A potential target for next-generation antimicrobial agents", Biochemistry, Maik Nauka—Interperiodica, RU, vol. 80, No. 5, May 10, 2015 (May 10, 2015), pp. 565-575, XP035500464, ISSN: 0006-2979, DOI: 10.1134/S0006297915050077, abstract, p. 571, left-hand column, line 8-right-hand column, paragraph 3.
Garrett C. Moraski et al: "Putting Tuberculosis (TB) to Rest: Transformation of the Sleep Aid, Ambien, and "Anagrams" Generated Potent Antituberculosis Agents", ACS Infectious Diseases, vol. 1, No. 2, Feb. 13, 2015 (Feb. 13, 2015), pp. 85-90, XP055292694, ISSN: 2373-8227, DOI: 10.1021/id500008t, abstract, p. 88, last paragraph.
Taghreed Abdulaziz et al: "Molecular, biochemical and pharmacological tuberculosis cytochrome bd-I oxidase: a putative therapeutic target", Jan. 1, 2013 (Jan. 1, 2013), XP055350739, Retrieved from the Internet: URL: http://repository.liv.ac.uk/12633/2/HafizTaghreed_Jun3e2013_12633.pdf, p. 122; table 3.4, p. 125; table 3.5.
Narisa Phummarin et al: "SAR and identification of 2-(quinolin-4-yloxy)acetamides as Mycobacterium tuberculosis cytochrome bc 1 inhibitors", MEDCHEMCOMM, vol. 7, No. 11, Jan. 1, 2016 (Jan. 1, 2016), pp. 2122-2127, XP055351502, United Kingdom, ISSN: 2040-2503, DOI: 10.1039/C6MD00236F, p. 2123; compounds, p. 2124; table 1, p. 2125, right-hand column.
Haagsma AC, et al. (2009) Selectivity of TMC207 towards mycobacterial ATP synthase compared with that towards the eukaryotic homologue. Antimicrob Agents Chemother 53(3):1290-1292.
Vitaliy B. Borisov, Robert B Gennis, James Hemp, Michael I. Verkhovsky (2011), The cytochrome bd respiratory oxygen reductases, Biochimica et Biophysica Acta (BBA)—Bioenergetics, 1807(11):1398-1413.
Miroux B & Walker JE (1996) Over-production of proteins in Escherichia coli: Mutant hosts that allow synthesis of some membrane proteins and globular proteins at high levels. Journal of Molecular Biology 260(3):289-298.
Taghreed Hafiz, Abstract Only, "Molecular, biochemical and pharmacological characterisation of Mycobacterium tuberculosis cytochrome bd-I oxidase: a putative therapeutic target" published Feb. 18, 2014, University of Liverpool Repository, Liverpool, United Kingdom.
Taghreed Hafiz, "Molecular, biochemical and pharmacological characterisation of Mycobacterium tuberculosis cytochrome bd-I oxidase: a putative therapeutic target" Thesis, published Jan. 27, 2016, University of Liverpool Repository, Liverpool, United Kingdom.

(a)

(b)

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: PCR Fw primer

<400> SEQUENCE: 1
ccggagatga cagatgaatg tcgtcg          26

<210> SEQ ID NO 2
<211> LENGTH: 30
<212> TYPE: DNA
<213> ORGANISM: Artificial Sequence
<220> FEATURE:
<223> OTHER INFORMATION: PCR Rv primer

<400> SEQUENCE: 2
ggcgttacgt gctgatatcg atgactcagg          30

COMBINATION OF RESPIRATORY ELECTRON TRANSPORT CHAIN INHIBITORS WITH A CYTOCHROME BD INHIBITOR

CROSS-REFERENCE TO RELATED APPLICATIONS

This application is a national stage entry made under 35U.S.C. § 371(b) of PCT International Application No. PCT/GB2016/053972, filed Dec. 16, 2016, which is based on and claims priority from Great Britain Patent Application No. GB1522232.6, filed Dec. 16, 2015, the disclosures of which are incorporated by reference herein in their entirety.

INTRODUCTION

The present invention relates to a combination therapeutic product suitable for use in the treatment of mycobacterial infections, such as tuberculosis.

BACKGROUND OF THE INVENTION

The WHO recommended first-line treatment for tuberculosis (TB) relies on drugs developed some 40 years ago. There are a number of shortcomings with these drugs including (i) long treatment regimens (6 to 9 months) leading to patient non-compliance, (ii) adverse drug-drug interactions with anti-HIV drugs (HIV/AIDS is a common co-infection) and (iii) limited or no activity against multi-drug resistant (MDR) and extensively drug resistant (XDR) *Mycobacterium tuberculosis* (Mtb).

Targeting the Mtb respiratory electron transport chain (ETC) has been shown, to be effective in sterilizing both replicating and dormant Mtb and has led to the recent clinical development and registration of the antitubercular drug bedaquiline (TMC207) for use against MDR TB (1-7). Current inhibitors work by selectiviely targeting single respiratory electron transport chain components. Examples, include bedaquiline targeting the ATPsynthase(2), phenothiazines targeting ndh/ndhA (7) and various inhibitors e.g. imidazopyridines (8), targeting cytochrome bcc (also refered in some publications as $bc_1$). These known inhibitors typically suffer from poor efficacy, with high doses of inhibitor needed in order to be effective at reducing Mtb growth. This low efficacy has limited the clinical utility of these inhibitors because the high dosages required can be associated with adverse effects.

For example, in one placebo-controlled trial, an increased risk of death was observed with bedaquiline (also known as SIRTURO) treatment (9/79, 11.4%) compared to the placebo treatment group (2/81, 2.5%) (16). This may be linked with the observed QT prolongation that can occur with bedaquiline especially during the initial (loading) treatment phase (400 mg once daily for 2 weeks followed by 200 mg 3 times per week for 22 weeks with food). Effective treatment at a lower dose of bedaquiline would therefore be very advantageous and may mitigate many of the safety concerns.

Accordingly, there remains a need for new and effective treatments for mycobacterial infections, such as tuberculosis.

The present invention was devised with the foregoing in mind.

SUMMARY OF THE INVENTION

In one aspect, the present invention relates to a combination therapeutic product which comprises one or more respiratory electron transport chain inhibitors as defined herein, or a pharmaceutically acceptable salt thereof, and a cytochrome bd inhibitor as defined herein, or a pharmaceutically acceptable salt thereof.

In another aspect, the present invention relates to a combination therapeutic product comprising one or more respiratory electron transport chain inhibitors as defined herein, or a pharmaceutically acceptable salt thereof, and a cytochrome bd inhibitor as defined herein, or a pharmaceutically acceptable salt thereof, for use simultaneously, sequentially or separately in the treatment of a mycobacterial infection.

In another aspect, the present invention relates to a pharmaceutical composition suitable for use in the treatment of a mycobacterial infection which comprises a combination therapeutic product as defined herein, in association with a pharmaceutically-acceptable excipient or carrier.

In another aspect, the present invention relates to the use of a combination therapeutic product as defined herein, or a pharmaceutical composition as defined herein, for the manufacture of a medicament for administration simultaneously, sequentially or separately to a patient in need thereof, such as a human, for the treatment or prophylaxis of a mycobacterial infection.

In another aspect, the present invention relates to a method for the treatment or prophylaxis of a mycobacterial infection comprising simultaneously, sequentially or separately administering an effective amount of a combination therapeutic product, as defined herein, or a pharmaceutical composition, as defined herein, to a patient, such as a human, in need of such treatment.

In another aspect, the present invention relates to a cytochrome bd inhibitor, as defined herein, for use in the treatment of a mycobacterial infection, wherein the cytochrome bd inhibitor is administered in combination with one or more respiratory electron transport chain inhibitors as defined herein.

In another aspect, the present invention relates to the use of a cytochrome bd inhibitor as defined herein, in the manufacture of a medicament for use in the treatment of a mycobacterial infection, wherein the cytochrome bd inhibitor is administered in combination with one or more respiratory electron transport chain inhibitors as defined herein.

In another aspect, the present invention relates to a method for the treatment or prophylaxis of a mycobacterial infection comprising simultaneously, sequentially or separately administering an effective amount of a cytochrome bd inhibitor as defined herein, in combination with one or more respiratory electron transport chain inhibitors as defined herein.

DETAILED DESCRIPTION OF THE INVENTION

Definitions

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl.

The term "(m-nC)" or "(m-nC) group" used alone or as a prefix, refers to any group having m to n carbon atoms.

Unless otherwise specified, the term "alkoxy" as used herein include reference to —O— alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Unless otherwise specified, the term "aryl" as used herein includes reference to an aromatic ring system comprising 6, 7, 8, 9 or 10 ring carbon atoms. Aryl is often phenyl but may be a polycyclic ring system, having two or more rings, at least one of which is aromatic. This term includes reference to groups such as phenyl, naphthyl and the like.

Unless otherwise specified, the term "halogen" or "halo" as used herein includes reference to F, Cl, Br or I. In a particular, halogen may be F or Cl, of which Cl is more common.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo -1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Unless otherwise specified, the term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or unsubstituted.

It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it will of course be understood that the substituents described herein may themselves be substituted by any substituent, subject to the aforementioned restriction to appropriate substitutions as recognised by the skilled person.

Unless otherwise specified, the term "optionally substituted" refers to either groups, structures, or molecules that are substituted and those that are not substituted. The term "wherein a/any CH, $CH_2$, $CH_3$ group or heteroatom (i.e. NH) within a $R^1$ group is optionally substituted" suitably means that (any) one of the hydrogen radicals of the $R^1$ group is substituted by a relevant stipulated group.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Combination Therapeutic Products of the Present Invention

It will be appreciated by a person skilled in the art that the term "combination therapeutic product" refers to the net combined product resulting from the administration one or more components either simultaneously, sequentially or separately, in order to induce a therapeutic effect.

Furthermore, it will be appreciated that in administering the one or more components either simultaneously, sequentially or separately, the therapeutic product affords a superior therapeutic effect to that achieved upon administration of one of the components of the combination therapeutic product alone, and at its conventional dose. The superior therapeutic effect may be measured by, for example, the extent of the response, the response rate, the time to disease progression or the survival period, to that achievable on dosing one of the components of the combination therapeutic product alone, and at its conventional dose.

For example, the effect of the combination therapeutic product is beneficial if the effect is therapeutically superior to the effect achievable with the respiratory electron transport chain inhibitor alone or with the cytochrome bd inhibitor alone. Further, the effect of the combination therapeutic product is defined as affording a beneficial effect if one of the components is dosed at its conventional dose (or lower) and the other component is dosed at a reduced dose and the therapeutic effect, as measured by, for example, the extent of the response, the response rate, the time to disease progression or the survival period, is equivalent (or higher) to that achievable on dosing conventional amounts of the components of the combination therapeutic product alone.

It should also be appreciated that according to the present invention a combination therapeutic product is defined as affording a synergistic effect if the effect is therapeutically superior, as measured by, for example, the extent of the response, the response rate, the time to disease progression or the survival period, to that expected to be achievable on dosing both of the components of the combination therapeutic product together at their conventional dose (for example the combination effect is greater than the sum of the single agent effects). Suitably, the combination product of the present invention does provide a synergistic effect.

According to one aspect of the present invention, there is provided a combination therapeutic product comprising one or more respiratory electron transport chain inhibitors and a cytochrome bd inhibitor, or a pharmaceutically acceptable salt thereof. The combination therapeutic product may comprise between 1 and 3 respiratory electron transport chain inhibitors. Most suitably, the combination therapeutic product comprises one respiratory electron transport chain inhibitor.

According to another aspect of the present invention, there is provided a combination therapeutic product comprising one or more respiratory electron transport chain inhibitors and a cytochrome bd inhibitor for use simultaneously, sequentially or separately in the treatment of a mycobacterial infection. The combination therapeutic product may comprise between 1 and 3 respiratory electron transport chain inhibitors. Most suitably, the combination therapeutic product comprises one respiratory electron transport chain inhibitor.

According to a further aspect of the present invention there is provided a cytochrome bd inhibitor for use in the treatment of a mycobacterial infection, administered in combination with one or more respiratory electron transport chain inhibitors. The cytochrome bd inhibitor may be administered in combination with between 1 and 3 respiratory electron transport chain inhibitors. Most suitably, the cytochrome bd inhibitor is administered in combination with one respiratory electron transport chain inhibitor.

It will be appreciated that the combination therapeutic product of the present invention, or indeed the cytochrome bd inhibitor administered in combination with one or more respiratory electron transport chain inhibitors, may be used to treat any suitable mycobacterial infection. Suitably, the mycobacterial infection is selected from Buruli Ulcers, leprosy, Hansen's disease or tuberculosis. More suitably, the mycobacterial infection is selected from leprosy or tuberculosis. Yet more suitably, the mycobacterial infection is tuberculosis. Most suitable, the mycobacterial infection is multidrug resistant tuberculosis.

Cytochrome bd Inhibitors

Cytochrome bd is a respiratory quinol: $O_2$ oxidoreductase found in many prokaryotes, including a number of pathogens. The main bioenergetic function of the enzyme is the production of a proton motive force by the vectorial charge transfer of protons. (9) Suitably, the cytochrome bd inhibitors of the present invention may be any compound, or pharmaceutically acceptable salt thereof, capable of inhibiting any cytochrome bd respiratory oxygen reductase. However more suitably, the cytochrome bd inhibitors of the present invention may be any compound capable of inhibiting mycobacterial cytochrome bd.

In an embodiment of the present invention, the cytochrome bd inhibitor is a quinolone compound or an analogue thereof.

In another embodiment of the present invention, the cytochrome bd inhibitor is a compound of formula I or formula II, shown below:

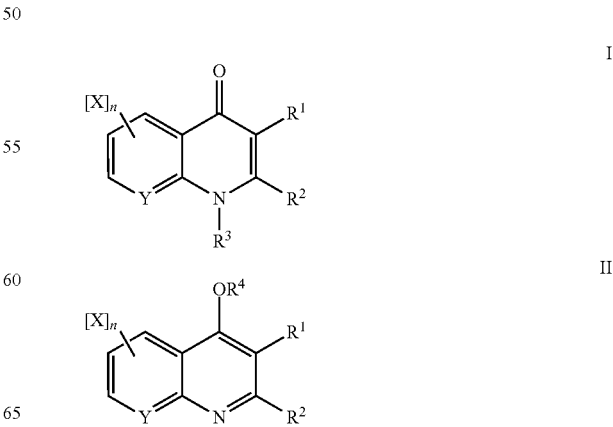

wherein:
    Y is N or CH;
    n is 0, 1 or 2;
    X is selected from fluoro, chloro, trifluoromethyl, trifluoromethoxy, cyano, hydroxy, methoxy, heterocyclyl, a prodrug moiety, or a combination thereof (e.g. where n=2);
    $R^1$ is selected from hydrogen, methyl, ethyl, hydroxyl, $CH_2OH$, halo (e.g. chloro, bromo), or $R^1$ is a group of the formula:

-$L^1$-$Q^1$ wherein:
    $L^1$ is absent or selected from —O—, —C($R^{10}R^{11}$)—O—, —S—, —SO—, —$SO_2$—, —N($R^{10}$)—, —C(O)—, —CH(O$R^{10}$)—, —C(O)N($R^{10}$)—, —N($R^{10}$)C(O)—, —C(O)O—, —OC(O)—, —N($R^{10}$)C(O)N($R^{11}$)—, —S(O)$_2$N($R^{10}$)—, or —N($R^{10}$)$SO_2$—, wherein $R^{10}$ and $R^{11}$ are each independently selected from hydrogen or (1-4C)alkyl;
    $Q^1$ is selected from hydrogen, (1-6C)alkyl, aryl, heterocyclyl or heteroaryl, each of which is optionally substituted with one or more substituents independently selected from halo, cyano, nitro, hydroxy, amino, trifluoromethyl, trifluoromethoxy, (1-4C)alkyl or (1-4C)alkoxy; or
    $Q^1$ is optionally substituted with a group of the formula:

—$W^1$—$Z^1$ wherein:
    $W^1$ is absent or selected from —O—, —S—, —N($R^{14}$)— or —C(O)—, wherein $R^{14}$ is selected from hydrogen or (1-4C)alkyl;
    $Z^1$ is selected from (1-6C)alkyl, (3-6C)cycloalkyl, aryl, heteroaryl or (3-6C)heterocycyl, wherein $Z^1$ is optionally substituted with one or more substituents selected from halo, cyano, nitro, hydroxy, amino, trifluoromethyl, trifluoromethoxy, (1-4C)alkyl or (1-4C)alkoxy;
    or $L^1$ is —O— or —C($R^{10}R^{11}$)—O— and $Q^1$ is a prodrug moiety;
    $R^2$ is a group

-$L^2$-$Q^3$-$L^3$-$Q^2$ wherein:
    $L^2$ is absent or (1-3C)alkylene optionally substituted with (1-2C)alkyl or oxo;
    $Q^3$ is absent or selected from aryl, heterocyclyl or heteroaryl, wherein $Q^3$ is optionally substituted by one or more substituents selected from halo, cyano, nitro, hydroxy, amino, trifluoromethyl, trifluoromethoxy, (1-4C)alkyl or (1-4C)alkoxy;
    $L^3$ is selected from a direct bond, —(C$R^{12}R^{13}$)$_q$—, —O—, —S—, —SO—, —$SO_2$—, —N($R^{12}$)—, —C(O)—, —CH(O$R^{12}$)—, —C(O)N($R^{12}$)—, —N($R^{12}$)C(O)—, —C(O)O—, —OC(O)—, —N($R^{12}$)C(O)N($R^{13}$)—, —S(O)$_2$N($R^{12}$)—, or —N($R^{12}$)$SO_2$—, wherein $R^{12}$ and $R^{13}$ are each independently selected from hydrogen or (1-4C)alkyl and q is an integer selected from 1 or 2;
    $Q^2$ is selected from (1-6C)alkyl, aryl, heterocyclyl, heteroaryl or cycloalky, each of which is optionally substituted with one or more substituents independently selected from halo, cyano, nitro, hydroxy, carboxy, carboxy ester (e.g. methyl or ethyl ester), amino, trifluoromethyl, trifluoromethoxy, (1-4C)alkyl or O$R^{15}$, wherein $R^{15}$ is selected from (1-4C)alkyl or aryl, and wherein any carbon atom of the substituent(s) of $Q^2$ may be further optionally substituted with one or more substituents independently selected from halo, cyano, nitro, hydroxyl, carboxy, carboxy ester, amino, trifluoromethyl, trifluoromethoxy, heterocyclyl, aryl, heteroaryl or N$R^{16}R^{17}$, wherein $R^{16}$ and $R^{17}$ are independently selected from H, (1-4C)alkyl, aryl, aryl(1-2C)alkyl or C(O)O(1-4C)alkyl;
    $R^3$ is selected from hydrogen, hydroxy, (1-6C)alkyl, aryl or aryl-(1-2C)alkyl;
    $R^4$ is selected from hydrogen, (1-4C)alkyl or a prodrug moiety;
    or a pharmaceutically acceptable salt thereof Particular cytochrome bd inhibitors of the invention include, for example, compounds of the formula (I) or (II), or pharmaceutically acceptable salts and/or solvates thereof, wherein, unless otherwise stated, each of $R^1$, $R^2$, $R^3$, $R^4$, X, Y, n and any associated substituent group has any of the meanings defined hereinbefore or in any of paragraphs (1) to (20) hereinafter:
    (1) Y is CH;
    (2) X is selected from fluoro, chloro, trifluoromethyl, trifluoromethoxy, cyano, hydroxy, methoxy or heterocyclyl;
    (3) X is selected from fluoro, chloro, trifluoromethyl, trifluoromethoxy or methoxy;
    (4) X is selected from fluoro, chloro or methoxy;
    (5) X is selected from fluoro or methoxy;
    (6) $R^1$ is selected from hydrogen, methyl, ethyl, hydroxyl, $CH_2OH$, halo, or $R^1$ is a group of the formula:

-$L^1$-$Q^1$ wherein:
    $L^1$ is absent or selected from —O—, —S—, —SO—, —$SO_2$—, —N($R^{10}$)—, —C(O)—, —C(O)N($R^{10}$)—, —N($R^{10}$)C(O)—, —C(O)O—, —OC(O)—, —S(O)$_2$N($R^{10}$)—, or —N($R^{10}$)$SO_2$—, wherein $R^{10}$ is selected from hydrogen or (1-4C)alkyl;
    $Q^1$ is selected from hydrogen, (1-6C)alkyl, aryl, heterocyclyl or heteroaryl, each of which is optionally substituted with one or more substituents independently selected from halo, cyano, nitro, hydroxy, amino, trifluoromethyl, trifluoromethoxy, (1-4C)alkyl or (1-4C)alkoxy; or
    $Q^1$ is optionally substituted with a group of the formula:

—$W^1$-$Z^1$ wherein:
    $W^1$ is absent or selected from —O—, —S— or —N($R^{14}$)— wherein $R^{14}$ is selected from hydrogen or (1-4C)alkyl;
    $Z^1$ is selected from (1-6C)alkyl, (3-6C)cycloalkyl, aryl, heteroaryl or (3-6C)heterocycyl, wherein $Z^1$ is optionally substituted with one or more substituents selected from halo, hydroxy, amino, trifluoromethyl, trifluoromethoxy, (1-4C)alkyl or (1-4C)alkoxy;
    (7) $R^1$ is selected from hydrogen, methyl, ethyl, hydroxyl, $CH_2OH$, halo, or $R^1$ is a group of the formula:

-$L^1$-$Q^1$ wherein:
    $L^1$ is absent or selected from —O—, —S—, —N($R^{10}$)—, —C(O)—, —C(O)N($R^{10}$)—, —N($R^{10}$)C(O)—, —C(O)O— or —OC(O)—, wherein $R^{10}$ is selected from hydrogen or (1-4C)alkyl;
    $Q^1$ is selected from hydrogen, (1-6C)alkyl, aryl, heterocyclyl or heteroaryl, each of which is optionally substituted with one or more substituents independently selected from halo, hydroxy, amino, trifluoromethyl, trifluoromethoxy, (1-4C)alkyl or (1-4C)alkoxy; or
    $Q^1$ is optionally substituted with a group of the formula:

—$W^1$—$Z^1$ wherein:
  $W^1$ is absent or selected from —O— or —N($R^{14}$)— wherein $R^{14}$ is selected from hydrogen or (1-2C) alkyl;
  $Z^1$ is selected from (1-6C)alkyl, aryl or heteroaryl, wherein $Z^1$ is optionally substituted with one or more substituents selected from halo, hydroxy, amino, trifluoromethyl, trifluoromethoxy, (1-4C)alkyl or (1-4C)alkoxy;

(8) $R^1$ is selected from hydrogen, methyl, ethyl, hydroxyl, $CH_2OH$, halo, or $R^1$ is a group of the formula:

-$L^1$-$Q^1$ wherein:
  $L^1$ is absent or selected from —C(O)N($R^{10}$)—, —N($R^{10}$)C(O)—, —C(O)O— or —OC(O)—, wherein $R^{10}$ is selected from hydrogen or (1-4C)alkyl;
  $Q^1$ is selected from hydrogen, (1-6C)alkyl, aryl, heterocyclyl or heteroaryl, each of which is optionally substituted with one or more substituents independently selected from halo, hydroxy, amino, trifluoromethyl, trifluoromethoxy, (1-4C)alkyl or (1-4C)alkoxy; or
  $Q^1$ is optionally substituted with a group of the formula:
  wherein:
    $W^1$ is absent or —O—;
    $Z^1$ is selected from (1-4C)alkyl, aryl or heteroaryl, wherein $Z^1$ is optionally substituted with one or more substituents selected from halo, hydroxy, amino, trifluoromethyl, trifluoromethoxy, (1-2C)alkyl or (1-2C)alkoxy;

(9) $R^1$ is selected from hydrogen, methyl, ethyl, hydroxy, halo, or $R^1$ is a group of the formula:

-$L^1$-$Q^1$ wherein:
  $L^1$ is absent or selected from —C(O)N($R^{10}$)— or —C(O)O—, wherein $R^{10}$ is selected from hydrogen or (1-2C) alkyl;
  $Q^1$ is selected from hydrogen, (1-6C)alkyl, aryl or heteroaryl, each of which is optionally substituted with one or more substituents independently selected from halo, hydroxy, amino, trifluoromethyl, trifluoromethoxy, (1-2C)alkyl or (1-2C)alkoxy; or
  $Q^1$ is optionally substituted with a group of the formula:

—$W^1$—$Z^1$ wherein:
  $W^1$ is absent or —O—;
  $Z^1$ is selected from (1-4C)alkyl, aryl or heteroaryl, wherein $Z^1$ is optionally substituted with one or more substituents selected from halo, hydroxy, amino, trifluoromethyl, trifluoromethoxy, (1-2C)alkyl or (1-2C)alkoxy;

(10) $R^1$ is selected from hydrogen, methyl, ethyl, hydroxy, halo, or $R^1$ is a group of the formula:

-$L^1$-$Q^1$ wherein:
  $L^1$ is absent or —C(O)O—;
  $Q^1$ is selected from hydrogen, (1-6C)alkyl or aryl, each of which is optionally substituted with one or more substituents independently selected from halo, hydroxy, or (1-2C)alkyl; or
  $Q^1$ is optionally substituted with a group of the formula:

—$W^1$—$Z^1$ wherein:
  $W^1$ is absent or —O—;
  $Z^1$ is selected from (1-4C)alkyl or aryl, wherein $Z^1$ is optionally substituted with one or more substituents selected from trifluoromethyl, trifluoromethoxy or (1-2C)alkyl;

(11) $R^2$ is a group

-$L^2$-$Q^3$-$L^3$-$Q^2$ wherein:
  $L^2$ is absent or (1-3C)alkylene optionally substituted with (1-2C)alkyl;
  $Q^3$ is absent or selected from aryl, heterocyclyl or heteroaryl, wherein $Q^3$ is optionally substituted by one or more substituents selected from halo, hydroxy, amino, trifluoromethyl, trifluoromethoxy, (1-4C)alkyl or (1-4C)alkoxy;
  $L^3$ is selected from a direct bond, —($CR^{12}R^{13}$)$_q$—, —O—, —S—, —SO—, —$SO_2$—, —N($R^{12}$)—, —C(O)—, —C(O)N($R^{12}$)—, —N($R^{12}$)C(O)—, —C(O)O— or —OC(O)—, wherein $R^{12}$ and $R^{13}$ are each independently selected from hydrogen or (1-4C) alkyl and wherein q is an integer selected from 1 or 2;
  $Q^2$ is selected from (1-6C)alkyl, aryl, heterocyclyl, or heteroaryl, each of which is optionally substituted with one or more substituents independently selected from halo, cyano, nitro, hydroxy, carboxy, carboxy ester (e.g. methyl or ethyl ester), amino, trifluoromethyl, trifluoromethoxy, (1-4C)alkyl or $OR^{15}$, wherein $R^{15}$ is selected from (1-4C)alkyl or aryl, and wherein any carbon atom of the substituent(s) of $Q^2$ may be further optionally substituted with one or more substituents independently selected from halo, cyano, nitro, hydroxyl, carboxy, carboxy ester, amino, trifluoromethyl, trifluoromethoxy, heterocyclyl, aryl, heteroaryl or $NR^{16}R^{17}$, wherein $R^{16}$ and $R^{17}$ are independently selected from H, (1-4C)alkyl, aryl, aryl(1-2C)alkyl or C(O)O(1-4C)alkyl;

(12) $R^2$ is a group

-$L^2$-$Q^3$-$L^3$-$Q^2$ wherein:
  $L^2$ is absent or (1-3C)alkylene optionally substituted with (1-2C)alkyl;
  $Q^3$ is absent or selected from aryl, heterocyclyl or heteroaryl, wherein $Q^3$ is optionally substituted by one or more substituents selected from halo, hydroxy, amino, trifluoromethyl, trifluoromethoxy, (1-4C)alkyl or (1-4C)alkoxy;
  $L^3$ is selected from a direct bond, —$CR^{12}R^{13}$—, —O—, —S—, —SO—, —$SO_2$—, —N($R^{12}$)—, —C(O)—, —C(O)N($R^{12}$)—, —N($R^{12}$)C(O)—, —C(O)O— or —OC(O)—, wherein $R^{12}$ and $R^{13}$ are each independently selected from hydrogen or (1-4C)alkyl;
  $Q^2$ is selected from (1-6C)alkyl, aryl, heterocyclyl, or heteroaryl, each of which is optionally substituted with one or more substituents independently selected from halo, cyano, nitro, hydroxy, carboxy, carboxy ester (e.g. methyl or ethyl ester), amino, trifluoromethyl, trifluoromethoxy, (1-4C)alkyl or $OR^{15}$, wherein $R^{15}$ is selected from (1-4C)alkyl or aryl, and wherein any carbon atom of the substituent(s) of $Q^2$ may be further optionally substituted with one or more substituents independently selected from halo, cyano, nitro, hydroxyl, carboxy, carboxy ester, amino, trifluoromethyl, trifluoromethoxy, heterocyclyl, aryl, heteroaryl or $NR^{16}R^{17}$, wherein $R^{16}$ and $R^{17}$ are independently selected from H, (1-4C)alkyl, aryl, aryl(1-2C)alkyl or C(O)O(1-4C)alkyl;

(13) $R^2$ is a group

-$L^2$-$Q^3$-$L^3$-$Q^2$ wherein:
$L^2$ is absent or (1-3C)alkylene optionally substituted with (1-2C)alkyl;
$Q^3$ is absent or selected from aryl, heterocyclyl or heteroaryl, wherein $Q^3$ is optionally substituted by one or more substituents selected from halo, hydroxy, amino, trifluoromethyl, trifluoromethoxy, (1-4C)alkyl or (1-4C)alkoxy;
$L^3$ is selected from a direct bond, —$(CR^{12}R^{13})_q$—, —O—, —S—, —SO—, —$SO_2$—, —$N(R^{12})$—, —C(O)—, —$C(O)N(R^{12})$—, —$N(R^{12})C(O)$—, —C(O)O— or —OC(O)—, wherein $R^{12}$ and $R^{13}$ are each independently selected from hydrogen or (1-4C)alkyl and wherein q is an integer selected from 1 or 2;
$Q^2$ is selected from (1-6C)alkyl, aryl, heterocyclyl, or heteroaryl, each of which is optionally substituted with one or more substituents independently selected from halo, cyano, nitro, hydroxy, carboxy, carboxy ester (e.g. methyl or ethyl ester), amino, trifluoromethyl, trifluoromethoxy, (1-4C)alkyl or $OR^{15}$, wherein $R^{15}$ is selected from (1-4C)alkyl or aryl, and wherein any carbon atom of the substituent(s) of $Q^2$ may be further optionally substituted with one or more substituents independently selected from halo, cyano, nitro, hydroxyl, carboxy, carboxy ester, amino, trifluoromethyl, trifluoromethoxy, heterocyclyl, aryl, heteroaryl or $NR^{16}R^{17}$, wherein $R^{16}$ and $R^{17}$ are independently selected from H, (1-4C)alkyl, aryl, aryl(1-2C)alkyl or C(O)O(1-4C)alkyl;

(14) $R^2$ is a group

-$L^2$-$Q^3$-$L^3$-$Q^2$ wherein:
$L^2$ is absent or (1-3C)alkylene optionally substituted with (1-2C)alkyl;
$Q^3$ is absent or selected from aryl, heterocyclyl or heteroaryl, wherein $Q^3$ is optionally substituted by one or more substituents selected from halo, hydroxy, amino, trifluoromethyl, trifluoromethoxy, (1-2C)alkyl or (1-2C)alkoxy;
$L^3$ is selected from a direct bond, —$CR^{12}R^{13}$—, —O—, —S—, —$N(R^{12})$—, —C(O)—, —$C(O)N(R^{12})$—, —$N(R^{12})C(O)$—, —C(O)O— or —)C(O)—, wherein $R^{12}$ and $R^{13}$ are each independently selected from hydrogen or (1-2C)alkyl;
$Q^2$ is selected from (1-6C)alkyl, aryl, heterocyclyl, or heteroaryl, each of which is optionally substituted with one or more substituents independently selected from halo, hydroxy, amino, trifluoromethyl, trifluoromethoxy, (1-4C)alkyl or $OR^{15}$, wherein $R^{15}$ is selected from (1-4C)alkyl or aryl, and wherein any carbon atom of the substituent(s) of $Q^2$ may be further optionally substituted with one or more substituents independently selected from halo, hydroxyl, amino, trifluoromethyl, trifluoromethoxy or $NR^{16}R^{17}$, wherein $R^{16}$ and $R^{17}$ are independently selected from H, (1-4C)alkyl, aryl, aryl(1-2C)alkyl or C(O)O(1-4C)alkyl;

(15) $R^2$ is a group

-$L^2$-$Q^3$-$L^3$-$Q^2$ wherein:
$L^2$ is absent or (1-3C)alkylene optionally substituted with (1-2C)alkyl;
$Q^3$ is absent or selected from aryl, heterocyclyl or heteroaryl, wherein $Q^3$ is optionally substituted by one or more substituents selected from halo, trifluoromethyl, trifluoromethoxy or (1-2C)alkyl;
$L^3$ is selected from a direct bond, —$CR^{12}R^{13}$—, —O—, —S— or —$N(R^{12})$—, wherein $R^{12}$ and $R^{13}$ are each independently selected from hydrogen or (1-2C)alkyl;
$Q^2$ is selected from (1-6C)alkyl, aryl, heterocyclyl, or heteroaryl, each of which is optionally substituted with one or more substituents independently selected from halo, hydroxy, amino, trifluoromethyl, trifluoromethoxy, (1-4C)alkyl or $OR^{15}$, wherein $R^{15}$ is selected from (1-4C)alkyl or aryl, and wherein any carbon atom of the substituent(s) of $Q^2$ may be further optionally substituted with one or more substituents independently selected from halo, trifluoromethyl, trifluoromethoxy or $NR^{16}R^{17}$, wherein $R^{16}$ and $R^{17}$ are independently selected from H, (1-4C)alkyl, or aryl(1-2C)alkyl;

(16) $R^2$ is a group

-$L^2$-$Q^3$-$L^3$-$Q^2$ wherein:
$L^2$ is absent or (1-3C)alkylene;
$Q^3$ is absent or selected from aryl or heteroaryl, wherein $Q^3$ is optionally substituted by one or more substituents selected from halo, trifluoromethyl, trifluoromethoxy or (1-2C)alkyl;
$L^3$ is selected from a direct bond, —$CR^{12}R^{13}$—, —O—, —S— or —$N(R^{12})$—, wherein $R^{12}$ and $R^{13}$ are each independently selected from hydrogen or (1-2C)alkyl;
$Q^2$ is selected from (1-6C)alkyl, aryl, heterocyclyl, or heteroaryl, each of which is optionally substituted with one or more substituents independently selected from halo, hydroxy, trifluoromethyl, trifluoromethoxy, (1-4C)alkyl or $OR^{15}$, wherein $R^{15}$ is selected from (1-4C)alkyl or aryl, and wherein any carbon atom of the substituent(s) of $Q^2$ may be further optionally substituted with one or more substituents independently selected from halo, trifluoromethyl, trifluoromethoxy or $NR^{16}R^{17}$, wherein $R^{16}$ and $R^{17}$ are independently selected from H or aryl(1-2C)alkyl;

(17) $R^3$ is selected from hydrogen, hydroxy, (1-4C)alkyl, aryl or aryl-(1-2C)alkyl;
(18) $R^3$ is selected from hydrogen, hydroxy, (1-4C)alkyl, phenyl or phenyl-(1-2C)alkyl;
(19) $R^3$ is selected from hydrogen, hydroxy or (1-4C)alkyl;
(20) $R^3$ is selected from hydrogen or hydroxy;
(21) $R^4$ is selected from hydrogen or (1-4C)alkyl;
(22) $R^4$ is (1-4C)alkyl.

Suitably, a heteroaryl or heterocyclyl group as defined herein is a monocyclic heteroaryl or heterocyclyl group comprising one, two or three heteroatoms selected from N, O or S.

Suitably, a heteroaryl is a 5- or 6-membered heteroaryl ring comprising one, two or three heteroatoms selected from N, O or S.

Suitably, a heterocyclyl group is a 4-, 5- or 6-membered heterocyclyl ring comprising one, two or three heteroatoms selected from N, O or S. Most suitably, a heterocyclyl group is a 5- or 6-membered ring comprising one, two or three heteroatoms selected from N, O or S [e.g. morpholinyl (e.g. 4-morpholinyl), oxetane, methyloxetane (e.g. 3-methyloxetane), pyrrolidinone (e.g. pyrrolidin-2-one)].

Suitably an aryl group is phenyl.
Suitably, Y is CH.

Suitably, X is as defined in any one of paragraphs (2) to (5) above. Most suitably, X is as defined in paragraph (5).

Suitably, $R^1$ is as defined in any one of paragraphs (6) to (10) above. Most suitably, $R^1$ is as defined in paragraph (10).

Suitably, $R^2$ is as defined in any one of paragraphs (11) to (16) above. Most suitably, $R^2$ is as defined in paragraph (16).

Suitably, $R^3$ is as defined in any one of paragraphs (17) to (20) above. Most suitably, $R^3$ is as defined in paragraph (20).

Suitably, $R^4$ is as defined in any one of paragraphs (21) to (22) above. Most suitably, $R^4$ is (1-4C)alkyl.

In a particular group of cytochrome bd inhibitors of the invention, Y is CH, i.e. the compounds have either the structural formula Ia or IIa (sub-definitions of formulae I and II) shown below:

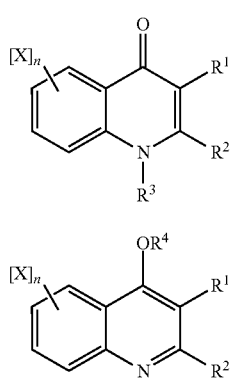

Formula Ia

Formula IIb wherein n, X, $R^1$, $R^2$ and $R^3$ each have any one of the meanings defined herein; or a pharmaceutically acceptable salt thereof.

In an embodiment of the cytochrome bd inhibitors of formulae Ia or IIa:
n is 0, 1 or 2;
X is as defined in any one of paragraphs (2) to (5) above;
$R^1$ is as defined in any one of paragraphs (6) to (10) above;
$R^2$ is as defined in any one of paragraphs (11) to (16) above;
$R^3$ is as defined in any one of paragraphs (17) to (20) above; and
$R^4$ is as defined in any one of paragraphs (21) to (22) above.

In another embodiment of the cytochrome bd inhibitors of formulae Ia or IIa:
n is 0, 1 or 2;
X is as defined in any one of paragraphs (3) to (5) above;
$R^1$ is as defined in any one of paragraphs (8) to (10) above;
$R^2$ is as defined in any one of paragraphs (15) to (16) above;
$R^3$ is as defined in any one of paragraphs (18) to (20) above; and
$R^4$ is as defined paragraphs (22) above.

In another embodiment of the cytochrome bd inhibitors of formulae Ia or IIa:
n is 0, 1 or 2;
X is as defined in paragraph (5) above;
$R^1$ is as defined in any one of paragraphs (9) to (10) above;
$R^2$ is as defined in any one of paragraphs (15) to (16) above;
$R^3$ is as defined in any one of paragraphs (19) to (20) above; and
$R^4$ is as defined paragraphs (22) above.

Particular cytochrome bd inhibitors of the present invention include any of the compounds exemplified in the present application, or a pharmaceutically acceptable salt or solvate thereof, and, in particular, any of the following:

3-Methyl-2-(6-(4-(trifluoromethoxy)phenoxy)pyridin-3-yl)quinolin-4(1H)-one (CK-3-22);

2-(6-(4-Fluorophenoxy)pyridin-3-yl)-3-methylquinolin-4(1H)-one (CK-3-14);

7-Methoxy-3-methyl-2-(6-(4-(trifluoromethoxy)phenoxy)pyridin-3-yl)quinolin-4(1H)-one (RKA-259);

3-Methyl-2-(4-(piperidin-1-yl)phenyl)quinolin-4(1H)-one (RKA-307);

7-Methoxy-3-methyl-2-(6-(4-(trifluoromethoxy)phenoxy)pyridin-3-yl)quinolin-4(1H)-one (RKA-310);

5,7-Difluoro-3-methyl-2-(4-(piperidin-1-yl)phenyl)quinolin-4(1H)-one (MTD-403);

2-(4-Benzylphenyl)-3-methylquinolin-4(1H)-one (CK-2-88);

2-(4-Benzylphenyl)-4-methoxy-3-methylquinoline (CK-3-23);

3-Methyl-2-(4-(4-(trifluoromethoxy)phenoxy)phenyl)quinolin-4(1H)-one (CK-2-63);

2-Methyl-3-(4-(4-(trifluoromethoxy)phenoxy)phenyl)quinolin-4(1H)-one (PG-203);

2-(4-(4-(Trifluoromethoxy)benzyl)phenyl)quinolin-4(1H)-one (RKA-70);

1-Hydroxy-2-(4-(4-(trifluoromethoxy)benzyl)phenyl)quinolin-4(1H)-one (RKA-73);

2-(4-(4-Fluorobenzyl)phenyl)-3-methylquinolin-4(1H)-one (LT-9);

Ethyl 4-oxo-2-(4-(4-(trifluoromethoxy)benzyl)phenyl)-1,4-dihydroquinoline-3-carboxylate (GN-171);

3-Methyl-2-(6'-(trifluoromethyl)-[2,3'-bipyridin]-5-yl)quinolin-4(1H)-one (PG-128);

3-Methyl-2-(6-(4-(trifluoromethoxy)phenyl)pyridin-3-yl)quinolin-4(1H)-one (SL-2-25);

Ethyl 2-(4'-chloro-[1,1'-biphenyl]-4-yl)-4-oxo-1,4-dihydroquinoline-3-carboxylate (WDH -1U-10);

2-(1-(4-(Trifluoromethoxy)benzyl)-1H-pyrazol-4-yl)quinolin-4(1H)-one (WDH-1W-5);

3-Methyl-2-(1-(4-(trifluoromethoxy)benzyl)-1H-pyrazol-4-yl)quinolin-4(1H)-one (WDH-2A -9);

Ethyl 4-oxo-2-(4'-(trifluoromethoxy)-[1,1'-biphenyl]-4-yl)-1,4-dihydroquinoline-3-carboxylate (WDH-1V-10);

Ethyl 2-(4'-chloro-[1,1'-biphenyl]-4-yl)-4-oxo-1,4-dihydroquinoline-3-carboxylate (WDH-1V -9);

3-Isopropyl-2-(1-(4-(trifluoromethoxy)benzyl)-1H-pyrazol-4-yl)quinolin-4(1H)-one (WDH -2G-6);

3-Methyl-2-(1-(4-(trifluoromethoxy)phenethyl)-1H-pyrazol-4-yl)quinolin-4(1H)-one (WDH -2R-4);

3-Methyl-2-(4'-(trifluoromethoxy)-[1,1'-biphenyl]-4-yl)quinolin-4(1H)-one (SL-2-34);

3-Methyl-2-(2'-(trifluoromethyl)-[1,1'-biphenyl]-4-yl)quinolin-4(1H)-one (SL-2-36);

2-(2'-Fluoro-[1,1'-biphenyl]-4-yl)-3-methylquinolin-4(1H)-one (SL-3-3);

3-Methyl-2-(6-(4-(trifluoromethyl)phenyl)pyridin-3-yl)quinolin-4(1H)-one (RKA 142);

2-(4-((4,4-Difluorocyclohexyl)oxy)phenyl)-3-methylquinolin-4(1H)-one (PG105);

3-Methyl-2-(4-(3-(2-morpholinoethoxy)benzyl)phenyl)quinolin-4(1H)-one (PG201);

2-(Hydroxymethyl)-3-(4-(4-(trifluoromethoxy)phenoxy)phenyl)quinolin-4(1H)-one (PG208);

7-Hydroxy-3-methyl-2-(4-(4-(trifluoromethoxy)benzyl) phenyl)quinolin-4(1H)-one (SCR-05-01D);
8-Hydroxy-3-methyl-2-(4-(4-(trifluoromethoxy)benzyl) phenyl)quinolin-4(1H)-one (SCR-06-03D);
5-Methoxy-3-methyl-2-(6-(4-(trifluoromethoxy)phenyl) pyridin-3-yl)quinolin-4(1H)-one (SCR-04-04);
6-Methoxy-3-methyl-2-(4-(4-(trifluoromethoxy)benzyl) phenyl)quinolin-4(1H)-one (SCR-05-03);
3-Methyl-2-(3-(4-(trifluoromethoxy)benzyl)phenyl)quinolin-4(1H)-one (CK-2-58);
3-Methyl-2-(4-(4-(trifluoromethoxy)benzyl)phenyl)quinolin-4(1H)-one (CK-2-67);
2-(4-(4-Methoxybenzyl)phenyl)-3-methylquinolin-4(1H)-one (CK-2-96);
2-(4-Benzylphenyl)-3-methylquinolin-4(1H)-one (CK-2-88);
6-Fluoro-7-hydroxy-2-(4-(4-(trifluoromethoxy)benzyl)phenyl)quinolin-4(1H)-one (CK-3-68);
3-Methyl-2-(4-(4-(2-morpholinoethoxy)benzyl)phenyl)quinolin-4(1H)-one (CK-4-2);
3-Methyl-2-(4-(3-(2-morpholinoethoxy)phenoxy)phenyl) quinolin-4(1H)-one (CK-4-15); or
3-Methyl-2-(6-(4-(trifluoromethoxy)phenoxy)pyridin-3-yl) quinolin-4(1H)-one (CK-3-22).

Other compounds suitable for use as a cytochrome bd inhibitor of the present invention are described in WO2012069586, the entire contents of which are incorporated herein by reference.

The various functional groups and substituents making up the cytochrome bd inhibitors of formula I or II are typically chosen such that the molecular weight of the compound of formula I or II does not exceed 1000. More usually, the molecular weight of the compound will be less than 900, for example less than 800, or less than 700, or less than 650, or less than 600. More preferably, the molecular weight is less than 550 and, for example, is 500 or less.

A suitable pharmaceutically acceptable salt of a cytochrome bd inhibitor of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a cytochrome bc inhibitor of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl) amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn-Ingold-Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The cytochrome bd inhibitors of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess cytochrome bd activity.

The present invention also encompasses cytochrome bc inhibitors of the invention as defined herein which comprise one or more isotopic substitutions. For example, H may be in any isotopic form, including $^1H$, $^2H(D)$, and $^3H$ (T); C may be in any isotopic form, including $^{12}C$, $^{13}C$, and $^{14}C$; and O may be in any isotopic form, including $^{16}O$ and $^{18}O$; and the like.

It is also to be understood that certain cytochrome bd inhibitors of formula I or II may exist in solvated as well as unsolvated forms such as, for example, hydrated forms. It is to be understood that the invention encompasses all such solvated forms that possess cytochrome bd activity.

Cytochrome bd inhibitors of formula I or II may exist in a number of different tautomeric forms and references to cytochrome bd inhibitors of formula I or II include all such forms. For the avoidance of doubt, where a compound can exist in one of several tautomeric forms, and only one is specifically described or shown, all others are nevertheless embraced by formulae I or II. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

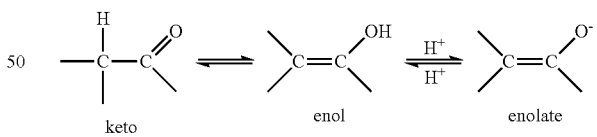

Cytochrome bd inhibitors of formula I or II containing an amine function may also form N-oxides. A reference herein to a cytochrome bd inhibitor of formulae I or II that contains an amine function also includes the N-oxide. Where a cytochrome bd inhibitor contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages.

More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

The cytochrome bd inhibitors of formula I or II may be administered in the form of a pro-drug which is broken down in the human or animal body to release a cytochrome bd inhibitor of the invention. A pro-drug may be used to alter the physical properties and/or the pharmacokinetic properties of a cytochrome bd inhibitor of the invention. A pro-drug can be formed when the cytochrome bd inhibitor of the invention contains a suitable group or substituent to which a property-modifying group can be attached. Examples of pro-drugs include in vivo cleavable ester derivatives that may be formed at a carboxy group or a hydroxy group in a compound of the formula I and in-vivo cleavable amide derivatives that may be formed at a carboxy group or an amino group in a cytochrome bd inhibitor of formula I or II.

Accordingly, the present invention includes those cytochrome bd inhibitors of formula I or II as defined hereinbefore when made available by organic synthesis and when made available within the human or animal body by way of cleavage of a pro-drug thereof. Accordingly, the present invention includes those cytochrome bd inhibitors of formula I or II that are produced by organic synthetic means and also such cytochrome bd inhibitors that are produced in the human or animal body by way of metabolism of a precursor compound, that is a cytochrome bd inhibitor of formula I or II may be a synthetically-produced compound or a metabolically-produced compound.

A suitable pharmaceutically acceptable pro-drug of a cytochrome bd inhibitor of formula I or II is one that is based on reasonable medical judgement as being suitable for administration to the human or animal body without undesirable pharmacological activities and without undue toxicity.

Various forms of pro-drug have been described, for example in the following documents:
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Druq Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a cytochrome bd inhibitor of formula I or II that possesses a carboxy group is, for example, an in vivo cleavable ester thereof. An in vivo cleavable ester of a cytochrome bd inhibitor of formula I or II containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenyl-methyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a cytochrome bd inhibitor of formula I or II that possesses a hydroxy group is, for example, an in vivo cleavable ester or ether thereof. An in vivo cleavable ester or ether of a cytochrome bd inhibitor of formula I or II containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include am inomethyl, N-al kylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a cytochrome bd inhibitor of formula I or II that possesses a carboxy group is, for example, an in vivo cleavable amide thereof, for example an amide formed with an amine such as ammonia, a $C_{1-4}$alkylamine such as methylamine, a $(C_{1-4}$alkyl)$_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a cytochrome bd inhibitor of formula I or II that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include am inomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a cytochrome bd inhibitor of formula I or II may be exerted in part by one or more metabolites that are formed within the human or animal body after administration of a cytochrome bd inhibitor of formula I or II. As stated hereinbefore, the in vivo effects of a cytochrome bd inhibitor of formula I or II may also be exerted by way of metabolism of a precursor compound (a pro-drug).

Though the present invention may relate to any cytochrome bd inhibitor or particular group of compounds defined herein by way of optional, preferred or suitable features or otherwise in terms of particular embodiments, the present invention may also relate to any cytochrome bd inhibitor or particular group of compounds that specifically excludes said optional, preferred or suitable features or particular embodiments.

Respiratory Electron Transport Chain Inhibitors

It will be understood that the respiratory electron transport chain inhibitor of the present invention comprises any compound capable of inhibiting a protein complex or enzyme found along the respiratory electron transport chain of a particular organism. Suitably, the respiratory electron transport chain inhibitor of the present invention comprises any compound capable of inhibiting a protein complex or enzyme found along the respiratory electron transport chain of a mycobacterium. Most suitably, the respiratory electron transport chain inhibitor of the present invention comprises any compound capable of inhibiting a protein complex or enzyme found along the respiratory electron transport chain of *Mycobacterium tuberculosis* (Mtb).

Details of the protein complexes and enzymes found along the respiratory electron transport chain of *Mycobacterium tuberculosis* are described in Methods in enzymology, 456, p 303-320.

In an embodiment, the respiratory electron transport chain inhibitor of the present invention comprises any compound capable of inhibiting one or more targets selected from cytochrome bcc, protonmotive NADH dehydrogenase (complex I, nuo), cytochrome bcc oxidase (aa3) and $F_1F_0$ ATPase. Suitably, the respiratory electron transport chain inhibitor of the present invention comprises any compound capable of inhibiting one or more targets selected from cytochrome bcc, cytochrome bcc oxidase (aa3) and $F_1F_0$ ATPase. More suitably, the respiratory electron transport chain inhibitor of the present invention comprises any compound capable of inhibiting one or more targets selected from cytochrome bcc or $F_1F_0$ ATPase. Most suitably, the respiratory electron transport chain inhibitor of the present invention comprises any compound capable of inhibiting cytochrome bcc.

In another embodiment, the respiratory electron transport chain inhibitor of the present invention is a cytochrome bcc or $F_1F_0$ ATPase inhibitor. Suitably, the respiratory electron transport chain inhibitor of the present invention is a cytochrome bcc inhibitor.

The various functional groups and substituents making up the respiratory electron transport chain inhibitors of the present invention are typically chosen such that the molecular weight of the compound does not exceed 1000. More usually, the molecular weight of the compound will be less than 900, for example less than 800, or less than 700, or less than 650, or less than 600. More preferably, the molecular weight is less than 550 and, for example, is 500 or less.

In another embodiment, the respiratory electron transport chain inhibitor of the present invention is selected from lansoprazole, bedaquiline (TMC207), MTC420, AWE402, Q203, Isoniazid, phenothiazines or any suitable prodrug or analogue thereof. Suitably, the respiratory electron transport chain inhibitor of the present invention is selected from bedaquiline (TMC207), MTC420, AWE402, Q203, Isoniazid, phenothiazines or any suitable prodrug or analogue thereof. More suitably, the respiratory electron transport chain inhibitor of the present invention is selected from bedaquiline (TMC207), MTC420, AWE402 or any suitable prodrug or analogue thereof. Most suitably, the respiratory electron transport chain inhibitor of the present invention is bedaquiline (TMC 207) or any suitable prodrug or analogue thereof.

Structures of non-limiting examples of suitable respiratory electron transport chain inhibitors of the present invention are shown below.

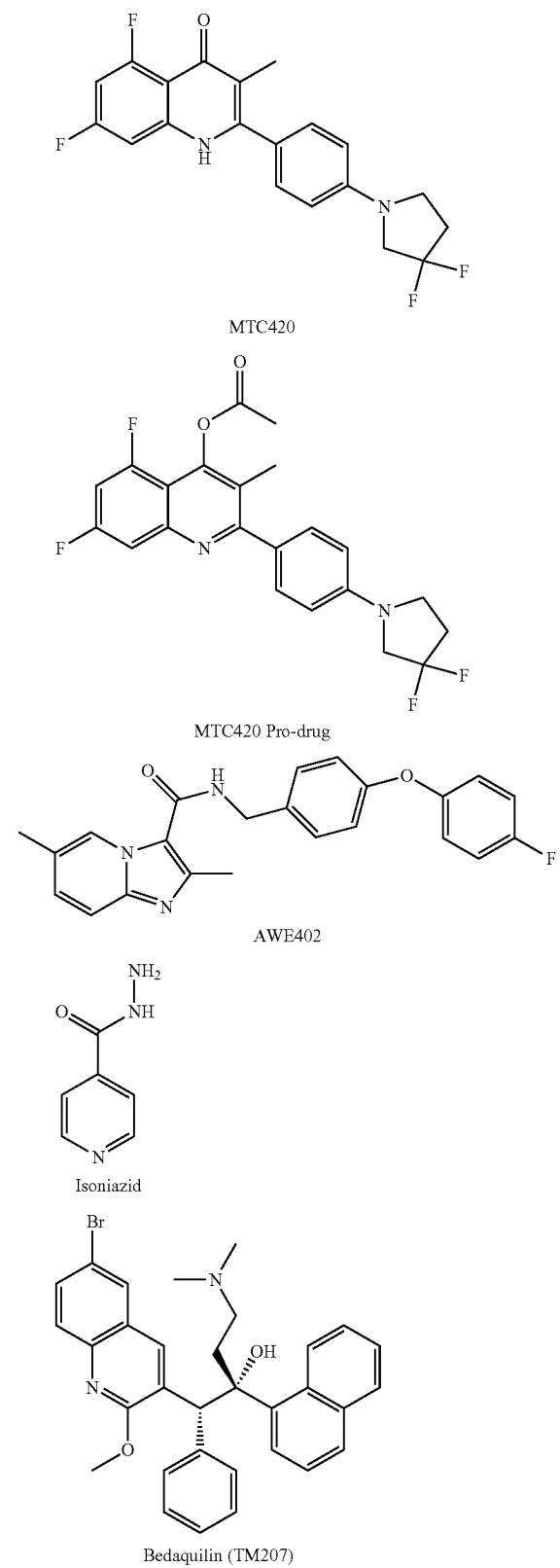 [SMILES: Cc1c(-c2ccc(N3CCC(F)(F)C3)cc2)[nH]c2cc(F)cc(F)c2c1=O ; CC(=O)Oc1c(C)c(-c2ccc(N3CCC(F)(F)C3)cc2)nc2cc(F)cc(F)c12 ; Cc1ccc2nc(C)c(C(=O)NCc3ccc(Oc4ccc(F)cc4)cc3)n2c1 ; NNC(=O)c1ccncc1 ; COc1nc2ccc(Br)cc2cc1[C@@H](c1ccccc1)[C@@](O)(CCN(C)C)c1cccc2ccccc12]

-continued

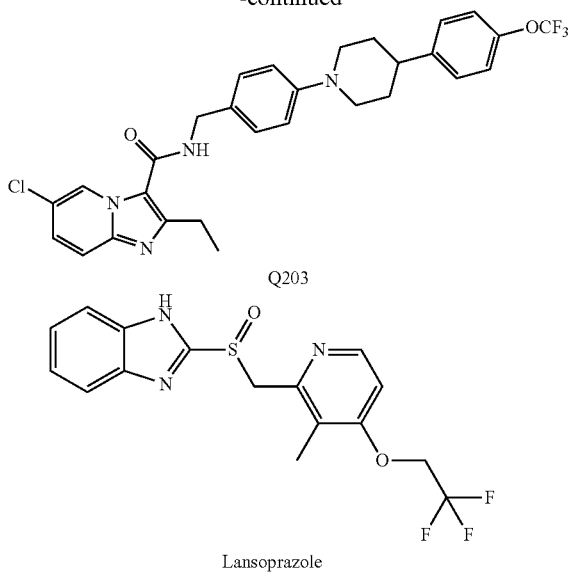

Q203

Lansoprazole

As described hereinabove, one or more respiratory electron transport chain inhibitors may be administered in combination with the cytochrome bd inhibitor described hereinabove.

Biological Activity

The Mtb cytochrome bd inhibition assay described in accompanying Example section, or elsewhere in the literature, may be used to measure the pharmacological effects of the cytochrome bd inhibitors of the present invention.

Although the pharmacological properties of the cytochrome bd inhibitors described herein vary with structural change, as expected, the cytochrome bd inhibitors of the invention were found to be active in these assays.

The cytochrome bd inhibitors of the invention demonstrate a $IC_{50}$ of 20 µM or less in the Mtb cytochrome bd inhibition assay described herein, with preferred cytochrome bd inhibitors of the invention demonstrating an $IC_{50}$ of 5 µM or less and the most preferred cytochrome bd inhibitors of the invention demonstrating an $IC_{50}$ of 1 µM or less.

Pharmaceutical Compositions

According to a further aspect of the invention there is provided a pharmaceutical composition suitable for use in the treatment of a mycobacterial infection which comprises a combination therapeutic product, as defined herein, in association with a pharmaceutically-acceptable excipient or carrier. For example, solid oral forms may contain, together with the active compounds, diluents, such as, for example, lactose, dextrose, saccharose, cellulose, corn starch or potato starch; lubricants, such as, for example, silica, talc, stearic acid, magnesium or calcium stearate, and/or polyethylene glycols; binding agents; such as, for example, starches, arabic gums, gelatin, methylcellulose, carboxymethylcellulose or polyvinyl pyrrolidone; disaggregating agents, such as, for example, starch, alginic acid, alginates or sodium starch glycolate; effervescing mixtures; dyestuffs; sweeteners; wetting agents, such as, for example, lecithin, polysorbates, laurylsulphates; and, in general, non-toxic and pharmacologically inactive substances used in pharmaceutical formulations. Such pharmaceutical compositions may be manufactured in by conventional methods known in the art, such as, for example, by mixing, granulating, tableting, sugar coating, or film coating processes.

The pharmaceutical compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing). Suitably, oral or parenteral administration is preferred. Most suitably, oral administration is preferred.

The pharmaceutical compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient(s) that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a combination therapeutic product of the present invention will naturally vary according to the nature and severity of the condition, the age and sex of the animal or patient and the route of administration, according to well-known principles of medicine.

In using combination therapeutic product of the present invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention relates to certain combination therapies for the treatment of mycobacterial infections, such as, for example, tuberculosis. In particular, the present invention relates to a combination therapeutic product comprising one or more respiratory electron transport chain inhibitors and a cytochrome bd inhibitor, or a pharmaceutically acceptable salt thereof.

Although inhibitors of the *Mycobacterium tuberculosis* respiratory electron transport chain are known, they typically suffer from poor efficacy, meaning high doses of inhibitor are needed in order to be effective at reducing Mtb growth. The need for the administration of such high doses increases the risk of adverse side effects and has ultimately slowed development of such inhibitors.

Surprisingly, the inventors have found that administering one or more respiratory electron transport chain inhibitors in combination with a cytochrome bd inhibitor dramatically increases the efficacy of the resulting combination therapeutic product, when compared with the administration of the respiratory electron transport chain inhibitors and cytochrome bd inhibitors alone. Thus, the synergistic effect seen by the combination therapeutic products of the present invention allows for a significant enhancement in Mtb kill, thereby seemingly addressing many of the issues commonly associated with known tuberculosis treatments.

Figure 10:
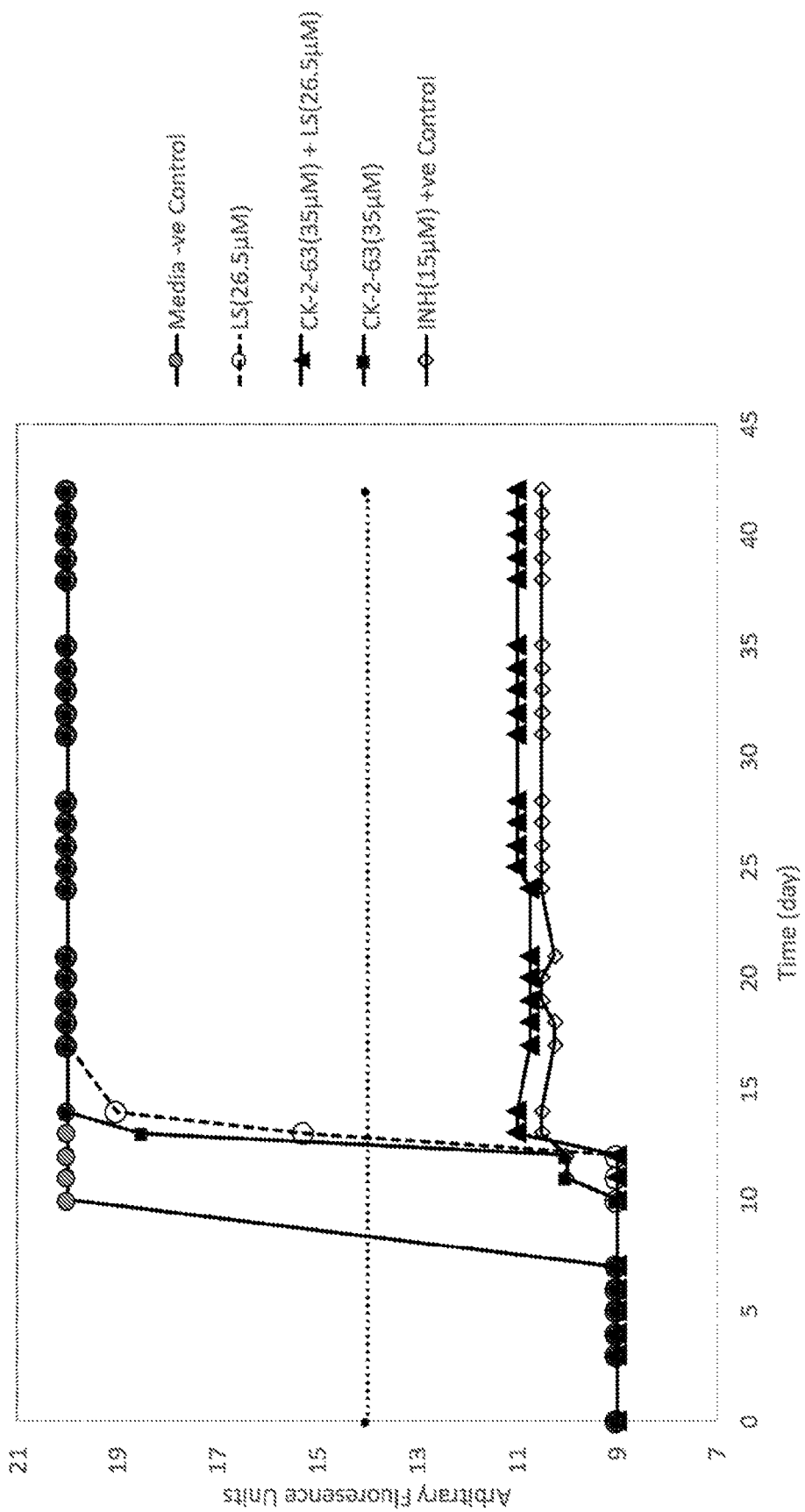

In one aspect, the present invention provides a combination therapeutic product comprising one or more respiratory electron transport chain inhibitors and a cytochrome bd inhibitor for use simultaneously, sequentially or separately in the treatment of a mycobacterial infection.

The present invention therefore provides a method of inhibiting the growth of mycobacteria in vitro or in vivo, said method comprising contacting a cell/microbe with an effective amount of a combination therapeutic product, or a pharmaceutical composition as defined herein. Suitably, the present invention provides a method of inhibiting the growth of mycobacterium tuberculosis in vitro or in vivo.

The present invention also provides a cytochrome bd inhibitor for use in the treatment of a mycobacterial infection, administered in combination with one or more respiratory electron transport chain inhibitors.

Thus, the present invention therefore provides a method of inhibiting the growth of mycobacteria in vitro or in vivo, said method comprising contacting a cell/microbe with an effective amount of a cytochrome bd inhibitor in combination with an effective amount one or more respiratory electron transport chain inhibitors.

The present invention also provides a method for the treatment or prophylaxis of a mycobacterial infection comprising simultaneously, sequentially or separately administering an effective amount of a combination therapeutic product, or a pharmaceutical composition, to a patient, such as a human, in need of such treatment.

Furthermore, the present inventions also provides a method for the treatment or prophylaxis of a mycobacterial infection comprising simultaneously, sequentially or separately administering an effect amount of a cytochrome bd inhibitor, in combination with one or more respiratory electron transport chain inhibitors.

The present invention also provides the use of a combination therapeutic product, or a pharmaceutical composition, for the manufacture of a medicament for administration simultaneously, sequentially or separately to a patient in need thereof, such as a human, for the treatment or prophylaxis of a mycobacterial infection.

The present invention also provides the use of a cytochrome bd inhibitor, in combination with one or more respiratory electron transport chain inhibitors, in the treatment of a mycobacterial infection.

In an embodiment, the mycobacterial infection is selected from Buruli Ulcers, Leprosy, Hansen's disease or tuberculosis. Suitably, the mycobacterial infection is selected from Leprosy or tuberculosis. More suitably, the mycobacterial infection is tuberculosis. Most suitable, the mycobacterial infection is multidrug resistant tuberculosis.

Furthermore, the present invention provides a pharmaceutical composition suitable for use in the synergistic treatment of a mycobacterial infection which comprises a combination therapeutic product, in association with a pharmaceutically-acceptable excipient or carrier.

It will be understood by a person skilled in the art that the patient in need thereof is suitably a human, but may also include, but is not limited to, primates (e.g. monkeys), commercially farmed animals (e.g. horses, cows, sheep or pigs) and domestic pets (e.g. dogs, cats, guinea pigs, rabbits, hamsters or gerbils). Thus the patient in need thereof may be any mammal that is capable of being infected by a bacterium (e.g. a mycobacterium).

Routes of Administration

The combination therapeutic product of the present invention, or pharmaceutical compositions comprising the combination therapeutic product, may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

EXAMPLES

DESCRIPTION OF DRAWINGS

Embodiments of the invention will be described, by way of example only, with reference to the accompanying drawings, in which:

FIG. 1 shows the steady-state kinetics of quinol:Mtb bd-I activity with varying artificial quinol substrates, in which (a) shows the oxidation of decylubiquinol (dQH2), (b) shows the oxidation of ubiquinol-1 (Q1H2) by the Mtb bd-I and (c) shows the oxidation of ubiquinol-2 (Q2H2) by Mtb bd-I. Data points are the mean initial rates of experimental duplicate obtained at each quinol concentration indicated.

FIG. 2 shows the Mtb bd-I sensitivity (IC50) for the quinolone inhibitors CH-2-63 and MTD -403.

FIG. 3 shows the time to positivity traces of Mtb grown in Mycobacteria Growth Indicator Tubes (MGITs) containing MTC 420 and CK-2-63 alone and a combination thereof.

FIG. 4 shows the isobole analysis of MTC420 vs. CK-2-63 using the 5-day alamar blue in vitro assay.

FIG. 5 shows the time to positivity traces of Mtb grown in MGITs containing a selection of drugs alone and in combination.

FIG. 6 shows the time-kill kinetics of TMC207 (benaquiline) at varying concentrations (250 nM and 372 nM), either alone or in combination with the cyt bd inhibitor CK-2-63 (35 μM).

FIG. 7 shows the time-kill kinetics of TMC207 (benaquiline, 750 nM), either alone or in combination with the cyt bd inhibitor CK-2-63 (at both 3.5 μM and 35 μM).

FIG. 8 shows the concentration of bedaquiline required to reach half-maximal killing rate of *M. tuberculosis* for both bedaquiline alone and bedaquiline in combination with CK-2-63.

FIG. 9 shows the time to positivity of Mtb grown in MGITs containing drugs alone or in combination. Compounds were present at 5×IC90 (established from MABA assays). TMC207 (T, 0.25 μM), AWE402 (A, 0.025pM), CK-2-63 (C, 35 µM), MTC420 (M, 5.5 µM), Isoniazid (INH, 15 µM) containing 7.5×105 Mtb cells per tube.
FIG. 10 shows the time to positivity of Mtb grown in MGITs containing drugs alone or in combination. Compounds were present at 5×IC90 (established from MABA assays). Lansoprazole (LS, 26.5 µM), CK-2-63 (35 µM) and Isoniazid (INH, 15 µM).
Synthetic Procedures
General Procedures
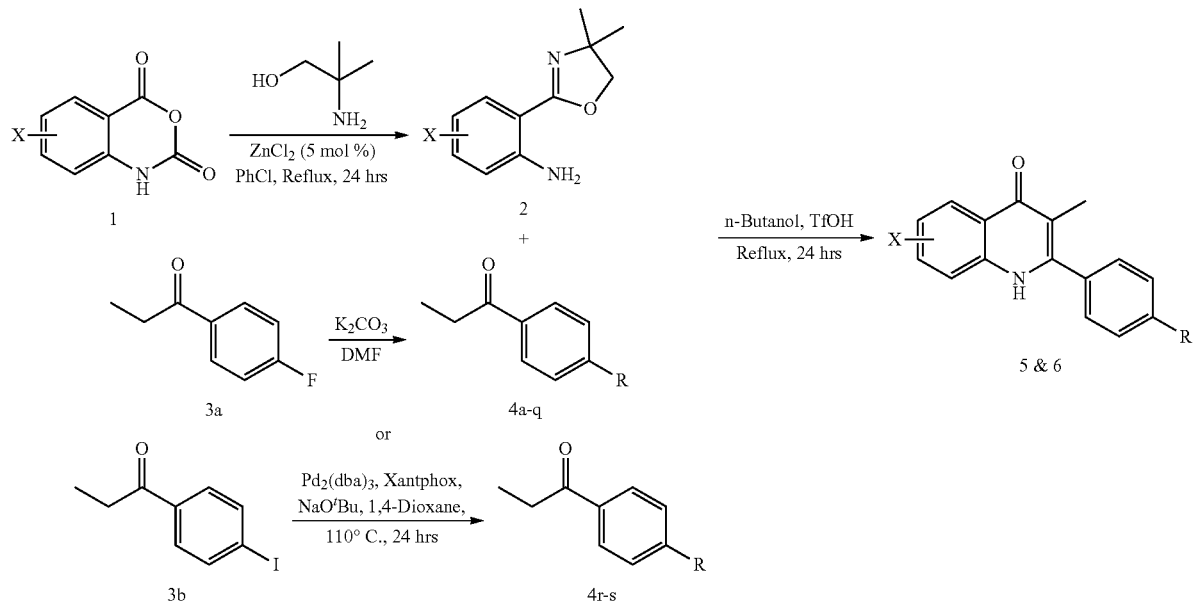
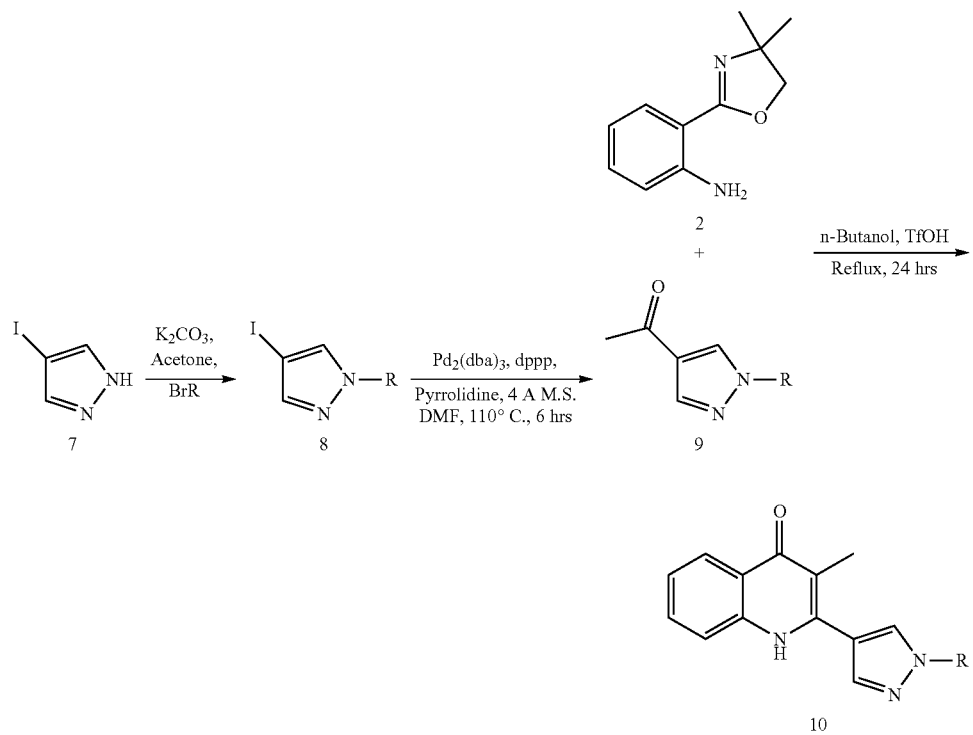

Scheme 3-Synthesis of Quinolone 12

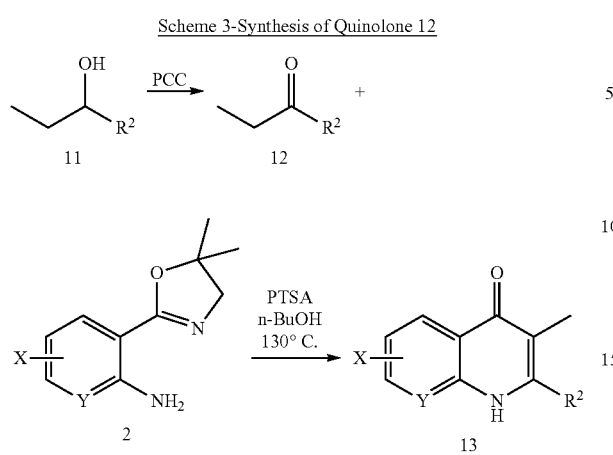

General Procedure for the Preparation of Oxazoline 2

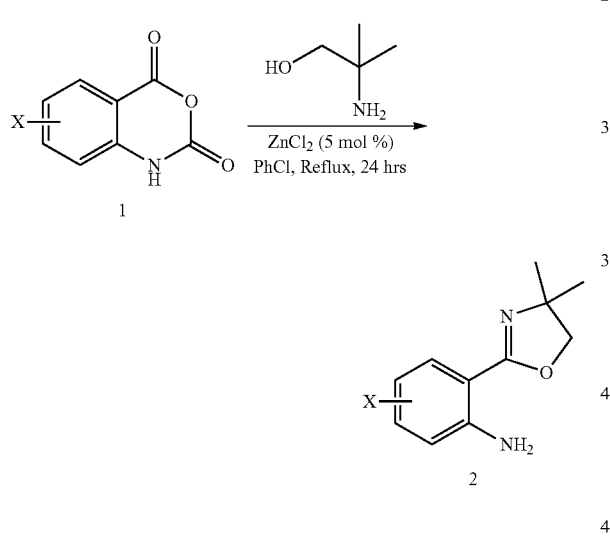

Compound 1 (17.6 mmol) was suspended in anhydrous chlorobenzene (50 mL) under nitrogen. 2-Methyl-2-amino-1-propanol (2.28 mL, 23.9 mmol, 1.3 equiv) was added to the suspension followed by anhydrous ZnCl₂ (0.3 g, 2.2 mmol), and the mixture was heated to reflux for 24 h. After the reflux period it was cooled to room temperature. The solvent was removed under reduced pressure, the residue was added to ethyl acetate and the resulting solution was washed with brine. The aqueous layer was extracted with ethyl acetate (50 mL×2) and the combined organic layer was dried over Na₂SO₄, filtered and the solvent was removed under reduced pressure to give the crude product. Purification by column chromatography using 10% ethyl acetate in hexane gave the desired compound 2.

Note, where X=H, the compound is commercially available and therefore wasn't synthesised.

The following compounds were prepared according to the general procedure described above.

Preparation of 2-(4,4-dimethyl-4,5-dihydrooxazol-2-yl)-3-fluoroaniline 2a

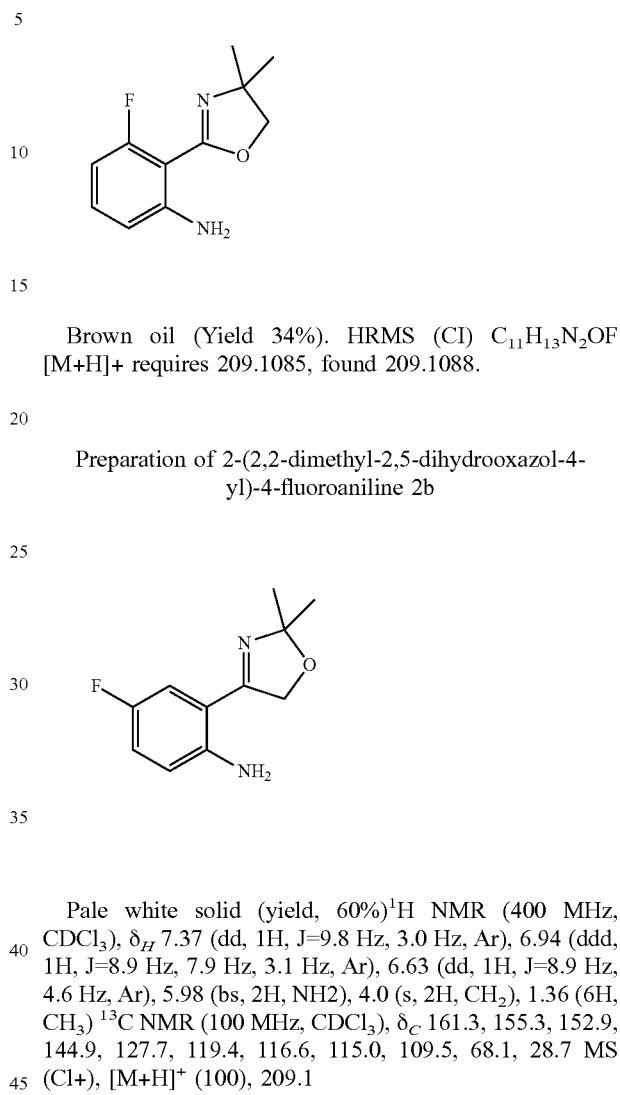

Brown oil (Yield 34%). HRMS (CI) $C_{11}H_{13}N_2OF$ [M+H]+ requires 209.1085, found 209.1088.

Preparation of 2-(2,2-dimethyl-2,5-dihydrooxazol-4-yl)-4-fluoroaniline 2b

Pale white solid (yield, 60%) $^1$H NMR (400 MHz, CDCl₃), $\delta_H$ 7.37 (dd, 1H, J=9.8 Hz, 3.0 Hz, Ar), 6.94 (ddd, 1H, J=8.9 Hz, 7.9 Hz, 3.1 Hz, Ar), 6.63 (dd, 1H, J=8.9 Hz, 4.6 Hz, Ar), 5.98 (bs, 2H, NH2), 4.0 (s, 2H, CH₂), 1.36 (6H, CH₃) $^{13}$C NMR (100 MHz, CDCl₃), $\delta_C$ 161.3, 155.3, 152.9, 144.9, 127.7, 119.4, 116.6, 115.0, 109.5, 68.1, 28.7 MS (CI+), [M+H]⁺ (100), 209.1

Preparation of 5-chloro-2-(2,2-dimethyl-2,5-dihydrooxazol-4-yl)aniline 2c

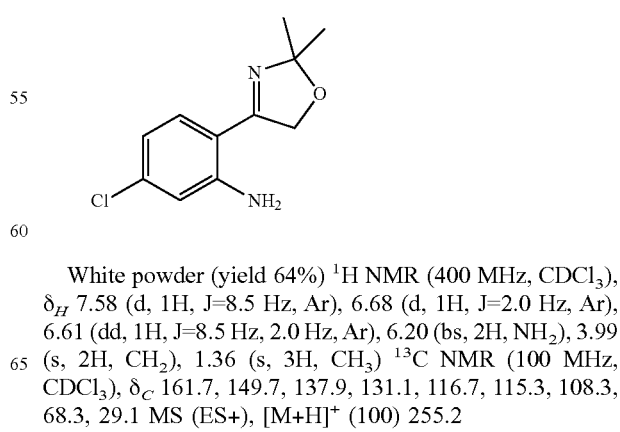

White powder (yield 64%) $^1$H NMR (400 MHz, CDCl₃), $\delta_H$ 7.58 (d, 1H, J=8.5 Hz, Ar), 6.68 (d, 1H, J=2.0 Hz, Ar), 6.61 (dd, 1H, J=8.5 Hz, 2.0 Hz, Ar), 6.20 (bs, 2H, NH₂), 3.99 (s, 2H, CH₂), 1.36 (s, 3H, CH₃) $^{13}$C NMR (100 MHz, CDCl₃), $\delta_C$ 161.7, 149.7, 137.9, 131.1, 116.7, 115.3, 108.3, 68.3, 29.1 MS (ES+), [M+H]⁺ (100) 255.2

Preparation of 2-(4,4-Dimethyl-4,5-dihydrooxazol-2-yl)-5-methoxyaniline 2d

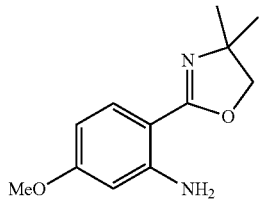 [SMILES: COc1ccc(C2=NC(C)(C)CO2)c(N)c1]

White solid (2.25 g, 75%). $R_f$=0.48, 20% ethyl acetate in hexane; mp 92° C.; $^1$H NMR (400 MHz, CDCl$_3$) δ 7.59 (d, J=8.8 Hz, 1H, H-3), 6.24 (dd, J=8.8, 2.5 Hz, 1H, H-4), 6.17 (d, J=2.4 Hz, 1H, H-6), 6.13 (s, 2H, NH$_2$), 3.96 (s, 2H, OCH$_2$), 3.78 (s, 3H, OCH$_3$), 1.35 (s, 6H, CH$_3$); $^{13}$C NMR (101 MHz, CDCl$_3$) δ 162.97, 162.29 (C-5), 150.58 (C-1), 131.40 (C-3), 103.86 (C-6), 103.52, 99.66 (C-4), 77.62 (C(CH3)2), 68.01 (OCH$_2$), 55.52 (OCH$_3$), 29.17 (CH$_3$); IR vmax (neat)/cm$^{-1}$ 3398.0, 3251.4, 2975.6, 2894.6, 1635.3, 1600.6, 1365.4, 1270.9, 1214.9 and 1029.8; MS (CI) C$_{12}$H$_{17}$N$_2$O$_2$[M+H]$^+$ m/z 221.2; Anal. C$_{12}$H$_{16}$N$_2$O$_2$ requires C 65.43%, H 7.32%, N 12.72%, found C 65.41%, H 7.38%, N 12.93%.

Preparation of 2-(4,4-dimethyl-4,5-dihydrooxazol-2-yl)-3,5-difluoroaniline 2e

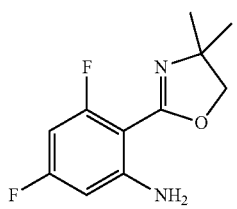 [SMILES: CC1(C)COC(c2c(N)cc(F)cc2F)=N1]

Yellow solid (Yield 68%) $^1$H NMR (400 MHz, CDCl$_3$) $δ_H$ 6.45 (br. s, 2H, NH$_2$), 6.19-6.14 (m, 1H, Ar), 6.14-6.08 (m, 1H, Ar), 4.05 (s, 3H, OCH$_3$), 1.37 (s, 6H, CH$_3$); $^{13}$C NMR (101 MHz, CDCl$_3$) $δ_C$ 169.50, 165.73 (dd, J=86.2, 16.3 Hz), 163.22 (dd, J=93.3, 16.3 Hz), 160.66 (C=N), 151.70 (dd, J=14.2, 7.8 Hz), 117.74, 97.78 (dd, J=24.3, 3.2 Hz), 93.14, 78.27 (OCH$_2$), 66.82 (C(CH$_3$)$_2$), 29.03 (CH$_3$); MS (CI+) 227.2 [M+H]$^+$.

Preparation of 2-(4,4-dimethyl-4,5-dihydrooxazol-2-yl)-4,5-dimethoxyaniline 2f

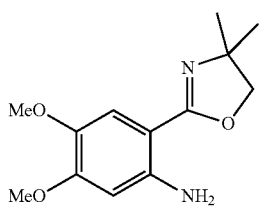 [SMILES: COc1cc(N)c(C2=NC(C)(C)CO2)cc1OC]

Pale yellow solid (Yield 52%) $^1$H NMR (400 MHz, CDCl$_3$) $δ_H$ 7.16 (s, 1H, Ar), 6.23 (s, 1H, Ar), 5.89 (br. s, 2H, NH$_2$), 3.98 (s, 2H, CH$_2$), 3.86 (s, 3H, OCH$_3$), 3.83 (s, 3H, OCH$_3$), 1.36 (s, 6H, CH$_3$); $^{13}$C NMR (101 MHz, CDCl$_3$) $δ_C$ 162.22, 153.09, 144.81, 140.85, 112.15, 101.23, 99.57, 77.62, 68.12 (OCH$_2$), 56.84 (OCH$_3$), 56.12 (OCH$_3$), 29.18 (CH$_3$); MS (CI+) 251.4 [M+H]$^+$.

Preparation of 2-(4,4-dimethyl-4,5-dihydrooxazol-2-yl)-3,5-dimethoxyaniline 2g

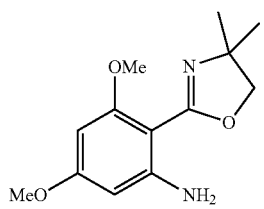 [SMILES: COc1cc(N)c(C2=NC(C)(C)CO2)c(OC)c1]

Pale Yellow solid (Yield 58%) $^1$H NMR (400 MHz, CDCl$_3$) δ 5.85-5.82 (m, 2H, Ar), 4.07 (s, 2H, CH$_2$), 3.83 (s, 3H, OCH$_3$), 3.77 (s, 3H, OCH$_3$), 1.40 (s, 6H, CH$_3$).

Preparation of 4-chloro-2-(4,4-dimethyl-4,5-dihydrooxazol-2-yl)-5-methoxyaniline 2h

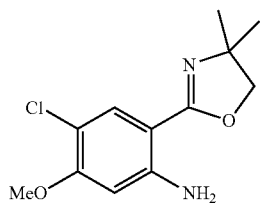 [SMILES: COc1cc(N)c(C2=NC(C)(C)CO2)cc1Cl]

Yellow solid (Yield 45%) $^1$H NMR (400 MHz, CDCl$_3$) δ 7.73 (s, 1H, Ar), 6.21 (s, 1H, Ar), 4.06 (s, 2H, CH$_2$), 3.87 (s, 3H, OCH$_3$), 1.41 (s, 6H, CH$_3$); HRMS (ESI) C$_{12}$H$_{16}$N$_2$O$_2$$^{35}$Cl [M+H]+ requires 255.0900, found 255.0891 (100%), C$_{12}$H$_{16}$N$_2$O$_2$$^{37}$Cl [M+H]+ requires 257.0871, found 257.0867. MS (CI+) 251.2 [M+H]$^+$.

Preparation of 2-(4,4-dimethyl-4,5-dihydrooxazol-2-yl)-4-fluoro-5-methoxyaniline 2i

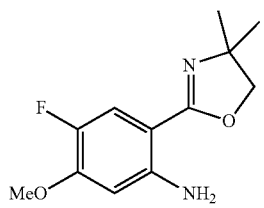 [SMILES: COc1cc(N)c(C2=NC(C)(C)CO2)cc1F]

Pale Yellow solid (Yield 52%) $^1$H NMR (400 MHz, CDCl$_3$) $δ_H$ 7.39 (d, J=12.4 Hz, 1H, Ar), 6.22 (d, J=7.3 Hz, 1H, Ar), 3.99 (s, 2H, CH$_2$), 3.86 (s, 3H, OCH$_3$), 1.36 (s, 6H, CH$_3$); $^{13}$C NMR (101 MHz, CDCl$_3$) $δ_C$ 161.88, 160.40, 151.42, 146.61, 116.23, 116.03, 99.93, 77.92, 68.10, 56.33 (OCH$_2$), 29.07 (CH$_3$); MS (CI+) 239.2 [M+H]$^+$.

General Procedure for the Preparation of Ketone 4

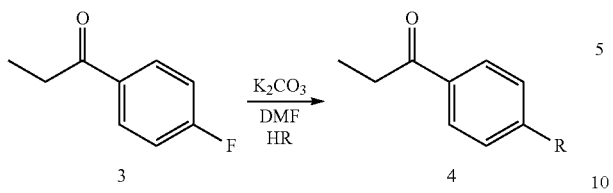

To a suspension of K$_2$CO$_3$ (0.50 g, 3.6 mmol) in DMF (5 ml), 4'-fluoropropiophenone (0.31 ml, 3.0 mmol) and amine HR (0.43 ml, 3.6 mmol) were added. The mixture was heated to 120° C. for overnight. After that, all DMF was removed in vacuo and the residue was dissolved in Et$_2$O. The insoluble was removed by filtration and the filtrate was concentrated in vacuo to give the crude product. The crude product was purified by flash column chromatograph eluting with 5~10% EtOAc in hexane to give the desired ketone.

The following compounds were prepared according to the general procedure described above.

Preparation of 1-(4-(piperidin-1-yl)phenyl)propan-1-one 4a

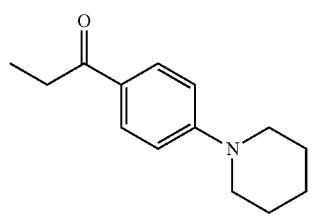 [SMILES: CCC(=O)c1ccc(N2CCCCC2)cc1]

Yellow solid (Yield 68%) $^1$H NMR (400 MHz, CDCl$_3$) δ$_H$ 8.08-7.81 (m, 2H, Ar), 6.97-6.80 (m, 2H, Ar), 3.49-3.27 (m, 4H, CH$_2$), 2.91 (q, J=7.3 Hz, 2H, CH$_2$), 1.80-1.63 (m, 6H, CH$_2$), 1.20 (t, J=7.3 Hz, 3H, CH$_3$); $^{13}$C NMR (101 MHz, CDCl$_3$) δhd C 199.58, 154.75, 130.48, 126.80, 113.76, 49.07, 31.46, 25.77, 24.76, 9.13. HRMS (CI) C$_{14}$H$_{19}$NO [M+H]+ requires 218.1539, found 218.1534.

Preparation of 1-(4-(4-(benzyloxy)piperidin-1-yl)phenyl)propan-1-one 4b

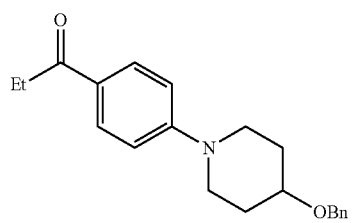 [SMILES: CCC(=O)c1ccc(N2CCC(OCc3ccccc3)CC2)cc1]

White solid (0.80 g, 65%). $^1$H NMR (400 MHz, CDCl$_3$) 7.88 (d, J=8.8 Hz, 2H), 7.35 (m, 5H), 6.87 (d, J=8.8 Hz, 2H), 4.59 (s, 2H), 3.68 (m, 3H), 3.15 (m, 2H), 2.91 (q, J=7.2 Hz, 2H), 2.00 (m, 2H), 1.77 (m, 2H), 1.20 (t, J=7.2 Hz, 3H); $^{13}$C NMR (100 MHz, CDCl$_3$) δ$_C$ 199.6, 169.5, 154.2, 139.1, 130.5, 128.8, 128.1, 127.9, 127.2, 114.0, 74.1, 70.3, 45.6, 31.5, 30.9, 9.1; MS (ES$^+$) m/z 323.2 (M+H)$^+$ Preparation of 1-(4-(3-methylpiperidin-1-yl)phenyl)propan-1-one 4c

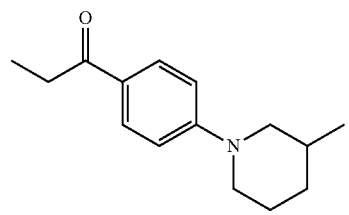 [SMILES: CCC(=O)c1ccc(N2CCCC(C)C2)cc1]

Yellow solid (0.58g, 84%). $^1$H NMR (400 MHz, CDCl$_3$) δ 7.87 (d, J=9.1 Hz, 2H), 6.85 (d, J=9.1 Hz, 2H), 3.86-3.72 (m, 2H), 2.91 (q, J=7.3 Hz, 2H), 2.81 (td, J=12.3, 3.1 Hz, 1H), 2.50 (dd, J=12.6, 10.7 Hz, 1H), 1.89-1.80 (m, 1H), 1.79-1.54 (m, 3H), 1.20 (t, J=7.3 Hz, 3H), 1.12 (ddd, J=23.7, 12.5, 4.1 Hz, 1H), 0.95 (d, J=6.6 Hz, 3H).

Preparation of (R)-1-(4-(3-methylpiperidin-1-yl)phenyl)propan-1-one 4d

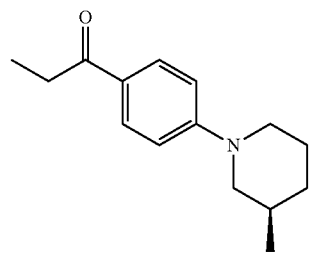 [SMILES: CCC(=O)c1ccc(N2CCC[C@@H](C)C2)cc1]

Pale yellow oil (74%). $^1$H NMR spectrum data is the same as the racemic analogue.

Preparation of (S)-1-(4-(3-methylpiperidin-1-yl)phenyl)propan-1-one 4e

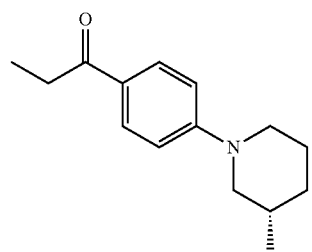

Pale yellow oil (75%). $^1$H NMR spectrum data is the same as the racemic analogue.

Preparation of 1-(4-(4-methylpiperidin-1-yl)phenyl)propan-1-one 4f

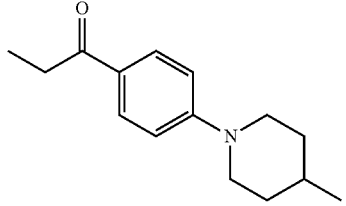 [SMILES: CCC(=O)c1ccc(N2CCC(C)CC2)cc1]

Pale yellow oil (73%). NMR: ¹H (400 MHz, CDC$l_3$) δ 7.87 (d, J=9.1 Hz, 2H), 6.86 (d, J=9.1 Hz, 2H), 3.87 (d, J=12.9 Hz, 2H), 2.96-2.79 (m, 4H), 1.73 (d, J=15.5 Hz, 2H), 1.68-1.53 (m, 1H), 1.28 (ddd, J=16.4, 12.8, 4.1 Hz, 2H), 1.20 (t, J=7.3 Hz, 3H), 0.97 (d, J=6.5 Hz, 3H).

Preparation of (R)-1-(4-(3-fluoropyrrolidin-1-yl)phenyl)propan-1-one 4g

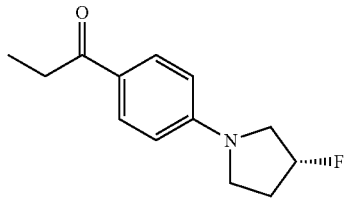 [SMILES: CCC(=O)c1ccc(N2CC[C@@H](F)C2)cc1]

Pale yellow oil (38%). NMR: ¹H (400 MHz, CDCl$_3$) δ 7.91 (d, J=8.9 Hz, 2H), 6.54 (d, J=8.9 Hz, 2H), 5.41 (d, J=53.9 Hz, 1H), 3.67 (d, J=2.1 Hz, 1H), 3.65-3.50 (m, 3H), 2.92 (q, J=7.3 Hz, 2H), 2.49-2.36 (m, 1H), 2.28-2.06 (m, 1H), 1.21 (t, J=7.3 Hz, 3H).

Preparation of (S)-1-(4-(3-fluoropyrrolidin-1-yl)phenyl)propan-1-one 4h

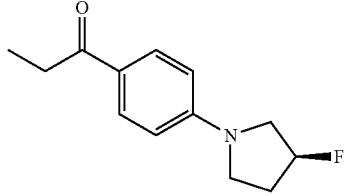 [SMILES: CCC(=O)c1ccc(N2CC[C@H](F)C2)cc1]

Pale yellow oil (37%). NMR: ¹H (400 MHz, CDCl$_3$) δ 7.91 (d, J=8.9 Hz, 2H), 6.54 (d, J=8.9 Hz, 2H), 5.41 (d, J=53.9 Hz, 1H), 3.67 (d, J=2.1 Hz, 1H), 3.65-3.50 (m, 3H), 2.92 (q, J=7.3 Hz, 2H), 2.49-2.36 (m, 1H), 2.28-2.06 (m, 1H), 1.21 (t, J=7.3 Hz, 3H).

Preparation of 1-(4-(3,3-difluoroazetidin-1-yl)phenyl)propan-1-one 4i

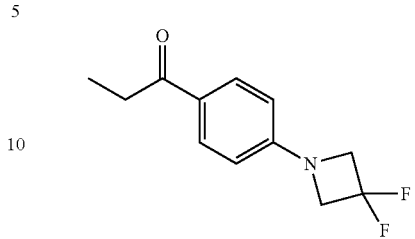

Pale yellow oil (25%). NMR: ¹H (400 MHz, CDCl$_3$) δ 7.91 (d, J=8.8 Hz, 2H), 6.47 (d, J=8.8 Hz, 1H), 4.32 (t, J=11.7 Hz, 2H), 2.93 (q, J=7.3 Hz, 1H), 1.21 (t, J=7.3 Hz, 2H).

Preparation of 1-(4-(3-hydroxy-3-methylpiperidin-1-yl)phenyl)propan-1-one 4j

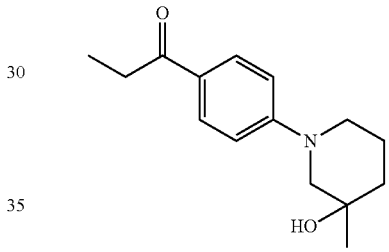

Yellow oil (69%). NMR: ¹H (400 MHz, CDCl$_3$) δ 7.90 (d, J=9.0 Hz, 2H), 6.95 (d, J=9.0 Hz, 2H), 3.66 (d, J=12.1 Hz, 1H), 3.49 (d, J=12.3 Hz, 1H), 3.01-2.80 (m, 4H), 2.44 (s, 1H), 2.00-1.84 (m, 1H), 1.84-1.70 (m, 2H), 1.58-1.48 (m, 1H), 1.31 (s, 3H), 1.23 (t, J=7.3 Hz, 3H).

Preparation of 1-(4-(3-hydroxy-3-methylpyrrolidin-1-yl)phenyl)propan-1-one 4k

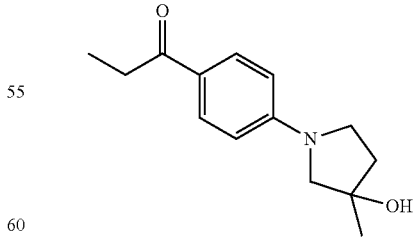

Yellow oil (54%). NMR: ¹H (400 MHz, CDCl$_3$) δ 7.86 (d, J=8.9 Hz, 2H), 6.50 (d, J=8.9 Hz, 2H), 3.60 (dd, J=16.6, 9.2 Hz, 1H), 3.50-3.41 (m, 1H), 3.35 (q, J=10.4 Hz, 2H), 2.87 (q, J=7.3 Hz, 2H), 2.14-1.96 (m, 2H), 1.59 (b, 1H), 1.50 (s, 3H), 1.20 (t, J=7.3 Hz, 3H).

Preparation of 1-(4-(4-fluoropiperidin-1-yl)phenyl)propan-1-one 4l

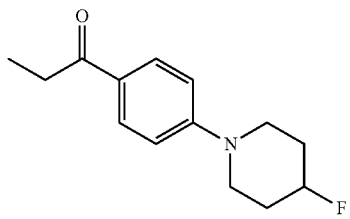 [SMILES: CCC(=O)c1ccc(N2CCC(F)CC2)cc1]

Brown solid (Yield 48%) $^1$H NMR (400 MHz, CDCl$_3$) δ 7.90 (d, J=8.9 Hz, 2H, Ar), 7.13-6.80 (m, 2H, Ar), 5.02-4.71 (m, 1H, CH), 3.66-3.48 (m, 2H, CH$_2$), 3.48-3.30 (m, 2H, CH$_2$), 2.93 (q, J=7.3 Hz, 2H, CH$_2$), 2.13-1.81 (m, 4H, CH$_2$), 1.21 (t, J=7.3 Hz, 3H, CH$_3$); $^{13}$C NMR (101 MHz, CDCl$_3$) δ 199.22 (C=O), 153.51, 130.13, 127.08, 113.67, 87.99 (d, J=171.3 Hz), 43.98 (d, J=5.6 Hz), 31.14, 30.61 (d, J=19.9 Hz), 8.65; MS (01+) 236.2 [M+H]+.

Preparation of 1-(4-morpholinophenyl)propan-1-one 4m

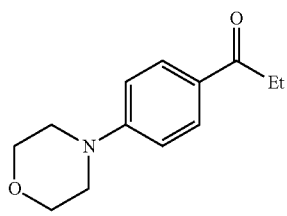 [SMILES: CCC(=O)c1ccc(N2CCOCC2)cc1]

Light cream solid (1.81 g, 88%). $^1$H NMR (400 MHz, CDCl$_3$) δ 7.91 (d, J=9.0 Hz, 2H), 6.88 (d, J=9.0 Hz, 2H), 3.87 (m, 4H), 3.31 (m, 4H), 2.91 (q, J=7.3 Hz, 2H), 1.20 (t, J=7.3 Hz, 3H); $^{13}$C NMR (100 MHz, CDCl$_3$) δ$_C$ 199.7, 169.5, 154.5, 130.4, 128.3, 113.8, 66.9, 48.1, 31.6, 9.0; MS (ES$^+$) m/z 219.1 (M+H)$^+$

Preparation of 1-(4-(4,4-difluoropiperidin-1-yl)phenyl)propan-1-one 4n

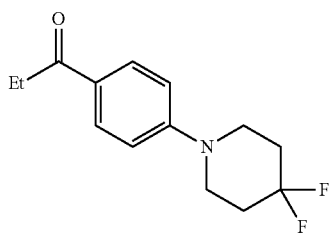 [SMILES: CCC(=O)c1ccc(N2CCC(F)(F)CC2)cc1]

Cream solid (0.50 g, 40%). $^1$H NMR (400 MHz, CDCl$_3$) 7.90 (d, J=8.8 Hz, 2H), 6.90 (d, J=8.8 Hz, 2H), 3.53 (m, 4H), 2.91 (q, J=7.2 Hz, 2H), 2.08 (m, 4H), 1.20 (t, J=7.2 Hz, 3H); MS (ES$^+$) m/z 254 (M+H)$^+$

Preparation of (S)-1-(4-(2-((benzyloxy)methyl)pyrrolidin-1-yl)phenyl)propan-1-one 4o

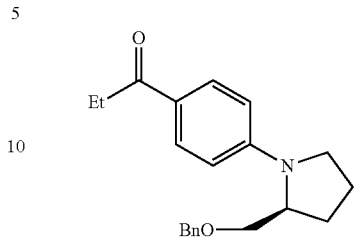

Cream solid (0.35 g, 41%). $^1$H NMR (400 MHz, CDCl$_3$) 7.88 (d, J=8.8 Hz, 2H), 7.37 (m, 5H), 6.59 (d, J=8.8 Hz, 2H), 4.55 (s, 2H), 4.04 (m, 1H), 3.61 (dd, J=8.8, 4.5 Hz, 1H), 3.50 (m, 1H), 3.35 (t, J=8.5 Hz, 1H), 3.25 (m, 1H), 2.93 (q, J=7.2 Hz, 2H), 2.10 (m, 4H), 1.23 (t, J=7.2 Hz, 3H); $^{13}$C NMR (100 MHz, DMSO) δ$_C$ 199.7, 150.9, 138.5, 130.8, 128.6, 128.1, 128.0, 125.4, 111.6, 58.6, 48.5, 31.4, 29.2, 23.5, 9.3; MS (ES+) m/z 346 (M+Na)$^+$ HRMS calculated for 346.1783 C$_{21}$H$_{25}$NO$_2{}^{23}$Na, found 346.1785.

Preparation of (S)-1-(4-(3-((benzylamino)methyl)pyrrolidin-1-yl)phenyl)propan-1-one 4p

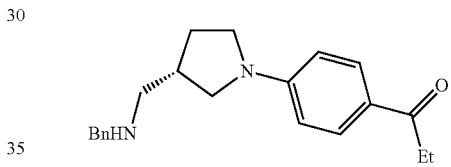

Light yellow oil. (0.55 g, 41%). $^1$H NMR (400 MHz, CDCl$_3$) 7.80 (d, J=8.8 Hz, 2H), 7.31 (m, 5H), 6.36 (d, J=8.8 Hz, 2H), 3.88 (m, 1H), 3.80 (d, J=10.0 Hz, 1H), 3.48 (d, J=10.0 Hz, 1H), 3.26 (m, 1H), 2.89 (q, J=7.6 Hz, 2H), 2.33-2.15 (m, 2H), 1.82 (m, 2H), 1.47 (m, 4H), 1.20 (t, J=7.6 Hz, 3H); $^{13}$C NMR (100 MHz, CDCl$_3$) δ$_C$ 199.5, 150.8, 139.9, 130.7, 129.4, 128.6, 127.6, 127.4, 127.1, 124.8, 111.5, 60.4, 59.6, 55.9, 48.3, 31.3, 29.4, 23.8, 22.6, 14.6, 9.3; MS (ES+) m/z 322 (M+H)$^+$ HRMS calculated for 322.2045 C$_{21}$H$_{26}$N$_2$O, found 322.2042.

Preparation of 1-(4-(3,4-difluoro-1H-pyrrol-1-yl)phenyl)propan-1-one 4q

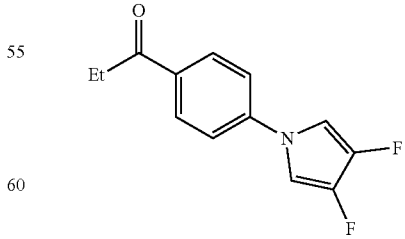

White solid (0.50g, 32%). $^1$H NMR (400 MHz, CDCl$_3$) 8.04 (d, J=8.8 Hz, 2H), 7.34 (d, J=8.8 Hz, 2H), 6.83 (s, 2H), 3.00 (q, J=7.2 Hz, 2H), 1.25 (t, J=7.2 Hz, 3H); $^{13}$C NMR (100 MHz, CDCl$_3$) δ$_C$ 199.7, 143.6, 142.8, 142.7, 140.3, 140.2, 134.5, 130.3, 119.0, 102.2, 102.1, 102.0, 101.9, 101.8, 101.7, 32.2, 8.6; MS (ES+) m/z 236.1 (M+H)$^+$ Other Ketone Procedures Preparation of 1-(4-(3,3-difluoropyrrolidin-1-yl)phenyl)propan-1-one 4r

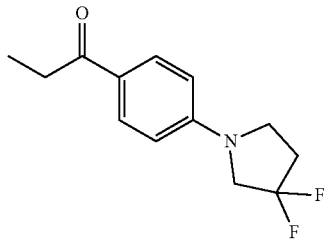 [SMILES: CCC(=O)c1ccc(N2CCC(F)(F)C2)cc1]

The mixture of 1-(4-iodophenyl)propan-1-one (0.94 g, 3.6 mmol), 3,3-difuolropyrrolidine hydrochloride (0.52 g, 3.6 mmol), Pd$_2$(dba)$_3$ (136 mg, 0.144 mmol), Xantphos (0.34 g, 0.58 mmol) and NaO$^t$Bu (1.07 g, 10.8 mmol) was degassed in a sealed-tube. After the addition of 1,4-dioxane (15 ml), the reaction mixture was degassed again, and then heated to 110° C. for 24 hours in the sealed-tube. After that, the reaction mixture was cooled to room temperature, and then filtered through a pad of silica. The silica pad was washed with 50% EtOAc in hexane. The filtrate and the washed down solution were combined and concentrated in vacuo to give the crude product. The crude product was purified by flash column chromatograph eluting with 20% EtOAc in hexane to give the title product as a colorless oil (0.24g, 28%). NMR: $^1$H (400 MHz, CDCl$_3$) δ 7.94 (d, J=8.9 Hz, 2H), 6.55 (d, J=8.9 Hz, 2H), 3.76 (t, J=13.0 Hz, 1H), 3.64 (t, J=7.2 Hz, 1H), 2.94 (q, J=7.3 Hz, 1H), 2.62-2.48 (m, 1H), 1.23 (t, J=7.3 Hz, 2H).

Preparation of 1-(4-(3,3-difluoropiperidin-1-yl)phenyl)propan-1-one 4s

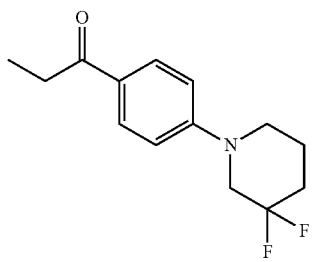 [SMILES: CCC(=O)c1ccc(N2CCCC(F)(F)C2)cc1]

Reaction, work-up and purification procedure followed similar reaction described for. The title product was isolated as a colorless oil (12%). NMR: $^1$H (400 MHz, CDCl$_3$) δ 7.89 (d, J=9.1 Hz, 2H), 6.89 (d, J=9.1 Hz, 2H), 3.56 (t, J=11.5 Hz, 2H), 3.43-3.35 (m, 2H), 2.93 (q, J=7.3 Hz, 2H), 2.15-2.00 (m, 2H), 1.96-1.84 (m, 2H), 1.21 (t, J=7.3 Hz, 3H).

Preparation of 4-iodo-1-(4-(trifluoromethoxy)benzyl)-1H-pyrazole 7a

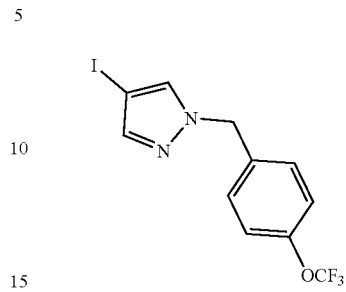

To a stirring suspension of 4-iodo-1H-pyrole (1.94 g, 10.0 mmol) and K$_2$CO$_3$ (3.46 g, 25 mmol) in acetone, 4-(trifluoromethoxy)benzyl bromide (1.71 ml, 20.5 mmol) is added. The resulting mixture is heated to reflux for 3 hours. After that, the reaction mixture is cooled to room temperature and filtered to remove the insoluble salt. The filtrate is concentrated to give the crude product as a pale yellow oil. The crude product is purified by flash column chromatograph eluting with 10-20% EtOAc in hexane to give the title product (3.6 g, ~99%) as a colorless oil.

Preparation of 4-iodo-1-(4-(trifluoromethoxy)phenethyl)-1H-pyrazole 7b

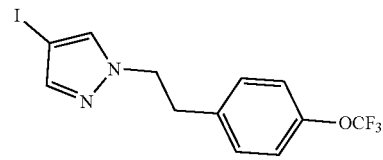 [SMILES: FC(F)(F)Oc1ccc(CCn2cc(I)cn2)cc1]

The reaction, work-up and purification procedure of title compound were followed similar procedure described previous in the preparation of 4-iodo-1-(4-(trifluoromethoxy)benzyl)-1H-pyrazole. The title product is given as a pale yellow solid in 65% yield. NMR: $^1$H (400 MHz, CDCl$_3$) δ 7.53 (s, 1H), 7.22 (s, 1H), 7.13 (d, J=8.0 Hz, 2H), 7.07 (d, J=8.7 Hz, 2H), 4.32 (t, J=7.2 Hz, 2H), 3.15 (t, J=7.2 Hz, 2H).

Preparation of 3-methyl-1-(1-(4-(trifluoromethoxy)benzyl)-1H-pyrazol-4-yl)butan-1-one 8a

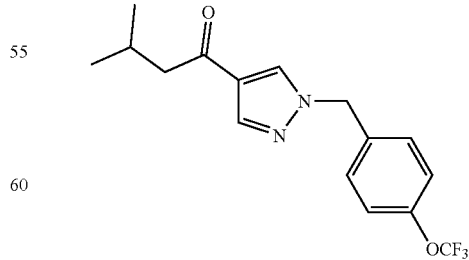

To a suspension of Pd$_2$(dba)$_3$, dppp and 4 Å M.S. in DMF, 4-iodo-1-(4-(trifluoromethoxy)benzyl)-1H-pyrazole, aldhyde and pyrrolidine are added. The resulting mixture is degassed and heated to 110° C. for 6 hours under N$_2$. After that, the reaction, mixture is diluted with 40% EtOAc in hexane (20 ml) and filtered through a pad of silica. The silica pad is washed with further 40% EtOAc in hexane (100 ml). After removed all solvents in the filtrate the crude product is given as a yellow oil. The crude product is purified by flash column chromatograph eluting with 40~60% EtOAc in hexane to give the title compound as a pale yellow solid in 55% yield. NMR: 1H (400 MHz, CDCl$_3$) δ 7.94 (s, 1H), 7.89 (s, 1H), 7.29 (d, J=8.8 Hz, 2H), 7.22 (d, J=8.6 Hz, 2H), 5.32 (s, 2H), 2.60 (d, J=7.0 Hz, 2H), 2.25 (dp, J=6.8, 6.7 Hz, 1H), 0.97 (d, J=6.7 Hz, 6H).

Preparation of 1-(1-(4-(trifluoromethoxy)phenethyl)-1H-pyrazol-4-yl)propan-1-one 8b

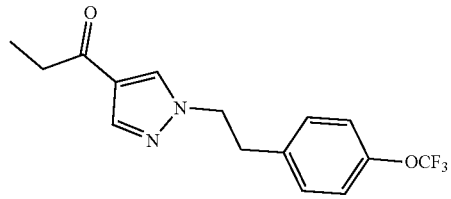 [SMILES: CCC(=O)c1cnn(CCc2ccc(OC(F)(F)F)cc2)c1]

The reaction, work-up and purification procedure of title compound were followed similar procedure described previous in the preparation of 3-methyl-1-(1-(4-(trifluoromethoxy)benzyl)-1H-pyrazol-4-yl)butan-1-one. The title product is given as a pale yellow solid in 26% yield. NMR: $^1$H (400 MHz, CDCl$_3$) δ 7.94 (s, 1H), 7.63 (s, 1H), 7.12 (d, J=8.7 Hz, 2H), 7.07 (d, J=8.7 Hz, 2H), 4.34 (t, J=7.1 Hz, 2H), 3.20 (t, J=7.1 Hz, 2H), 2.71 (q, J=7.4 Hz, 2H), 1.16 (t, J=7.4 Hz, 3H).

Procedure for the preparation of 1-(6-(4-(trifluoromethoxy)phenoxy)pyridin-3-yl)ethanone 12a

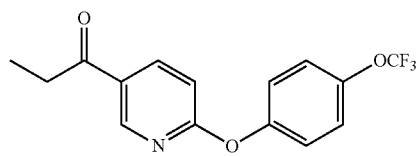 [SMILES: CCC(=O)c1ccc(Oc2ccc(OC(F)(F)F)cc2)nc1]

Pyridinium chlorochromate (30 mmol, 1.5 eq) was added to a solution of alcohol (20 mmol, 1.0 eq) in DCM (35 mL) and the resulting mixture was stirred under nitrogen at r.t. for 1-2 hours. The reaction was then diluted with ether (500 mL) and filtered through a silica pad. The filtrate was concentrated under vacuum to give the crude product as a clear colourless oil. Where necessary purification by column chromatography (eluting with 5%-10% EtOAc in hexane) gave the corresponding ketone. Yellow oil (Yield 72%). $^1$H NMR (400 MHz, CDCl$_3$), δH 8.75, (d, 1H, J=2.5 Hz, Ar), 8.29 (dd, 1H, J=8.7 Hz, 2.5 Hz, Ar), 7.29 (d, 2H, J=9.1 Hz, Ar), 7.19 (d, 2H, J=9.1 Hz, Ar), 7.05 (d, 1H, J=8.7 Hz, Ar), 2.58 (s, 3H, CH$_3$) $^{13}$C NMR (100 MHz, CDCl$_3$), δC 195.7, 169.5, 166.3, 151.8, 149.8, 146.6, 139.9, 128.9, 123.2, 122.9, 112.0, 26.9 MS (ES+), [M+H]$^+$ (100), 298.1, HRMS calculated for 298.0691 C$_{14}$H$_{11}$NO$_3$F$_3$, found 298.0696.

General Procedure for the Preparation of Quinolones 5 and 9

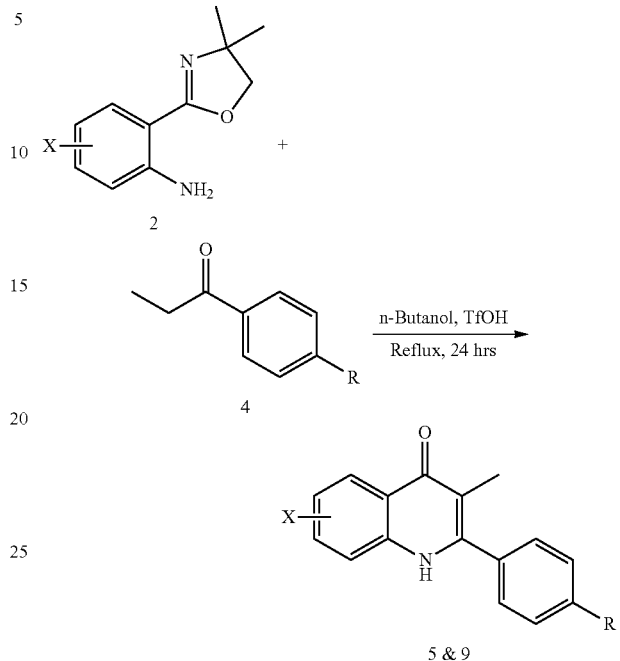

Oxazoline 2 (1.54 mmol) and ketone 4 (1.54 mmol) in anhydrous n-butanol (10 mL) were added trifluoromethanesulfonic acid (26 µL, 0.31 mmol, 0.2 equiv). The mixture was heated to 130° C. for 24 h (followed by tlc). The reaction was cooled and the solvent was removed under reduced pressure. Sat. NaHCO$_3$ (aq) was added and the resulting aqueous solution was extracted with ethyl acetate (×3), the combined organic layers were washed with water and brine, dried over MgSO$_4$, filtered and concentrated to a yellow solid. The crude product was triturated with diethyl ether to give the desired quinolone 5.

Preparation of 3-methyl-2-(4-(piperidin-1-yl)phenyl)quinolin-4(1H)-one (RKA-307) 5a

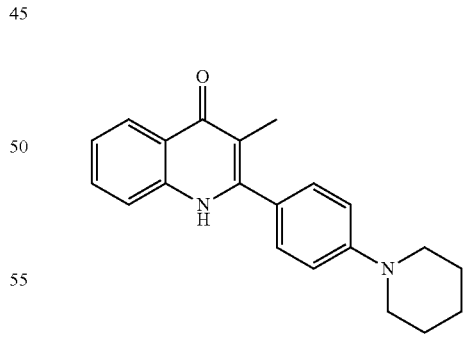

Light yellow powder (Yield 23%) m.p 290-292° C. $^1$H NMR (400 MHz, CDCl$_3$), δ$_H$ 8.46 (s, 1H, NH), 8.35 (d, 1H, J=8.1 Hz, Ar), 7.59-7.52 (m, 1H, Ar), 7.36 (d, 2H, J=8.7 Hz, Ar), 7.30 (dd, 2H, J=15.1 Hz, 7.2 Hz, Ar), 6.96 (d, 2H, J=8.7 Hz, Ar), 2.10 (3H.CH$_3$), 1.78-1.61 (m, 10H, CH$_2$) $^{13}$C NMR (100 MHz, CDCl$_3$), δ$_C$ 179.1, 152.9, 148.0, 139.4, 131.8, 129.9, 126.7, 125.5, 124.0, 123.5, 117.4, 116.5, 115.6, 50.0, 26.0, 13.0 MS (ES+), [M+Na]$^+$ (100), 319.2, HRMS calculated for 319.1810 C$_{21}$H$_{23}$N$_2$O, found 319.1808.

Preparation of 6-fluoro-3-methyl-2-(4-(piperidin-1-yl)phenyl)quinolin-4(1H)-one 5b

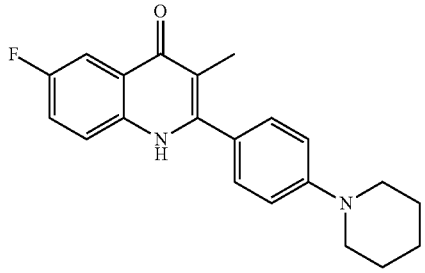 [SMILES: Cc1c(-c2ccc(N3CCCCC3)cc2)[nH]c2ccc(F)cc2c1=O]

Orange powder (Yield 26%) m.p 328-330° C. ¹H NMR (400 MHz, DMSO), $\delta_H$ 11.53 (s, 1H, NH), 7.71 (ddd, 1H, J=13.9 Hz, 9.3 Hz, 3.9 Hz, Ar), 7.51 (ddd, 1H, J 9.1 Hz, 8.4 Hz, 3.0 Hz, Ar), 7.38 (d, 2H, J=8.9 Hz, Ar), 7.07 (d, 2H, J=8.9 Hz, Ar), 3.30-3.26 (m, 4H, CH$_2$), 1.95 (s, 3H, CH$_3$), 1.66-1.55 (m, 6H, CH$_2$) ¹³C NMR (100 MHz, DMSO), $\delta_C$ 176.2, 157.1, 152.2, 148.6, 136.6, 130.2, 124.3, 121.2, 120.4, 115.0, 113.9,109.1, 49.1, 25.3, 24.3, 12.8 MS (ES+), [M+H]⁺ (100), 337.2, HRMS calculated for 337.1716 C$_{21}$H$_{22}$N$_2$OF, found 337.1728.

Preparation of 7-chloro-3-methyl-2-(4-(piperidin-1-yl)phenyl)quinolin-4(1H)-one 5c

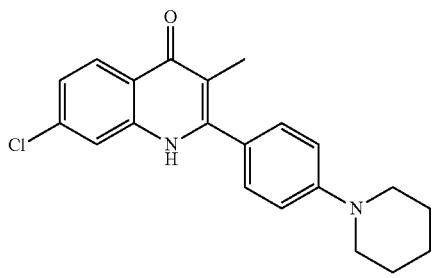 [SMILES: Cc1c(-c2ccc(N3CCCCC3)cc2)[nH]c2cc(Cl)ccc2c1=O]

Off white solid (0.17 g, 37%); mp 342-343° C.; ¹H NMR (400 MHz, DMSO) δ 8.08 (d, J=8.7 Hz, 1H), 7.59 (s, 1H), 7.40 (d, J=8.8 Hz, 2H), 7.18 (dd, J=8.7, 2.0 Hz, 1H), 7.04 (d, J=8.8 Hz, 2H), 3.08 (m, 4H), 1.95 (s, 3H), 1.61 (m, 6H); MS (ES+) m/z 353 (M+H)⁺ HRMS calculated for 353.1425 C$_{21}$H$_{22}$N$_2$O³⁵Cl, found 353.1421.

Preparation of 7-methoxy-3-methyl-2-(4-(piperidin-1-yl)phenyl)quinolin-4(1H)-one (RKA-310) 5d

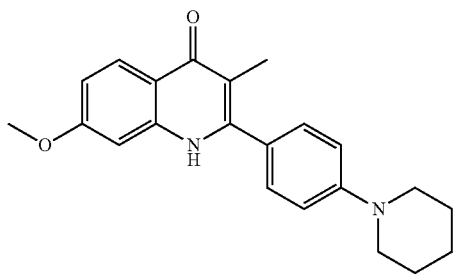 [SMILES: COc1ccc2c(=O)c(C)c(-c3ccc(N4CCCCC4)cc3)[nH]c2c1]

Orange powder (Yield 36%) m.p 278-280° C. ¹H NMR (400 MHz, CDCl$_3$), $\delta_H$ 10.09 (s, 1H, NH), 8.16 (d, 1H, J=8.5 Hz, Ar), 7.39 (d, 2H, J 0 8.9 Hz, Ar), 7.10 (d, 2H, J=8.9 Hz, Ar), 6.92 (dd, 2H, J=8.5 Hz, 2.6 Hz, Ar), 3.89 (s, 3H, OCH$_3$), 3.33-3.28 (m, 2H, CH$_2$), 2.06 (s, 3H, CH$_3$), 1.80-1.61 (m, 6H, CH$_2$) ¹³C NMR (100 MHz, CDCl$_3$), $\delta_C$ 176.4, 161.8, 152.8, 129.5, 126.5, 124.7, 115.3, 114.7, 114.3, 97.7, 54.7, 25.3, 24.1, 11.4 MS (ES+), [M+H]⁺ (100), 348.2, HRMS calculated for 348.1916 C$_{22}$H$_{26}$N$_3$O, found 348.2002.

Preparation of 5,7-difluoro-3-methyl-2-(4-(piperidin-1-yl)phenyOquinolin-4(1H)-one(MTD-403) 5e

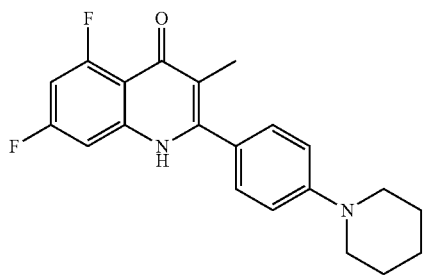 [SMILES: Cc1c(-c2ccc(N3CCCCC3)cc2)[nH]c2cc(F)cc(F)c2c1=O]

Off white solid (0.25 g, 35%); mp 305-306° C.; ¹H NMR (400 MHz, DMSO) $\delta_H$ 11.50 (bs, 1H), 7.37 (d, J=8.8 Hz, 2H), 7.15 (d, J=9.2 Hz, 1H), 7.08 (d, J=8.9 Hz, 2H), 6.98 (t, J=9.6 Hz, 1H), 3.30 (m, 4H), 1.88 (s, 3H), 1.61 (m, 6H); ¹³C NMR (100 MHz, CDCl$_3$) $\delta_C$ 175.2, 152.1, 148.6, 130.2, 116.1, 114.9, 100.2, 49.2, 25.3, 24.3, 12.6; MS (ES+) m/z 355 (M+H)⁺ HRMS calculated for 355.1622 C$_{21}$H$_{21}$N$_2$OF$_2$, found 355.1625.

Preparation of 6,7-dimethoxy-3-methyl-2-(4-(piperidin-1-yl)phenyl)quinolin-4(1H)-one 5f

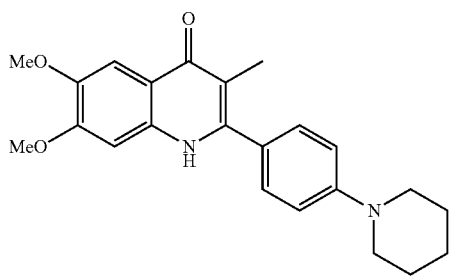 [SMILES: COc1cc2[nH]c(-c3ccc(N4CCCCC4)cc3)c(C)c(=O)c2cc1OC]

Very pale yellow solid (Yield 28%) ¹H NMR (400 MHz, DMSO) $\delta_H$ 11.24 (s, 1H, NH), 7.45 (s, 1H, Ar), 7.36 (d, J=8.8 Hz, 2H, Ar), 7.16-6.98 (m, 3H, Ar), 3.83 (s, 3H, OCH$_3$), 3.82 (s, 3H, OCH$_3$), 3.29-3.25 (m, 4H, CH$_2$), 1.93 (s, 3H, CH$_3$), 1.69-1.53 (m, 6H, CH$_2$); ¹³C NMR (101 MHz, DMSO) $\delta_C$ 175.90 (C=O), 152.89, 152.05, 146.82, 146.54, 135.51, 130.19, 124.73, 117.34, 114.98, 113.15, 104.50, 99.38, 55.86 (OCH$_3$), 55.79 (OCH$_3$), 49.20, 25.35, 24.32, 12.86 (CH$_3$); HRMS (ESI) C$_{23}$H$_{27}$N$_2$O$_3$ [M+H]⁺ requires 379.2022, found 379.2012 (100%). Anal. C$_{23}$H$_{26}$N$_2$O$_3$ requires C 72.99%, H 6.92%, N 7.40%, found C 71.98%, H 6.96%, N 6.96%.

Preparation of 5,7-dimethoxy-3-methyl-2-(4-(piperidin-1-yl)phenyl)quinolin-4(1H)-one 5g

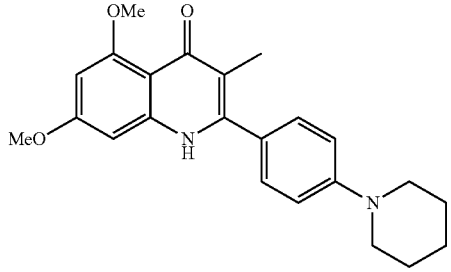 [SMILES: COc1cc(OC)c2c(=O)c(C)c(-c3ccc(N4CCCCC4)cc3)[nH]c2c1]

White solid (Yield 32%) $^1$H NMR (400 MHz, DMSO) $\delta_H$ 10.93 (s, 1H, NH), 7.33 (d, J=8.7 Hz, 2H, Ar), 7.05 (d, J=8.7 Hz, 2H, Ar), 6.64 (d, J=2.2 Hz, 1H, Ar), 6.25 (d, J=2.1 Hz, 1H, Ar), 3.78 (s, 3H, OCH$_3$), 3.77 (s, 3H, OCH$_3$), 3.32-3.11 (m, 4H, CH$_2$), 1.82 (s, 3H, CH$_3$), 1.70-1.48 (m, 6H, CH$_2$); $^{13}$C NMR (101 MHz, DMSO) $\delta_C$ 176.49 (C=O), 161.75, 161.03, 152.02, 145.53, 143.94, 130.15, 124.47, 115.49, 114.98, 109.24, 94.23, 91.57, 55.97 (OCH$_3$), 55.48 (OCH$_3$), 49.22, 25.35, 24.32, 12.82 (CH$_3$); HRMS (ESI) C$_{23}$H$_{27}$N$_2$O$_2$ [M+H]$^+$ requires 379.2022, found 379.2007. Anal. C$_{23}$H$_{26}$N$_2$O$_2$ requires C 72.99%, H 6.92%, N 7.40%, found C 72.13%, H 6.88%, N 7.03%. MP 264-265° C.

Preparation of 6-chloro-7-methoxy-3-methyl-2-(4-(piperidin-1-yl)phenyl)quinolin-4(1H)-one 5h

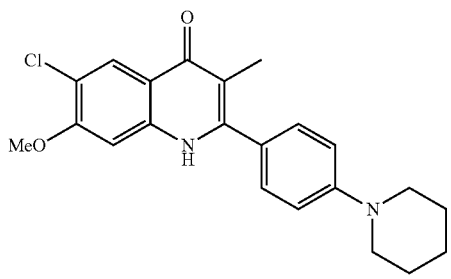 [SMILES: COc1cc2[nH]c(-c3ccc(N4CCCCC4)cc3)c(C)c(=O)c2cc1Cl]

White solid (Yield 35%) $^1$H NMR (400 MHz, DMSO) $\delta_H$ 11.42 (s, 1H, NH), 8.02 (s, 1H, Ar), 7.38 (d, J=8.8 Hz, 2H, Ar), 7.21 (s, 1H, Ar), 7.07 (d, J=8.9 Hz, 2H, Ar), 3.91 (s, 3H, OCH$_3$), 3.31-3.22 (m, 4H, CH$_2$), 1.93 (s, 3H, CH$_3$), 1.71-1.52 (m, 6H, CH$_2$); $^{13}$C NMR (101 MHz, DMSO) $\delta_C$ 175.63 (C=O), 156.74, 152.17, 148.16, 140.13, 130.21, 126.09, 124.18, 118.08, 117.91, 114.89, 114.25, 100.13, 56.59 (OCH$_3$), 49.10, 25.32, 24.32, 12.70 (CH$_3$); HRMS (ESI) C$_{22}$H$_{24}$N$_2$O$_2$$^{35}$Cl [M+H]$^+$ requires 383.1526, found 383.1513 (100%), C$_{22}$H$_{24}$N$_2$O$_2$$^{37}$Cl [M+H]$^+$ requires 385.1497, found 385.1501 (34%). MP >300° C. Anal. C$_{22}$H$_{23}$N$_2$O$_2$Cl requires C 69.01%, H 6.05%, N 7.32%, found C 68.98%, H 6.04%, N 7.23%.

Preparation of 6-fluoro-7-methoxy-3-methyl-2-(4-(piperidin-1-yl)phenyl)quinolin-4(1H)-one 5i

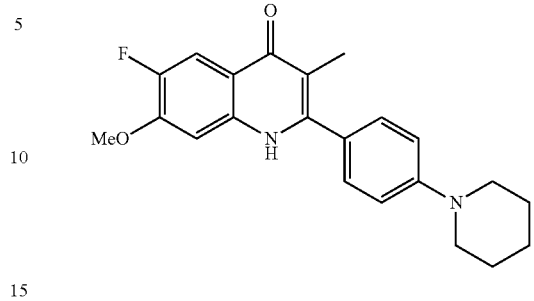

White solid (Yield 41%) $^1$H NMR (400 MHz, DMSO) $\delta_H$ 11.39 (s, 1H, NH), 7.71 (d, J=11.9 Hz, 1H, Ar), 7.37 (d, J=8.7 Hz, 2H, Ar), 7.24 (d, J=7.5 Hz, 1H, Ar), 7.07 (d, J=8.8 Hz, 2H, Ar), 3.90 (s, 3H, OCH$_3$), 3.30-3.19 (m, 4H, CH$_2$), 1.92 (s, 3H, CH$_3$), 1.74-1.48 (m, 6H, CH$_2$); $^{13}$C NMR (101 MHz, DMSO) $\delta_C$ 175.94 (C=O), 152.15, 151.00, 150.87, 150.35, 147.88, 137.55, 130.20, 124.30, 114.93, 113.57, 110.03, 101.12, 56.36 (OCH$_3$), 49.13, 25.33, 24.32, 12.70 (CH$_3$); HRMS (ESI) C$_{22}$H$_{24}$N$_2$O$_2$F [M+H]$^+$ requires 367.1822, found 367.1818. Anal. C$_{22}$H$_{23}$N$_2$O$_2$F requires C 72.11%, H 6.33%, N 7.64%, found C 71.95%, H 6.45%, N 7.37%.

Preparation of 2-(4-(4-(benzyloxy)piperidin-1-yl)phenyl)-5,7-difluoro-3-methylquinolin-4(1H)-one 5j

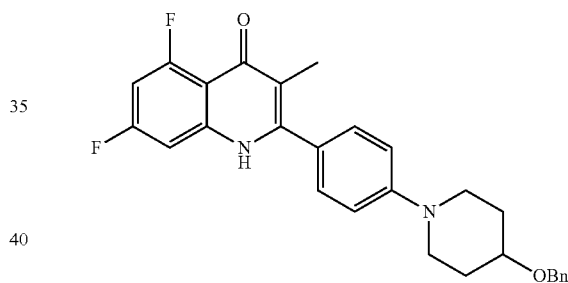

Cream solid (0.10 g, 20%). $^1$H NMR (400 MHz, DMSO) 7.37 (d, J=8.8 Hz, 2H), 7.35 (m, 4H), 7.29 (m, 1H), 7.14 (m, 1H), 7.10 (d, J=8.8 Hz, 2H), 6.97 (m, 1H), 4.57 (s, 2H), 3.65 (m, 3H), 3.05 (m, 2H), 1.99 (m, 2H), 1.99 (s, 3H), 1.62 (m, 2H); $^{13}$C NMR (100 MHz, DMSO) $\delta_C$ 175.3, 151.5, 139.4, 130.2, 128.6, 127.7, 127.6, 116.2, 114.9, 73.9, 69.2, 56.4, 30.6, 18.9, 12.6; MS (ES$^+$) m/z 461 (M+H)+HRMS calculated for 461.2041 C$_{28}$H$_{27}$N$_2$O$_2$F$_2$, found 461.2042.

Preparation of 5,7-difluoro-3-methyl-2-(4-(3-methylpiperidin-1-yl)phenyl)quinolin-4(1H)-one 5k

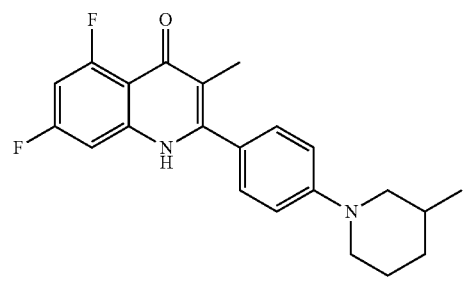 [SMILES: Cc1c(-c2ccc(N3CCCC(C)C3)cc2)[nH]c2cc(F)cc(F)c2c1=O]

White solid (45%). Melting point: 280~282° C. NMR: $^1$H (400 MHz, DMSO) δ 11.50 (s, 1H), 7.36 (d, J=8.8 Hz, 2H), 7.16 (d, J=9.0 Hz, 1H), 7.07 (d, J=8.9 Hz, 2H), 7.00 (ddd, J=12.0, 9.6, 2.4 Hz, 1H), 3.77 (t, J=11.6 Hz, 2H), 2.72 (td, J=12.3, 2.9 Hz, 1H), 2.42 (dd, J=12.4, 10.7 Hz, 1H), 1.87 (s, 3H), 1.82-1.48 (m, 4H), 1.09 (ddd, J=23.5, 12.4, 3.9 Hz, 1H), 0.93 (d, J=6.6 Hz, 3H). $^{13}$C (101 MHz, DMSO) δ 175.37, 164.10, 161.50, 152.00, 147.66, 142.69, 130.22, 123.46, 116.33, 114.81, 110.59, 99.40, 98.79, 55.93, 48.45, 32.93, 30.35, 24.72, 19.58, 12.50. ES HRMS: m/z found 369.1772, $C_{22}H_{23}N_2OF_2$ requires 369.1778.

Preparation of (R)-5,7-difluoro-3-methyl-2-(4-(3-methylpiperidin-1-yl)phenyOquinolin-4(1H)-one 5l

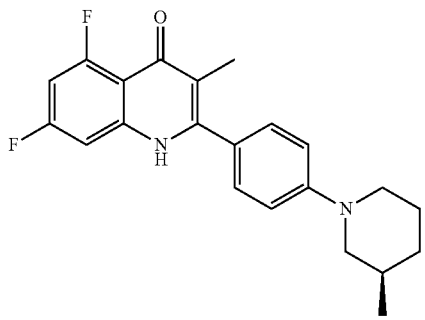 [SMILES: Cc1c(-c2ccc(N3CCC[C@@H](C)C3)cc2)[nH]c2cc(F)cc(F)c2c1=O]

White solid (43%). Analytical data is the same as the racemic analogue.

Preparation of (S)-5,7-difluoro-3-methyl-2-(4-(3-methylpiperidin-1-yl)phenyOquinolin-4(1H)-one 5m

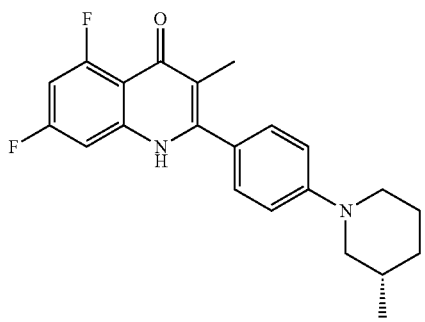 [SMILES: Cc1c(-c2ccc(N3CCC[C@H](C)C3)cc2)[nH]c2cc(F)cc(F)c2c1=O]

White solid (40%). Analytical data is the same as the racemic analogue.

Preparation of 5,7-difluoro-3-methyl-2-(4-(4-methylpiperidin-1-yl)phenyl)quinolin-4(1H)-one 5n

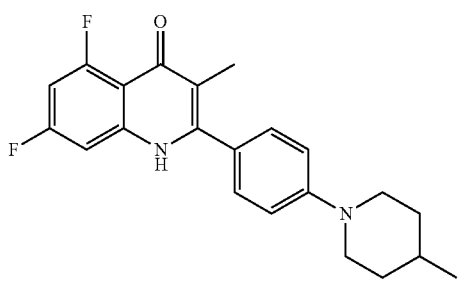 [SMILES: Cc1c(-c2ccc(N3CCC(C)CC3)cc2)[nH]c2cc(F)cc(F)c2c1=O]

White solid (54%). Melting point: decomposed at 310° C. NMR: $^1$H (400 MHz, DMSO) δ 11.50 (s, 1H), 7.36 (d, J=8.8 Hz, 2H), 7.16 (d, J=10.0 Hz, 1H), 7.08 (d, J=8.9 Hz, 2H), 7.00 (ddd, J=12.0, 9.6, 2.4 Hz, 1H), 3.83 (d, J=12.8 Hz, 2H), 2.76 (td, J=12.5, 2.4 Hz, 2H), 1.87 (s, 3H), 1.70 (d, J=12.7 Hz, 2H), 1.63-1.49 (m, 1H), 1.21 (qd, J=12.7, 4.0 Hz, 2H), 0.94 (d, J=6.5 Hz, 3H); $^{13}$C (101 MHz, DMSO) δ 175.37, 163.51, 160.76, 152.01, 147.65, 142.84, 130.21, 123.60, 116.33, 114.91, 110.49, 99.41, 98.81, 48.41, 33.55, 30.65, 22.18, 12.51. ES HRMS: m/z found 369.1792, $C_{22}H_{23}N_2OF_2$ requires 369.1778.

Preparation of (R)-5,7-difluoro-2-(4-(3-fluoropyrrolidin-1-yl)phenyl)-3-methylquinolin-4(1H)-one 5o

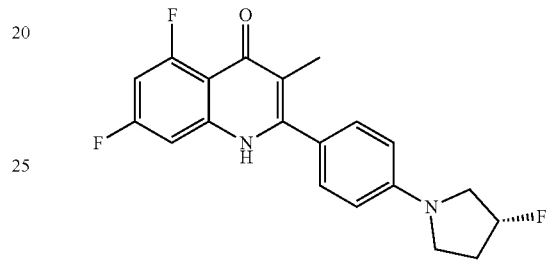

White solid (45%). Melting point: 313~314° C. NMR: $^1$H (400 MHz, DMSO) δ 11.47 (s, 1H), 7.38 (d, J=8.7 Hz, 2H), 7.18 (d, J=9.3 Hz, 1H), 6.99 (ddd, J=12.0, 9.6, 2.4 Hz, 1H), 6.73 (d, J=8.7 Hz, 2H), 5.50 (d, J=54.1 Hz, 1H), 3.71-3.36 (m, 4H), 2.38-2.12 (m, 2H), 1.89 (s, 3H); $^{13}$C (101 MHz, DMSO) δ 175.38, 148.31, 147.92, 142.70, 130.35, 121.60, 116.19, 111.70, 110.56, 99.39, 98.76, 94.49, 92.78, 54.48, 45.59, 32.14, 31.93, 12.58. ES HRMS: m/z found 359.1385, $C_{20}H_{18}N_2OF_3$ requires 359.1371.

Preparation of (S)-5,7-difluoro-2-(4-(3-fluoropyrrolidin-1-yl)phenyl)-3-methylquinolin-4(1H)-one 5p

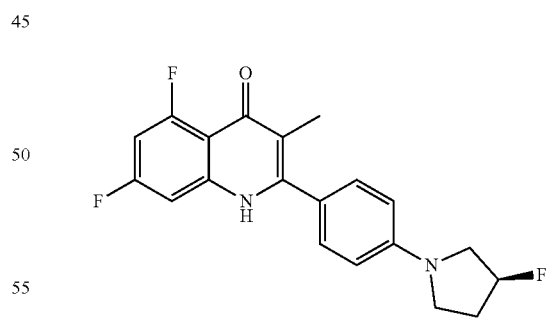

White solid (47%). Melting point: 313~314° C. NMR: $^1$H (400 MHz, DMSO) δ 11.47 (s, 1H), 7.38 (d, J=8.6 Hz, 2H), 7.18 (d, J=9.2 Hz, 1H), 6.99 (ddd, J=12.0, 9.7, 2.4 Hz, 1H), 6.73 (d, J=8.7 Hz, 2H), 5.50 (d, J=54.3 Hz, 1H), 3.69-3.36 (m, 4H), 2.36-2.13 (m, 2H), 1.89 (s, 3H); $^{13}$C (101 MHz, DMSO) δ 175.38, 148.32, 147.93, 142.78, 130.36, 121.60, 116.19, 111.70, 110.54, 99.36, 98.76, 94.49, 92.78, 54.48, 45.59, 32.14, 31.93, 12.58. ES HRMS: m/z found 359.1381, $C_{20}H_{18}N_2OF_3$ requires 359.1371.

Preparation of 2-(4-(3,3-difluoroazetidin-1-A phenyl)-5,7-difluoro-3-methylquinolin-4(1H)-one 5q

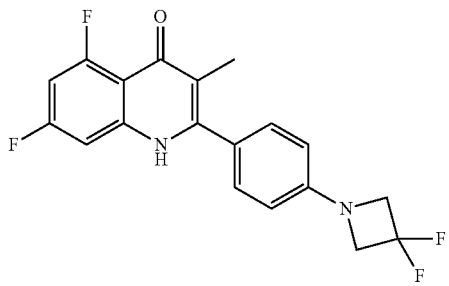 [SMILES: Cc1c(-c2ccc(N3CC(F)(F)C3)cc2)[nH]c2cc(F)cc(F)c2c1=O]

White solid (33%). Melting point: 316-318° C. NMR: $^1$H (400 MHz, DMSO) δ 11.54 (s, 1H), 7.43 (d, J=8.4 Hz, 2H), 7.16 (d, J=9.6 Hz, 1H), 7.01 (t, J=10.8 Hz, 1H), 6.74 (d, J=8.5 Hz, 2H), 4.37 (t, J=12.3 Hz, 4H), 1.86 (s, 3H).; $^{13}$C (101 MHz, DMSO) δ 175.39, 150.88, 147.53, 142.81, 130.18, 124.67, 117.01, 116.50, 112.70, 110.53, 99.41, 98.90, 90.56, 74.81, 63.29, 12.44. ES HRMS: m/z found 363.1130, $C_{19}H_{15}N_2OF_4$ requires 363.1121.

Preparation of 5,7-difluoro-2-(4-(3-hydroxy-3-methylpiperidin-1-yl)phenyl)-3-methylquinolin-4(1H)-one 5r

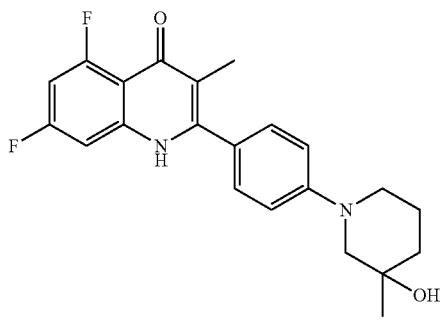 [SMILES: Cc1c(-c2ccc(N3CCCC(C)(O)C3)cc2)[nH]c2cc(F)cc(F)c2c1=O]

While solid (48%). Melting point: decomposed at 284° C. NMR: $^1$H (400 MHz, DMSO) δ 11.47 (s, 1H), 7.35 (d, J=8.8 Hz, 2H), 7.16 (d, J=9.2 Hz, 1H), 7.07-6.94 (m, 3H), 4.46 (s, 1H), 3.30-3.02 (m, 4H), 1.88 (s, 3H), 1.86-1.75 (m, 1H), 1.63-1.48 (m, 3H), 1.17 (s, 3H); $^{13}$C (101 MHz, DMSO) δ 175.37, 163.50, 161.49, 152.33, 147.68, 142.79, 130.15, 123.19, 116.27, 114.64, 110.56, 99.34, 98.82, 67.64, 59.76, 47.81, 37.73, 27.28, 22.10, 12.52. ES HRMS: m/z found 385.1738, $C_{22}H_{23}N_2O_2F_2$ requires 385.1728.

Preparation of 5,7-difluoro-2-(4-(3-hydroxy-3-methylpyrrolidin-1-yl)phenyl)-3-methylquinolin-4(1H)-one 5s

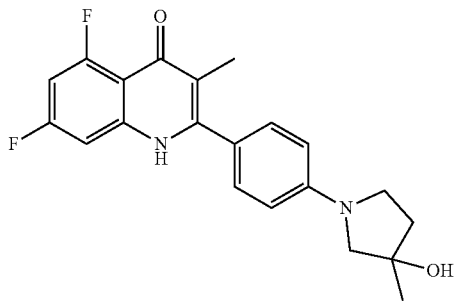 [SMILES: Cc1c(-c2ccc(N3CCC(C)(O)C3)cc2)[nH]c2cc(F)cc(F)c2c1=O]

White solid (50%). Melting point: 288-290° C. NMR: $^1$H (400 MHz, DMSO) δ 11.43 (s, 1H), 7.35 (d, J=8.7 Hz, 2H), 7.18 (d, J=10.1 Hz, 1H), 6.98 (ddd, J=12.0, 9.6, 2.5 Hz, 1H), 6.62 (d, J=8.8 Hz, 2H), 4.85 (s, 1H), 3.48-3.36 (m, 2H), 3.24 (s, 2H), 2.01-1.92 (m, 2H), 1.89 (s, 3H), 1.37 (s, 3H); $^{13}$C (101 MHz, DMSO) δ 175.38, 160.89, 155.31, 148.73, 148.07, 130.29, 120.65, 116.06, 111.02, 99.38, 96.34, 94.24, 91.71, 75.74, 60.95, 55.28, 46.88, 26.29, 12.63. ES HRMS: m/z found 399.1391, $C_{21}H_{20}N_2O_2F_2{}^{23}Na$ requires 393.1391.

Preparation of 2-(4-(3,3-difluoropyrrolidin-1-yl)phenyl)-5,7-difluoro-3-methylquinolin-4(1H)-one 5t

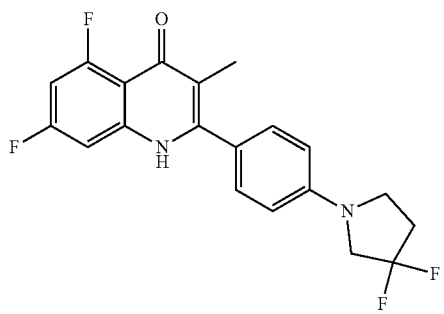 [SMILES: Cc1c(-c2ccc(N3CCC(F)(F)C3)cc2)[nH]c2cc(F)cc(F)c2c1=O]

White solid (56%). Melting point: decomposed at 316° C. NMR: $^1$H (400 MHz, DMSO) δ 7.41 (d, J=8.7 Hz, 2H), 7.17 (d, J=9.0 Hz, 1H), 7.01 (ddd, J=12.0, 9.6, 2.4 Hz, 1H), 6.78 (d, J=8.8 Hz, 2H), 3.79 (t, J=13.3 Hz, 1H), 3.56 (t, J=7.2 Hz, 1H), 2.59 (tt, J=14.5, 7.3 Hz, 1H), 1.87 (s, 1H); $^{13}$C (101 MHz, DMSO) δ 175.38, 164.09, 148.09, 147.72, 142.82, 130.34, 129.16, 126.71, 122.79, 116.32, 111.98, 111.61, 99.37, 98.82, 54.96, 45.75, 33.72, 12.54. ES HRMS: m/z found 399.1093, $C_{20}H_{16}N_2OF_4{}^{23}Na$ requires 399.1096.

Preparation of 2-(4-(3,3-difluoropiperidin-1-A phenyl)-5,7-difluoro-3-methylquinolin-4(1H)-one 5u

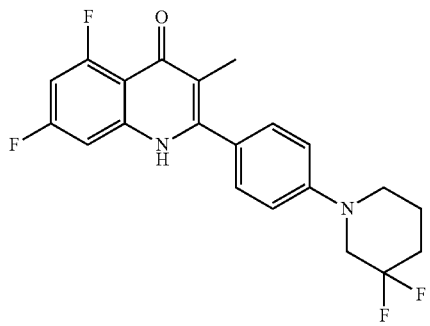 [SMILES: Cc1c(-c2ccc(N3CCCC(F)(F)C3)cc2)[nH]c2cc(F)cc(F)c2c1=O]

White solid (47%). Melting point: decomposed at 297° C. NMR: $^1$H (400 MHz, DMSO) δ 11.54 (s, 1H), 7.39 (d, J=8.8 Hz, 2H), 7.20-7.11 (m, 3H), 7.01 (ddd, J=12.0, 9.6, 2.4 Hz, 1H), 3.65 (t, J=11.9 Hz, 2H), 3.43-3.37 (m, 2H), 2.16-2.01 (m, 2H), 1.87 (s, 3H), 1.85-1.75 (m, 2H); $^{13}$C (101 MHz, DMSO) δ 175.38, 152.75, 150.88, 147.47, 142.69, 130.26, 124.51, 121.44, 116.43, 115.09, 113.88, 110.51, 99.67, 98.87, 53.21, 52.92, 46.93, 32.09, 21.59, 12.47. ES HRMS: m/z found 391.1441, $C_{21}H_{16}N_2OF_4$ requires 391.1434.

Preparation of 2-(4-(4-fluoropiperidin-1-yl)phenyl)-7-methoxy-3-methylquinolin-4(1H)-one 5v

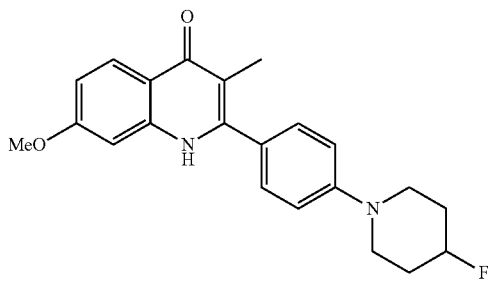 [SMILES: COc1ccc2c(=O)c(C)c(-c3ccc(N4CCC(F)CC4)cc3)[nH]c2c1]

Yellow solid (Yield 43%) ¹H NMR (400 MHz, DMSO) δ 11.26 (s, 1H, NH), 8.00 (d, J=8.9 Hz, 1H, Ar), 7.39 (d, J=8.6 Hz, 2H, Ar), 7.12 (d, J=8.6 Hz, 2H, Ar), 7.05 (d, J=2.1 Hz, 1H, Ar), 6.88 (dd, J=8.9, 2.2 Hz, 1H, Ar), 5.02-4.77 (m, 1H, CH), 3.82 (s, 3H, OCH₃), 3.57-3.44 (m, 2H, CH₂), 3.32-3.20 (m, 2H, CH₂), 2.13-1.95 (m, 2H, CH₂), 1.91 (s, 3H, CH₃), 1.86-1.71 (m, 2H, CH₂); ¹³C NMR (101 MHz, DMSO) δ 176.78 (C=O), 161.89, 151.28, 147.80, 141.66, 130.39, 127.22, 125.12, 117.98, 115.22, 114.02, 113.14, 99.23, 89.01 (d, J=169.4 Hz, C-F), 55.74, 44.87 (d, J=6.8 Hz), 30.84 (d, J=19.0 Hz), 12.78 (CH₃); HRMS (ESI) C₂₂H₂₄N₂O₂F [M+H]+ requires 367.1822, found 367.1836. Anal. C₂₂H₂₃N₂O₂F requires C 72.11%, H 6.33%, N 7.64%, found C 71.32%, H 6.34%, N 7.46%.

Preparation of 5,7-difluoro-3-methyl-2-(4-morpholinophenyl)quinolin-4(1H)-one 5w

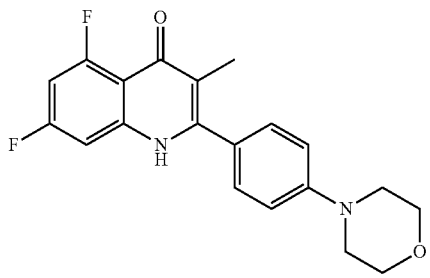 [SMILES: Cc1c(-c2ccc(N3CCOCC3)cc2)[nH]c2cc(F)cc(F)c2c1=O]

Off white solid (0.064 g, 25%); mp >370° C.; ¹H NMR (400 MHz, DMSO) δ 11.53 (bs, 1H), 7.40 (d, J=8.8 Hz, 2H), 7.12 (m, 1H), 7.09 (d, J=8.8 Hz, 2H), 6.92 (dd, J=11.0, 10.6 Hz, 1H), 3.77 (m, 4H), 3.21 (m, 4H), 1.87 (s, 3H); ¹³C NMR (100 MHz, DMSO) δ_C 178.2, 151.8, 130.2, 116.1, 114.6, 66.4, 48.3, 12.8; MS (ES⁺) m/z 355 (M+H)⁺ HRMS calculated for 357.1415 C₂₀H₁₉N₂O₂F₂, found 357.1410.

Preparation of 2-(4-(4,4-difluoropiperidin-1-yl)phenyl)-5,7-difluoro-3-methylquinolin-4(1H)-one 5x

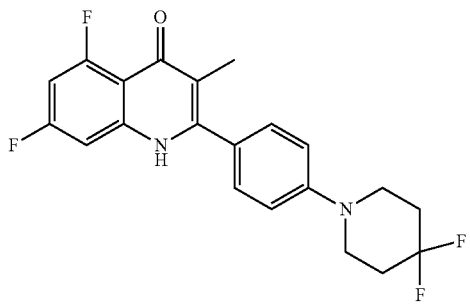 [SMILES: Cc1c(-c2ccc(N3CCC(F)(F)CC3)cc2)[nH]c2cc(F)cc(F)c2c1=O]

White solid (0.30 g, 57%). ¹H NMR (400 MHz, DMSO) 7.38 (d, J=8.8 Hz, 2H), 7.10 (d, J=8.8 Hz, 2H), 7.07 (m, 1H), 6.82 (dd, J=11.0, 10.6 Hz, 1H), 3.43 (m, 4H), 2.07 (m, 4H), 1.88 (s, 3H); ¹³C NMR (100 MHz, DMSO) δ_C 174.2, 149.5, 129.9, 122.8, 118.5, 115.3, 115.0, 45.3, 33.0, 32.8, 32.5, 12.6; MS (Cl⁺) m/z 391 (M+H)⁺ HRMS calculated for 391.1428 C₂₁H₁₈N₂OF₄, found 391.1430.

Preparation of (S)-2-(4-(2-((benzyloxy)methyl)pyrrolidin-1-yl)phenyl)-5,7-difluoro-3-methylquinolin-4(1H)-one 5y

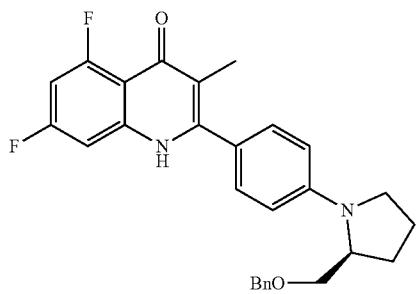 [SMILES: Cc1c(-c2ccc(N3CCC[C@H]3COCc3ccccc3)cc2)[nH]c2cc(F)cc(F)c2c1=O]

Cream solid (0.10 g, 20%). ¹H NMR (400 MHz, DMSO) δ_H 10.60 (bs, 1H), 7.33 (m, 6H), 7.22 (d, J=8.8 Hz, 2H), 6.56 (dd, J=11.0, 10.6 Hz, 1H), 6.44 (d, J=8.8 Hz, 2H), 4.52 (s, 2H), 3.84 (m, 1H), 3.51 (dd, J=8.8, 4.5 Hz, 1H), 3.30 (m, 2H), 3.05 (m, 1H), 2.05 (m, 4H), 1.92 (s, 3H); ¹³C NMR (100 MHz, DMSO) δ_C 177.1, 148.8, 147.9, 138.1, 129.7, 128.4, 127.8, 127.6, 121.5, 117.2, 111.3, 99.2, 73.4, 70.0, 58.2, 48.3, 28.9, 23.2, 12.4; MS (ES+) m/z 461 (M+H)⁺ HRMS calculated for 461.2041 C₂₈H₂₇N₂O₂F₂, found 461.2055.

Preparation of (R)-2-(4-(3-((benzylamino)methyl)pyrrolidin-1-yl)phenyl)-5,7-difluoro-3-methylquinolin-4(1H)-one 5z

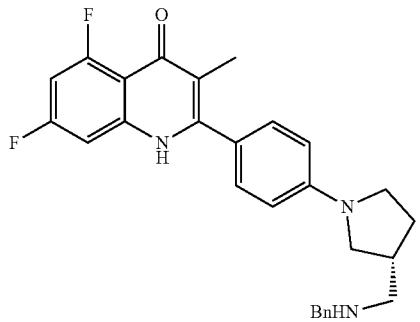

White solid (0.15 g, 37%). ¹H NMR (400 MHz, DMSO) δ_H 9.28 (bs, 1H), 7.39-7.23 (m, 5H), 7.16 (d, J=8.8 Hz, 2H), 6.99 (d, J=8.4 Hz, 1H), 6.58 (dd, J=11.0, 10.6 Hz, 1H), 6.33 (d, J=8.8 Hz, 2H), 3.78 (d, J=13.6 Hz, 1H), 3.72 (m, 1H), 3.45 (d, J=13.6 Hz, 1H), 3.20 (m, 1H), 2.99 (m, 1H), 2.51 (d, J=10.4 Hz, 1H), 2.31 (dd, J=14.4, 10.9 Hz, 1H), 2.13 (m, 1H), 1.98 (s, 3H), 1.82 (m, 2H), 1.63 (m, 2H); ¹³C NMR (100 MHz, DMSO) δ_C 174.9, 148.3, 139.9, 129.9, 129.4, 128.7, 127.6, 121.4, 117.8, 111.6, 60.3, 58.0, 54.8, 48.4, 29.2, 23.0, 12.8; MS (ES+) m/z 459 (M+H)⁺ HRMS calculated for 459.2122 $C_{28}H_{27}N_3OF_2$, found 459.2125.

Preparation of 2-(4-(3,4-difluoro-1H-pyrrol-1-yl)phenyl)-5,7-difluoro-3-methylquinolin-4(1H)-one 6a

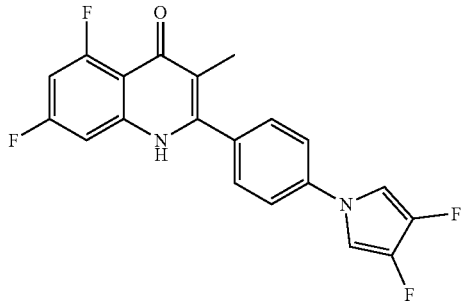 [SMILES: Cc1c(-c2ccc(-n3cc(F)c(F)c3)cc2)[nH]c2cc(F)cc(F)c2c1=O]

White solid (38 mgs, 30%). ¹H NMR (400 MHz, DMSO) $\delta_H$ 11.78 (bs, 1H), 7.83 (d, J=8.8 Hz, 2H), 7.72 (d, J=8.8 Hz, 4H), 7.14 (d, J=9.6 Hz, 1H), 7.11 (dd, J=11.0, 10.6 Hz, 1H), 1.91 (s, 3H), ¹³C NMR (100 MHz, DMSO) $\delta_C$ 175.1, 146.8, 140.3, 131.8, 130.8, 118.7, 116.9, 103.0, 12.3; MS (ES⁺) m/z 373 (M+H)⁺ HRMS calculated for 373.0964 $C_{20}H_{13}N_2OF_4$, found 373.0965.

Preparation of 6-chloro-2-(4-(3,4-difluoro-1H-pyrrol-1-yl)phenyl)-7-methoxy-3-methylquinolin-4(1H)-one 6b

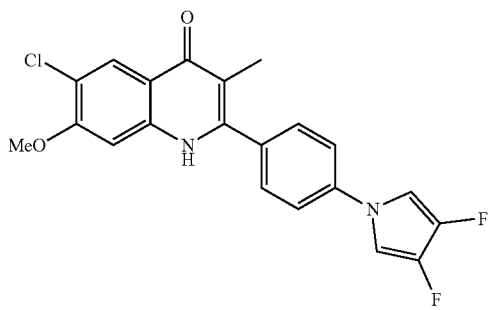 [SMILES: COc1cc2[nH]c(-c3ccc(-n4cc(F)c(F)c4)cc3)c(C)c(=O)c2cc1Cl]

White solid (0.11 g, 30%). ¹H NMR (400 MHz, DMSO) $\delta_H$ 11.75 (bs, 1H), 8.03 (s, 1H), 7.71 (d, J=8.8 Hz, 2H), 7.63 (m, 4H), 7.15 (s, 1H), 3.89 (s, 3H), 1.91 (s, 3H); ¹³C NMR (100 MHz, DMSO) $\delta_C$ 175.1, 156.3, 139.7, 138.7, 130.8, 126.0, 118.5, 114.2, 102.7, 102.5, 102.4, 56.5, 12.9; MS (ES+) m/z 401 (M+H)⁺ HRMS calculated for 401.0868 $C_{21}H_{16}N_2O_2F_2{}^{35}Cl$, found 401.0870.

Preparation of 2-(4-(3,4-difluoro-1H-pyrrol-1-yl)phenyl)-7-methoxy-3-methylquinolin-4(1H)-one 6c

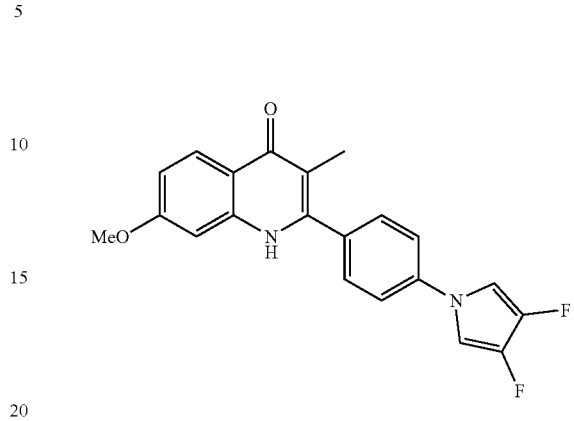

White solid (0.12 g, 32%). ¹H NMR (400 MHz, DMSO) $\delta_H$ 11.48 (bs, 1H), 8.02 (d, J=9.2 Hz, 1H), 7.75 (d, J=8.8 Hz, 2H), 7.66 (m, 4H), 7.01 (s, 1H), 6.90 (d, J=9.0 Hz, 1H), 3.82 (s, 3H), 1.90 (s, 3H); ¹³C NMR (100 MHz, DMSO) δC 176.5, 161.9, 141.8, 141.1, 140.0, 138.9, 138.7, 130.8, 127.2, 118.6, 118.0, 114.3, 113.3, 102.7, 102.5, 102.4, 99.2,. 55.7, 12.5; MS (ES⁺) m/z 367 (M+H)⁺ HRMS calculated for 367.1258 $C_{21}H_{17}N_2O_2F_2$, found 367.1257.

Preparation of 3-isopropyl-2-(1-(4-(trifluoromethoxy)benzyl)-1H-pyrazol-4-yl)quinolin-4(1H)-one (WDH-2G-6) 10a

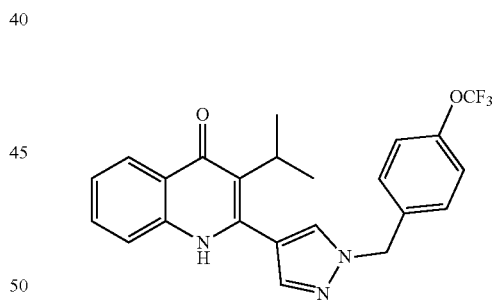

The reaction, work-up and purification procedure of title compound were followed standard cyclization procedure. The title product is given as a white solid in 63% yield. Melting point: 210-212° C. NMR: ¹H (400 MHz, DMSO) δ 11.23 (s, 1H), 8.30 (s, 1H), 8.06 (d, J=9.2 Hz, 1H), 7.78 (s, 1H), 7.60-7.46 (m, 4H), 7.41 (d, J=8.0 Hz, 2H), 7.25 (ddd, J=8.1, 6.6, 1.4 Hz, 1H), 5.49 (s, 2H), 3.01-2.88 (m, 1H), 1.32 (d, J=6.9 Hz, 6H); ¹³C NMR (101 MHz, DMSO) δ 176.71, 160.70, 148.21, 140.24, 139.68, 137.92, 137.03, 131.49, 131.20, 130.28, 125.20, 124.80, 123.73, 122.74, 121.63, 118.07, 116.02, 55.29, 29.13, 20.74. ES HRMS: m/z found 428.1566, $C_{23}H_{21}N_3O_2F_3$ requires 428.1586.

Preparation of 3-methyl-2-(1-(4-(trifluoromethoxy) phenethyl)-1H-pyrazol-4-yl)quinolin-4(1H)-one (WDH-2R-4) 10b

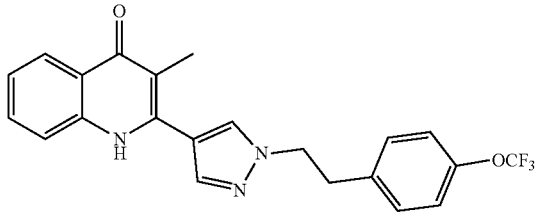 [SMILES: Cc1c(-c2cnn(CCc3ccc(OC(F)(F)F)cc3)c2)[nH]c2ccccc2c1=O]

The reaction, work-up and purification procedure of title compound were followed standard cyclization procedure. The title product is given as a white solid in 84% yield. Melting point: 210-212° C. NMR: $^1$H (400 MHz, DMSO) δ 11.25 (s, 1H), 8.12 (s, 1H), 8.07 (d, J=7.7 Hz, 1H), 7.93 (s, 1H), 7.66-7.55 (m, 2H), 7.36-7.22 (m, 5H), 4.49 (t, J=7.1 Hz, 2H), 3.22 (t, J=7.1 Hz, 2H), 1.96 (s, 3H); $^{13}$C (101 MHz, DMSO) δ 176.75, 147.38, 140.57, 139.87, 139.21, 138.06, 131.64, 131.46, 130.95, 125.30, 123.14, 122.78, 121.71, 121.36, 118.25, 115.52, 114.11, 52.76, 35.46, 12.27. ES HRMS: m/z found 414.1427, $C_{22}H_{19}N_3O_2F_3$ requires 414.1429.

Procedure for the synthesis of 7-methoxy-3-methyl-2-(6-(4-(trifluoromethoxy)phenoxy)pyridin-3-yl) quinolin-4(1H)-one (RKA259) 13a

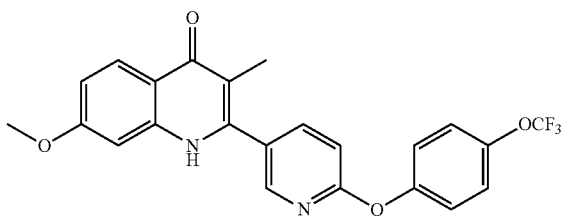 [SMILES: COc1ccc2c(=O)c(C)c(-c3ccc(Oc4ccc(OC(F)(F)F)cc4)nc3)[nH]c2c1]

The appropriately substituted oxazole (4 mmol, 1 eq) was added to a solution of ketone (4 mmol, 1 eq) and para-toluenesulfonic acid (20 mol%) in n-Butanol (10 mL). The reaction mixture was heated to 130° C. under nitrogen and stirred for 24 hours. The solvent was removed under vacuum and water (20 mL) added. The aqueous solution was extracted with EtOAc (3×20 mL), dried over MgSO$_4$ and concentrated under vacuum. The product was purified by column chromatography (eluting with 20%-80% EtOAc in n-hexane) to give the corresponding quinolone. White powder (yield 38%) m.p 296-298° C. $^1$H NMR (400 MHz, DMSO), δ$_H$ 11.47 (s, 1H, NH), 8.36 (d, 1H, J=2.0 Hz, Ar), 8.10 (dd, 1H, J=8.5 Hz, 2.5 Hz, Ar), 8.02 (g, 1H, J=8.9 Hz, Ar), 7.48 (d, 2H, J=8.7 Hz, Ar), 7.35 (d, 2H, J=8.7 Hz, Ar), 7.30 (d, 1H, J=8.5 Hz, Ar), 6.96 (d, 1H, J=2.3 Hz, Ar), 6.91 (d, 1H, J=2.4 Hz, 8.9 Hz, Ar), 3.83 (s, 3H, OCH$_3$), 1.89 (s, 3H, CH$_3$) $^{13}$C NMR (100 MHz, DMSO), δC 176.8, 163.9, 162.3, 152.5, 147.8, 141.3, 127.2, 123.9, 122.8, 120.9, 117.9, 115.3, 113.6, 111.3, 55.7, 12.3 MS (ES$^+$), [M+H]$^+$ (100), 443.1, HRMS calculated for 443.1219 $C_{23}H_{18}N_2O_4F_3$, found 443.1227.

Preparation of 2-(4-(3,3-difluoropyrrolidin-1-yl) phenyl)-5,7-difluoro-3-methylquinolin-4-yl acetate 14

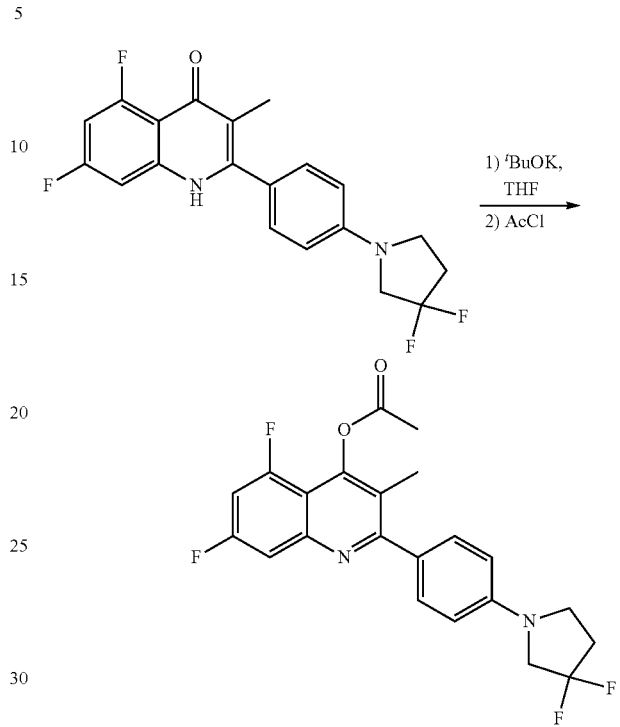

To a suspension of 2-(4-(3,3-difluoropyrrolidin-1-yl)phenyl)-5,7-difluoro-3-methylquinolin-4(1H)-one (280mg, 0.74 mmol) in THF (15 ml), $^t$BuOK (172 mg, 1.5 mmol) was added. The resulting mixture was kept stirring at room temperature for 1 hour. After that, excess acetyl chloride (0.2 ml) was added and the reaction mixture was kept stirring for 3 hours at room temperature. After that, H$_2$O (15 ml) was used to quench the reaction and Et$_2$O (50 ml) was used to dilute the mixture. Organic layer was separated from the water layer, and DCM/MeOH (1:1, 20 ml) was added to the organic layer to dissolve any precipitation. The organic solution was dried with MgSO$_4$ and concentrated in vacuo to give the crude product. The crude product we purified by flash column chromatograph eluting with 20% EtOAc in hexane to give the title product a pale yellow solid (290 mg, 94%). NMR: $^1$H (400 MHz, CDCl$_3$) δ 7.72-7.53 (m, 3H), 6.99 (dd, J=15.1, 5.7 Hz, 1H), 6.66 (d, J=8.6 Hz, 2H), 3.75 (t, J=13.2 Hz, 2H), 3.61 (t, J=7.1 Hz, 2H), 2.54 (ddd, J=21.2, 14.0, 7.3 Hz, 2H), 2.46 (s, 3H), 2.32 (s, 3H).

Preparation of 2-(4-benzylphenyl)-4-methoxy-3-methylquinoline (CK-3-23) 15

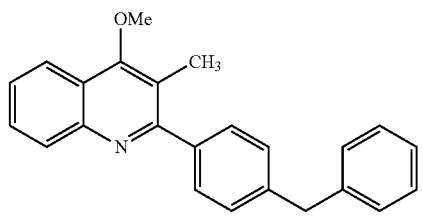

CK-3-23

A mixture of t-BuOK (0.3 mmol, 1.5 eq) and quinolone (compound 6c of J. Med. Chem., 2012, 55(5), 1844-1857, 0.2 mmol, 1.0 eq) in anhydrous THF (4 mL) was stirred for 10 min at room temperature. Methyl iodide (0.8 mmol, 4.0 eq) was added and stirring continued for 16 hr. The reaction was quenched with water and the product was extracted with EtOAc (3×10mL). The combined organic layers were dried over $MgSO_4$ and concentrated. The resulting residue was purified by flash column chromatography (eluting with 1:1 Hexane: EtOAc) to give the desired product.

Pale yellow solid (yield 88%); $^1H$ NMR (400 MHz, $CDCl_3$) δH 8.56 (d, J=8.07 Hz, 1H), 7.67 (t, J=7.03 Hz, 1H), 7.49 (d, J=8.63 Hz), 7.43-7.33 (m, 5H), 7.28-7.25 (m, 3H), 7.19 (d, J=8.03 Hz, 2H), 4.09 (s, 2H), 3.47 (s, 3H), 1.86 (s, 3H).

Full experimental details of further quinolone analogues of the present invention are detailed in WO2012069856, J. Med. Chem., 2012, 55(5), 1844-1857 and J. Med. Chem., 2012, 55(5), 1844-185, the contents of which is incorporated herein by reference.

M. tuberculosis bd Inhibitors
Heterologous Expression of Functionally Active Mtb bd
Cloning and Heterologous Expression of M. tuberculosis bd-1

The cydABCD operon was PCR amplified as a 5.9 kb fragment from M. tuberculosis genomic DNA using Pfx DNA polymerase (Invitrogen). The forward and reverse primers for this reaction were 5'-CCG GAG ATG ACA GAT GAA TGT CGT CG-3' (Fw) (SEQ ID NO. 1) and 5'-GGC GTT ACG TGC TGA TAT CGA TGA CTC AGG 3' (Rev) (SEQ ID NO. 2). The resultant fragment was subcloned to pUC19 and the sequence verified by automated DNA sequencing.

Heterologous Expression and Purification of M. tuberculosis bd-1

To facilitate heterologous expression, the pUC19-cyd-ABDC construct (pTMA) was transformed into the E. coli cytochrome $bo_3$/bd-I knockout strain ML16 (cyd cyo (Cm'). ML16 is a derivative of E.coli C43 (DE3) (genotype F-ompT gal hsdSB (rB-mB-) dcm/on λDE3)(10). Successful transformants (TML16) were cultured in selective semi-anaerobic conditions; 375 ml of Luria-Bertani broth in 500 ml flask containing 100 $\mu g.ml^{-1}$ of ampicillin and 2.5 $\mu g.ml^{-1}$ of chloramphenicol, sealed with a rubber plug with a head-space ratio of 0.5. IPTG was added at the time of culture inoculation to 1 mM final concentration. Cultures were incubated at 37° C. in a shaking incubator at 200 rpm for 19 hrs. As controls untransformed BL21 (DE3) pLysS and untransformed ML16 cells were cultured under the same conditions.

Construct pTMA was also transformed to an E. coli strain which lacks all three terminal oxidases, namely MB44 (ΔcydB::Kan ΔcyoB ΔappB ΔnuoB). Transformed MB44 cells (TMB44) were cultured anaerobically as described above using culture media supplemented with 50 mM glucose and 50 $\mu g.ml^{-1}$ kanamycin.

Cells were harvested by centrifugation at 4000×g for 10 minutes. Membrane preparations were performed as per Fisher et al. (11) and resulted in highly viscous pellets. This was collected, and resuspended with the aid of a Potter homogeniser in 2 ml of 50 mM potassium phosphate, 2 mM EDTA (pH 7.5) per litre of original culture volume. Glycerol was added to a final concentration of 10% (v/v) and the membrane suspensions stored at −80° C.

Steady-State Assays and Inhibitor Studies of Recombinant M. tuberculosis bd-I

Steady-state recombinant M. tuberculosis bd decylubiquinol oxidase activity was monitored spectrophotometrically at 283 nm in a 1 cm pathlength quartz cuvette. Assays (final volume 700 μl) were performed in an air-saturated reaction buffer consisting of 50 mM potassium phosphate (pH 7.5), 2 mM EDTA. Crude recombinant membranes were added to a final protein concentration of approximately 3 $\mu g.ml^{-1}$. The reaction was initiated by the addition of 50 μM quinol (either decylubiquinol, ubiquinol-1, or ubiquinol-2) from a 15 mM stock solution prepared as per Fisher et al. (12). Initial rates of quinol oxidation (decylubiquinol and ubiquinol-1) were fitted as Michaelis-Menten function whilst a modified ping-pong bi-bi mechanism was used for ubiquinol-2 oxidation as per Matsumoto et al., 2006 (13). All assays were performed at ambient temperature. Inhibitors were added prior to reaction initiation and DMSO maintained below 1%. $IC_{50}$ values were calculated from plots of log dose vs oxidation rate. The quinol oxidation rate was fitted to a four parameter logistic function using Origin 8.5 (OriginLab Corp., USA) and specific catalytic activity ($\mu mol.min^{-1}.mg^{-1}$) was calculated using $\varepsilon_{283}$=8.1 $mM^{-1}.cm^{-1}$.

Steady-State Kinetics

Initial steady-state kinetic assays were performed with bd-I in order to determine that a catalytically functional coenzyme had been generated. Spectrophotometrically-determined kinetic parameters for bd-I in the presence of the molecules decylubiquinol ($dQH_2$), ubiquinol-1($Q_1H_2$), or ubiquinol-2 ($Q_2H_2$) (Table 1a) revealed an order of substrate preference being established as $dQH_2 > Q_1H_2 > Q_2H_2$. $V_{max}$ values for the three substrates were similar (5-9 $\mu mol.min^{-1}.mg^{-1}$) and data generated for $dQH_2$ and $Q_1H_2$ obey simple monophasic kinetics to which a Michaelis-Menten function was applied (FIG. 2a and b). Data from the transformed triple mutant (TMB44) are shown in Table 1 and are comparable with those of TML16. However, data for $Q_2H_2$ exhibits more complex kinetics: catalytic activity initially increases as substrate concentration rises but above approx. 50 μM $Q_2H_2$ an inhibitory effect is observed and bd-I activity decreases significantly. Subsequently, these data required fitting with a modified ping-pong bi-bi function in order to determine $K_m$ and $V_{max}$ values (see Tables 1 and 2 and FIG. 1c).

TABLE 1

Steady-state kinetic parameters of Mtb bd-I activity derived from transformed double knockout TML16

|  | $K_m$ ± SEM (μM) | specific catalytic activity ± SEM ($\mu mol \cdot min^{-1} \cdot mg^{-1}$) |
|---|---|---|
| $dQH_2$ (semi-anaerobic) | 19.3 ± 1.3 | 9.0 ± 0.2 |
| $dQH_2$ (aerobic) | 21.5 ± 3.6 | 5.1 ± 0.3 |
| $Q_1H_2$ | 51.6 ± 8.9 | 5.3 ± 0.5 |
| $Q_2H_2$ | 65.2 ± 15.3 | 8.7 ± 2.5 |

TABLE 2

Steady-state kinetic parameters of Mtb bd-I activity derived from transformed triple knockout TMB44

|  | $K_m$ ± SEM (μM) | specific catalytic activity ± SEM ($\mu mol \cdot min^{-1} \cdot mg^{-1}$) |
|---|---|---|
| $dQH_2$ (semi-anaerobic) | 22.6 ± 2.1 | 6.2 ± 0.5 |
| $Q_1H_2$ | 51.8 ± 6.1 | 1.7 ± 0.3 |

Figure 1:
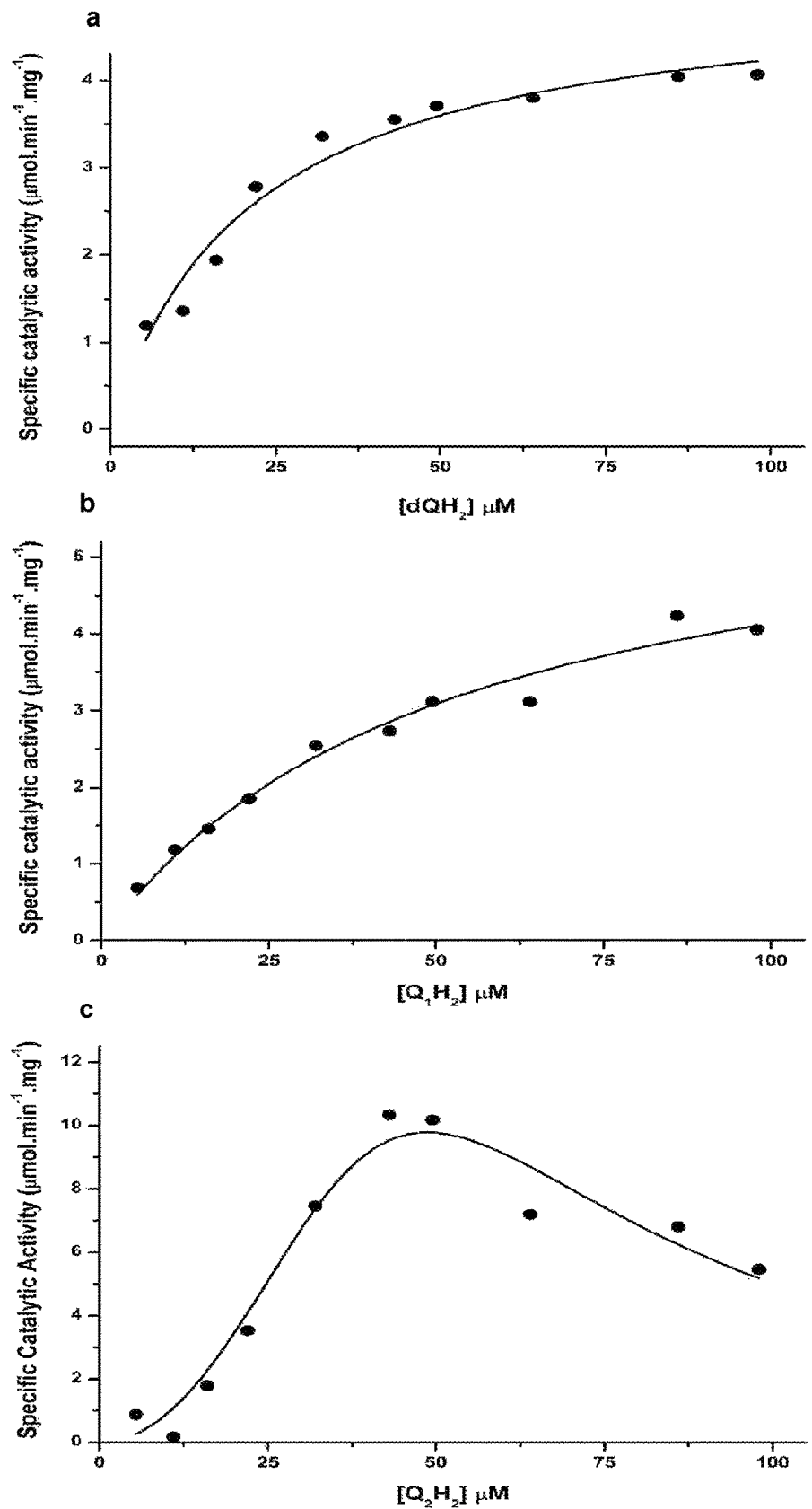
Figure 2:
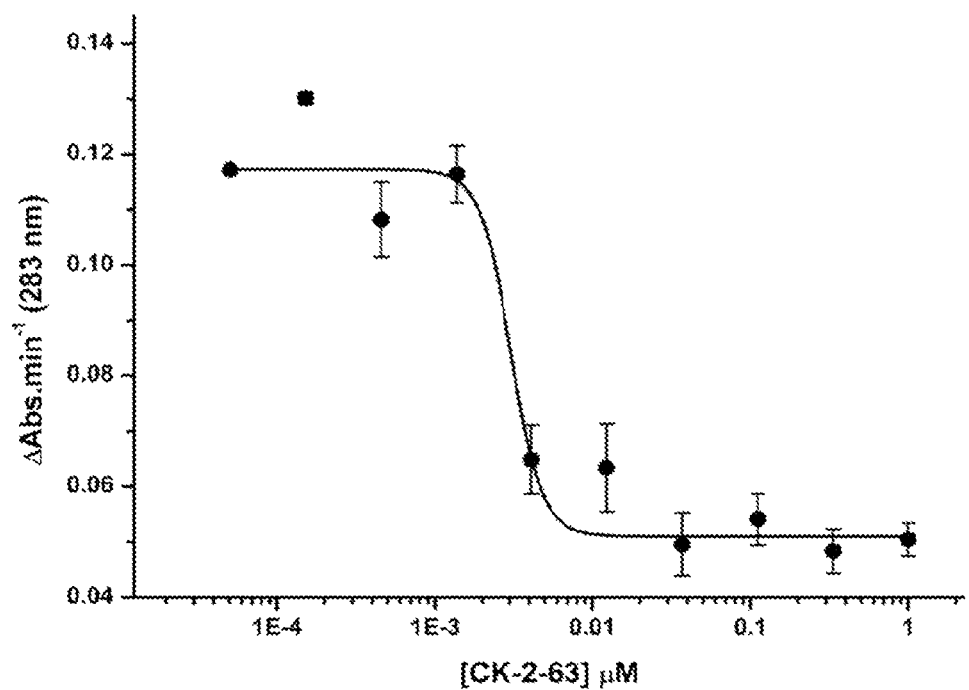
Figure 2:
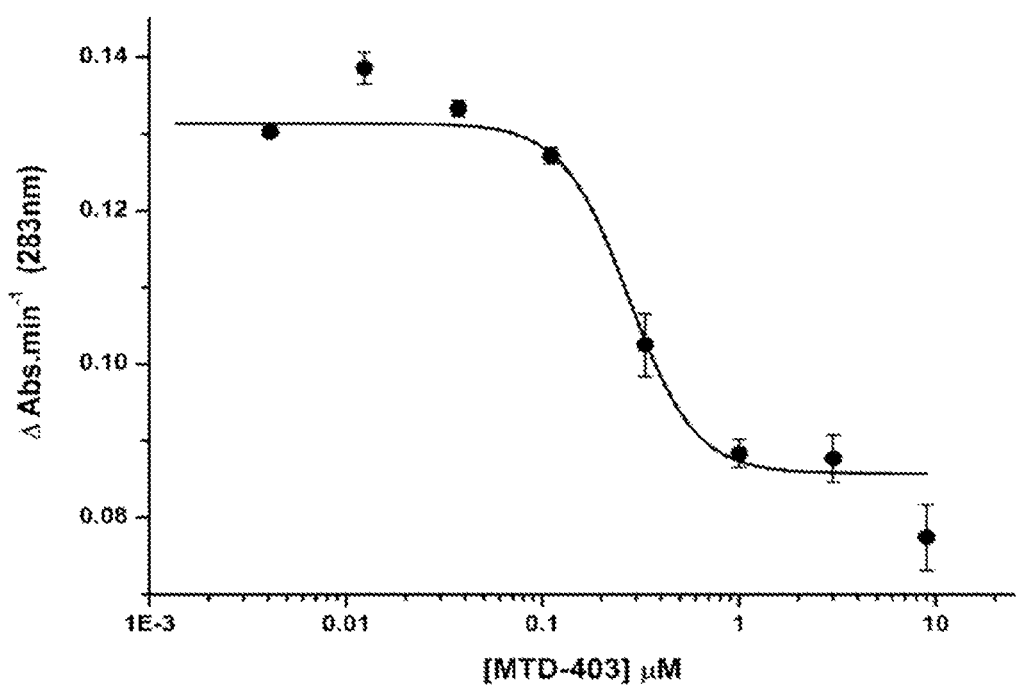
Figure 3:
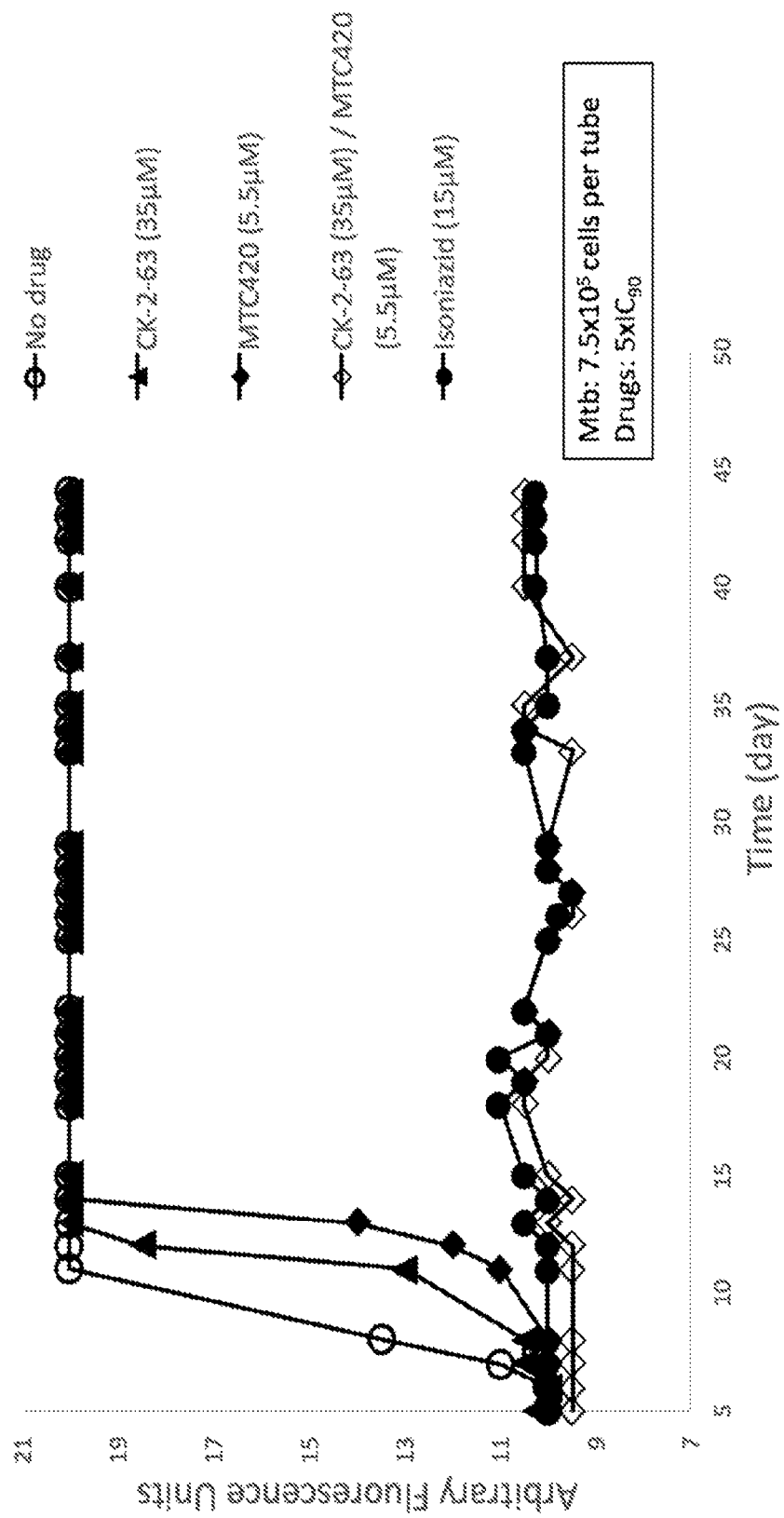

FIG. 1 shows the steady-state kinetics of quinol:Mtb bd-I activity with varying artificial quinol substrates. The steady state were measured spectrophotometrically at 283 nm and apparent $K_m$ and specific catalytic activity values were calculated.

Data for the oxidation of dQH2 and Q1H2 were fitted to a Michaelis-Menten function using rectangular hyperbola, data for the oxidation of Q2H2 were fitted to a modified ping-pong bi-bi function (Origin 8.5 software).

The apparent $K_m$ and specific catalytic activity values calculated for the oxidation of decylubiquinol (dQH2) were calculated as $21.52\pm3.57$ μM and $5.1\pm0.29$ μmol.min$^{-1}$.mg$^{-1}$, respectively.

The apparent $K_m$ and specific catalytic activity values for the oxidation of ubiquinol-1 (Q1H2) were calculated to be $51.55\pm8.9$ μM and $5.26\pm0.52$ μmol.min$^{-1}$.mg$^{-1}$, respectively.

The apparent $K_m$ and specific catalytic activity values for the oxidation of ubiquinol-2 (Q2H2) were calculated to be $65.21\pm15.31$ μM and $8.65\pm2.5$ μmol.min$^{-1}$.mg$^{-1}$, respectively.

Mtb cyt bd Inhibitors

Identification of Mtb cyt bd Inhibitors

Table 3 shows the activities of inhibitors against Mtb cyt bd-I were significantly more potent than observed for HDQ and KCN, with IC$_{50}$ values ranging from 0.003 to 70.3 μM. Compounds were also initially screened for *M. tuberculosis* H37Rv growth inhibition activity at a fixed 5 μM concentration (Table 3).

TABLE 3

Inhibitor activity data against *M. tuberculosis* cytochrome bd-I and *M. tuberculosis* growth inhibition

| Compound | Structure | ClogP | bd-I, IC$_{50}$ ± SEM (μM) | Growth of *M. tuberculosis* H37Rv (aerobic) at 5 μM of [compounds] (%)* |
|---|---|---|---|---|
| CK-3-22 (T1) | [quinolin-4(1H)-one with pyridyl-O-phenyl-OCF$_3$ substituent] | 5.49 | 0.14 ± 0.02 | 19.5 |
| CK-3-14 (T1) | [quinolin-4(1H)-one with pyridyl-O-(4-fluorophenyl) substituent] | 4.12 | 10.6 ± 6.58 | 100 |
| RKA-259 (T1) | [7-methoxy-quinolin-4(1H)-one with pyridyl-O-phenyl-OCF$_3$ substituent] | 5.36 | 3.6 ± 1.67 | 12.6 |
| RKA-307 (T2) | [quinolin-4(1H)-one with 4-(piperidin-1-yl)phenyl substituent] | 4.06 | 0.44 ± 0.08 | 1.8 |

TABLE 3-continued

Inhibitor activity data against *M. tuberculosis* cytochrome bd-I and *M. tuberculosis* growth inhibition

| Compound | Structure | ClogP | bd-I, IC$_{50}$ ± SEM (μM) | Growth of *M. tuberculosis* H37Rv (aerobic) at 5 μM of [compounds] (%)* |
|---|---|---|---|---|
| RKA-310 (T2) | 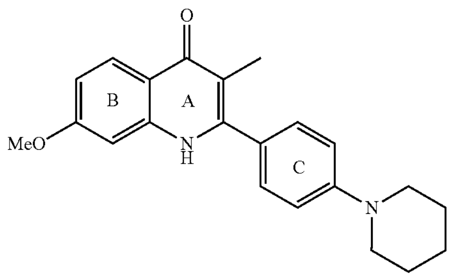 | 3.96 | 1.4 ± 0.17 | No growth |
| MTD-403 (T2) | 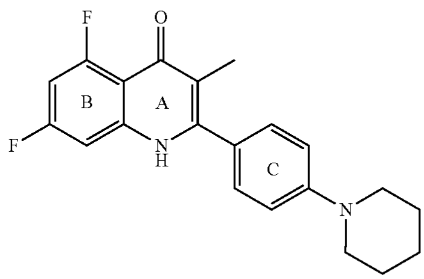 | 4.38 | 0.27 ± 0.06 | No growth |
| CK-2-88 (T3) | 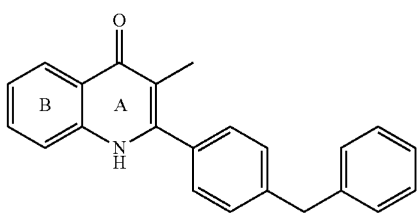 | 5.14 | 0.02 ± 0.01 | 90.5 |
| CK-3-23 (T3) | 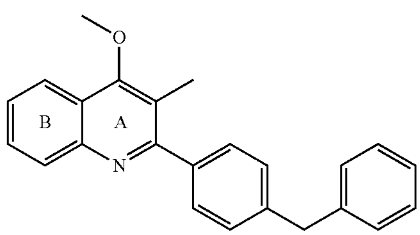 | 6.67 | 3.6 ± 0.57 | 6.6 |
| CK-2-63 (T3) | 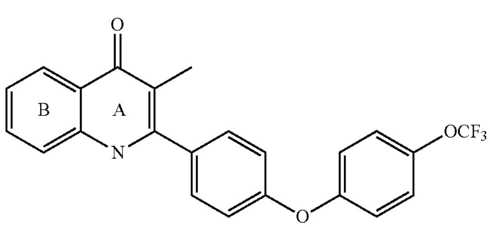 | 6.11 | $3 \times 10^{-3} \pm 1 \times 10^{-4}$ | 37.8 |
| PG-203 (T3) | 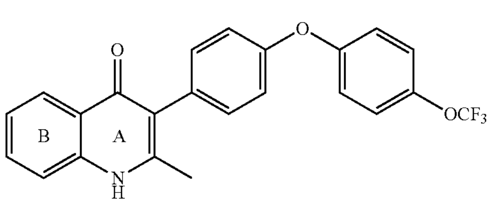 | 5.23 | 0.07 ± 0.02 | 100 |

TABLE 3-continued

Inhibitor activity data against *M. tuberculosis* cytochrome bd-I and *M. tuberculosis* growth inhibition

| Compound | Structure | ClogP | bd-I, IC$_{50}$ ± SEM (μM) | Growth of *M. tuberculosis* H37Rv (aerobic) at 5 μM of [compounds] (%)* |
|---|---|---|---|---|
| RKA-70 (T3) | 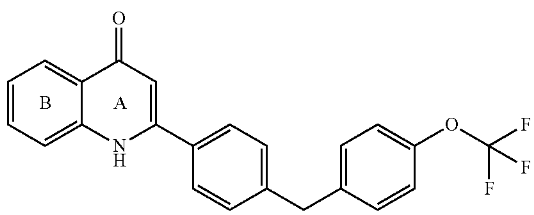 | 6.32 | 0.75 ± 0.36 | 100 |
| RKA-73 (T3) | 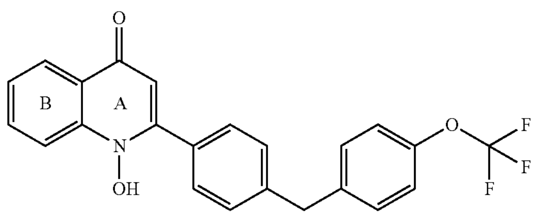 | 6.18 | 0.31 ± 0.06 | 100 |
| LT-9 (T3) | 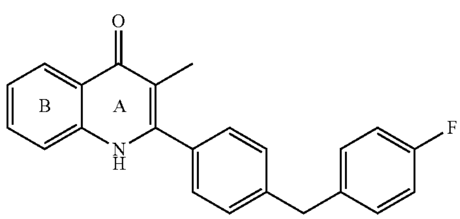 | 5.30 | 0.1 ± 0.02 | 34.7 |
| GN-1710 (T3) | 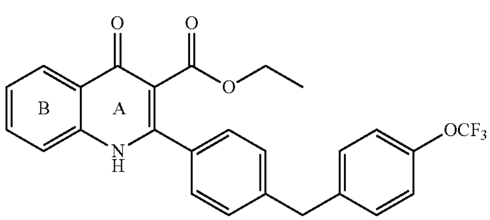 | 6.34 | 0.25 ± 0.09 | 100 |
| PG-128 (T4) | 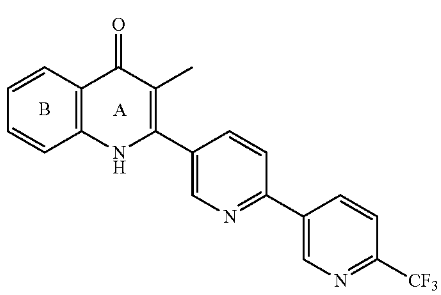 | 3.82 | 4.47 ± 0.86 | 95.6 |

TABLE 3-continued

Inhibitor activity data against *M. tuberculosis* cytochrome bd-I and *M. tuberculosis* growth inhibition

| Compound | Structure | ClogP | bd-I, IC$_{50}$ ± SEM (μM) | Growth of *M. tuberculosis* H37Rv (aerobic) at 5 μM of [compounds] (%)* |
|---|---|---|---|---|
| SL-2-25 (T4) | 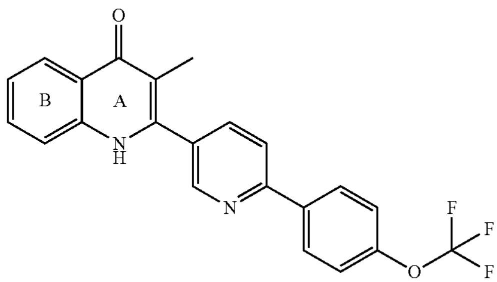 | 5.33 | 0.29 ± 0.07 | 88.9 |
| WDH-1U-10 (T4) | 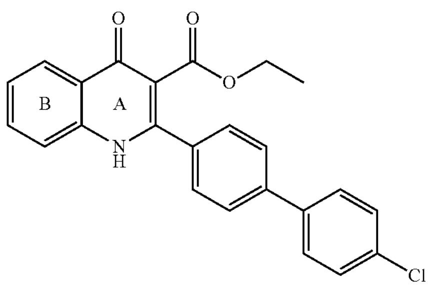 | 4.95 | 0.012 ± 1 × 10$^{-3}$ | 82.2 |
| WDH-1W-5 (T5) | | 4.29 | 15

| Molecule Name | Structure | Mw | inhibition @ 1 uM (% of cntls) | IC$_{50}$ (μM) |
|---|---|---|---|---|
| WDH-1V-10 | 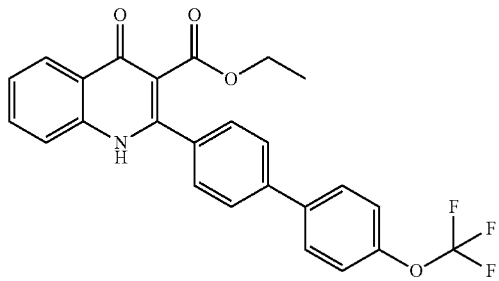 [SMILES: CCOC(=O)c1c(-c2ccc(-c3ccc(OC(F)(F)F)cc3)cc2)[nH]c2ccccc2c1=O] | 403.862 | 79.4 | n.d. |
| WDH-1V-9 | 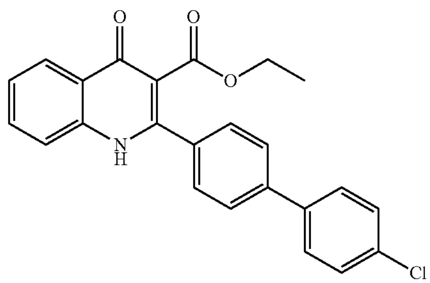 [SMILES: CCOC(=O)c1c(-c2ccc(-c3ccc(Cl)cc3)cc2)[nH]c2ccccc2c1=O] | 453.417 | 87.5 | n.d |
| WDH-2G-6 | 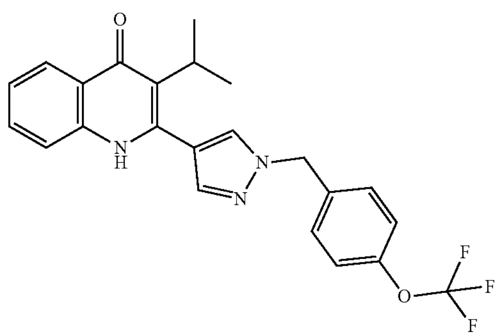 [SMILES: CC(C)c1c(-c2cnn(Cc3ccc(OC(F)(F)F)cc3)c2)[nH]c2ccccc2c1=O] | 427.427 | 81.6 | 0.082 |
| WDH-2R-4 | 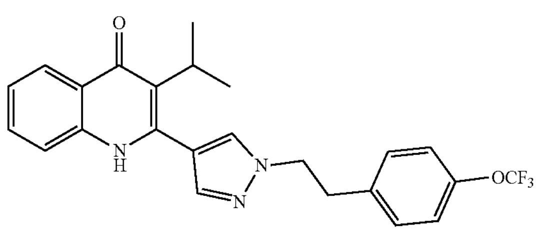 [SMILES: CC(C)c1c(-c2cnn(CCc3ccc(OC(F)(F)F)cc3)c2)[nH]c2ccccc2c1=O] | 413.4 | 56.2 | 0.38 |
| SL-2-34 | 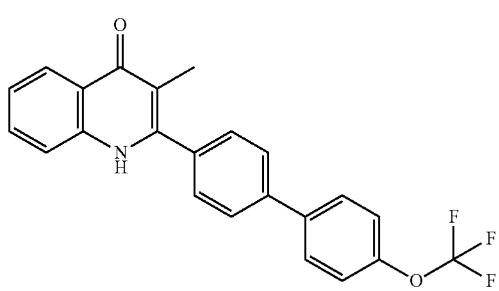 [SMILES: Cc1c(-c2ccc(-c3ccc(OC(F)(F)F)cc3)cc2)[nH]c2ccccc2c1=O] | 395.381 | 90.3 | n.d. |

| Molecule Name | Structure | Mw | inhibition @ 1 uM (% of cntls) | IC$_{50}$ (μM) |
|---|---|---|---|---|
| SL-2-36 | 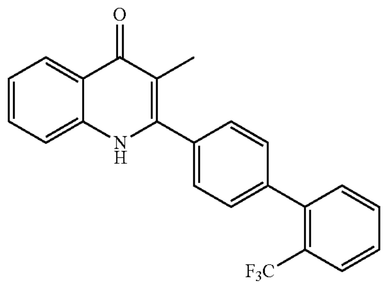 [SMILES: Cc1c(-c2ccc(-c3ccccc3C(F)(F)F)cc2)[nH]c2ccccc2c1=O] | 379.382 | 90.5 | n.d |
| SL-3-3 | 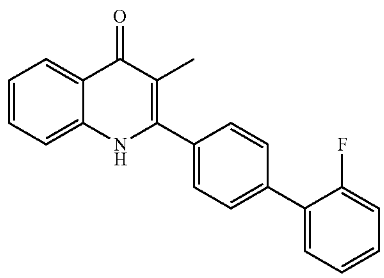 [SMILES: Cc1c(-c2ccc(-c3ccccc3F)cc2)[nH]c2ccccc2c1=O] | 329.374 | 62.2 | n.d |
| RKA 142 | 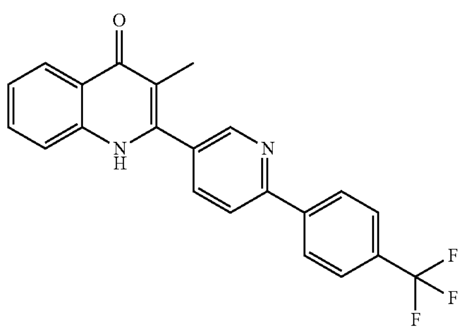 [SMILES: Cc1c(-c2ccc(-c3ccc(C(F)(F)F)cc3)nc2)[nH]c2ccccc2c1=O] | 411.38 | >50 | 2.02 |
| PG105 | 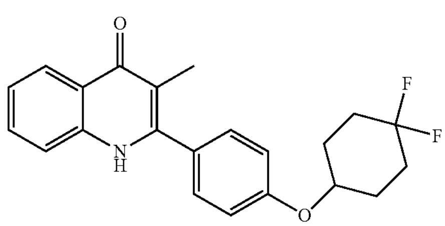 [SMILES: Cc1c(-c2ccc(OC3CCC(F)(F)CC3)cc2)[nH]c2ccccc2c1=O] | 369.412 | 71.5 | n.d |
| PG201 | 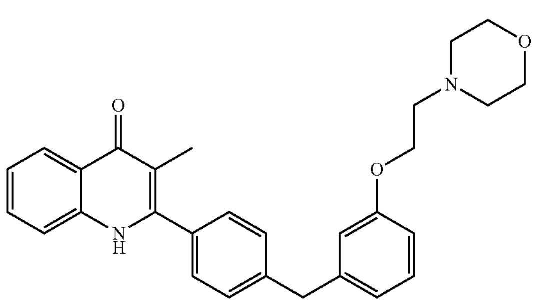 [SMILES: Cc1c(-c2ccc(Cc3cccc(OCCN4CCOCC4)c3)cc2)[nH]c2ccccc2c1=O] | 454.57 | 68.7 | n.d |

-continued

| Molecule Name | Structure | Mw | inhibition @ 1 uM (% of cntls) | IC$_{50}$ (μM) |
|---|---|---|---|---|
| PG208 | 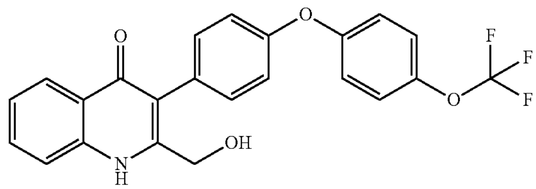 [SMILES: O=c1c(-c2ccc(Oc3ccc(OC(F)(F)F)cc3)cc2)c(CO)[nH]c2ccccc12] | 427.379 | 66.7 | n.d |
| SCR-45-01D | 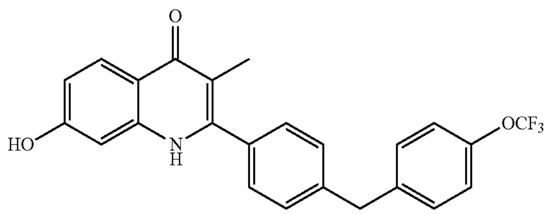 [SMILES: Cc1c(-c2ccc(Cc3ccc(OC(F)(F)F)cc3)cc2)[nH]c2cc(O)ccc2c1=O] | 425.407 | 81.5 | n.d |
| SCR-06-03D | 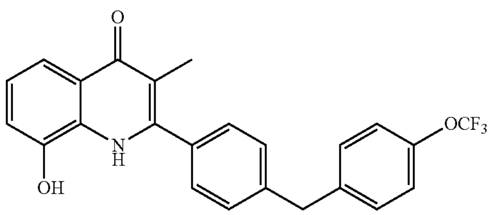 [SMILES: Cc1c(-c2ccc(Cc3ccc(OC(F)(F)F)cc3)cc2)[nH]c2c(O)cccc2c1=O] | 425.407 | 73.1 | n.d |
| SCR-04-04 | 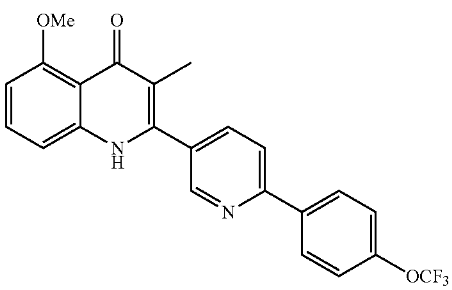 [SMILES: COc1cccc2[nH]c(-c3ccc(-c4ccc(OC(F)(F)F)cc4)nc3)c(C)c(=O)c12] | 426.395 | 65.4 | n.d |
| SCR-05-03 | 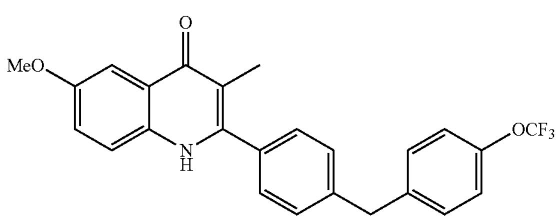 [SMILES: COc1ccc2[nH]c(-c3ccc(Cc4ccc(OC(F)(F)F)cc4)cc3)c(C)c(=O)c2c1] | 439.434 | 60.9 | n.d |
| CK-2-58 | 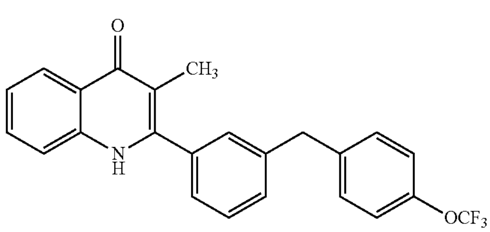 [SMILES: Cc1c(-c2cccc(Cc3ccc(OC(F)(F)F)cc3)c2)[nH]c2ccccc2c1=O] | 409.448 | 82.3 | n.d |
| CK-2-67 | 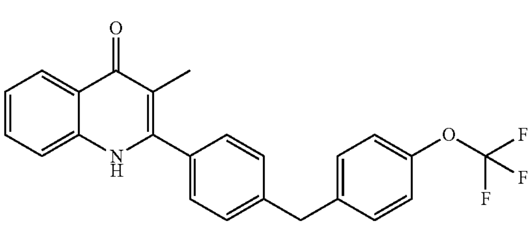 [SMILES: Cc1c(-c2ccc(Cc3ccc(OC(F)(F)F)cc3)cc2)[nH]c2ccccc2c1=O] | 409.408 | 81.5 | n.d |

| Molecule Name | Structure | Mw | inhibition @ 1 uM (% of cntls) | IC$_{50}$ (μM) |
|---|---|---|---|---|
| CK-2-96 | 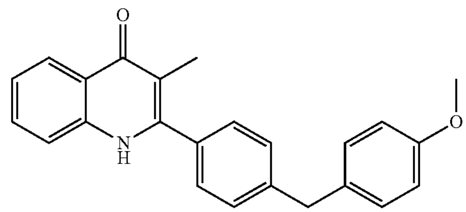 [SMILES: COc1ccc(Cc2ccc(-c3[nH]c4ccccc4c(=O)c3C)cc2)cc1] | 355.437 | 85.7 | n.d |
| CK-2-88 | 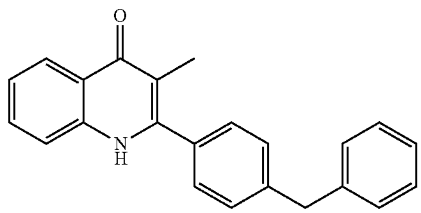 [SMILES: Cc1c(-c2ccc(Cc3ccccc3)cc2)[nH]c2ccccc2c1=O] | 325.411 | 87.5 | n.d |
| CK-3-68 | 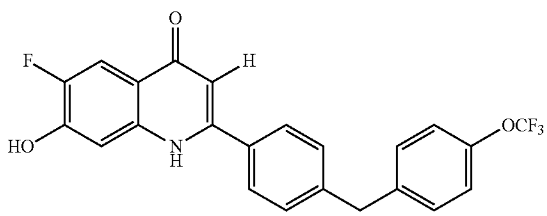 [SMILES: O=c1cc(-c2ccc(Cc3ccc(OC(F)(F)F)cc3)cc2)[nH]c2cc(O)c(F)cc12] | 429.371 | 71.7 | n.d |
| CK-4-2 | 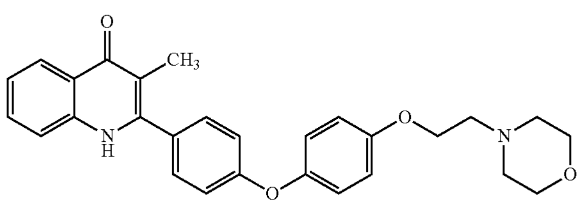 [SMILES: Cc1c(-c2ccc(Oc3ccc(OCCN4CCOCC4)cc3)cc2)[nH]c2ccccc2c1=O] | 454.57 | 63.6 | n.d |
| CK-4-15 | 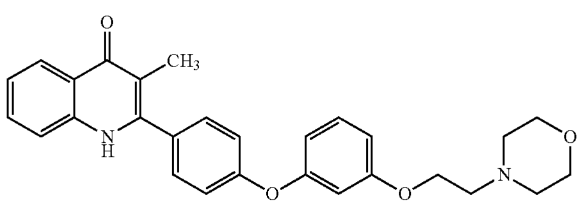 [SMILES: Cc1c(-c2ccc(Oc3cccc(OCCN4CCOCC4)c3)cc2)[nH]c2ccccc2c1=O] | 456.542 | 66.6 | n.d |
| CK-3-22 | 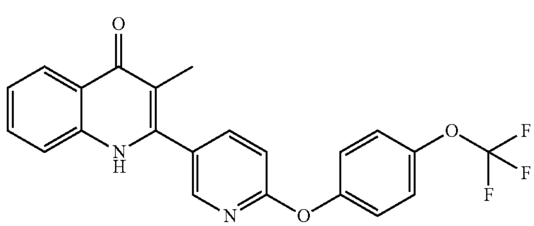 [SMILES: Cc1c(-c2ccc(Oc3ccc(OC(F)(F)F)cc3)nc2)[nH]c2ccccc2c1=O] | 381.354 | 62.8 | n.d |

Toxicity Studies

Activities of Mtb bd inhibitors against bovine cytochrome $bc_1$ were determined spectrophotometrically as a function of cytochrome c reduction as per Biagini et al., (14) using Keilin-Hartree particles.(15) Inhibitors were added prior to reaction initiation with 50 μM decylubiquinol and IC$_{50}$ values determined as per enzyme inhibition studies. Cellular toxicities were determined as previously described (7).

Several compounds were found to have nanomolar activities against bovine cytochrome $bc_1$. For example, the IC$_{50}$ of CK-2-63 in this assay was determined as 0.30 μM whilst many other compounds exhibited IC$_{50}$s below 1 μM. In vitro counter screening of compounds against the immortalised HepG2 cell line however, showed no appreciable toxicity below 50-100 μM (Table 4).

TABLE 4

Activities of Mtb cyt bd inhibitors against bovine cytochrome bc1 and the human cell counter screen (HepG2).

| Compound | $bc_1$ (µM) | HepG2 (µM) |
|---|---|---|
| CK-2-63 | 0.30 | 84.6 |
| RKA-70 | 0.31 | >50 |
| LT-9 | 0.19 | >50 |
| SL-2-25 | 0.89 | >50 |
| MTD-403 | 0.7 | >100 |
| CK-2-88 | 0.34 | >100 |

Combinatory Inhibition

Next, the combinatory effects on Mtb growth inhibition achieved through the combined administration of an Mtb cyt bd inhibitor (CK-2-63) and an Mtb cyt bcc inhibitor was investigated.

The Mtb cyt bcc inhibitors selected for combined administration with the Mtb cyt bd inhibitor CK-2-63 were as follows:

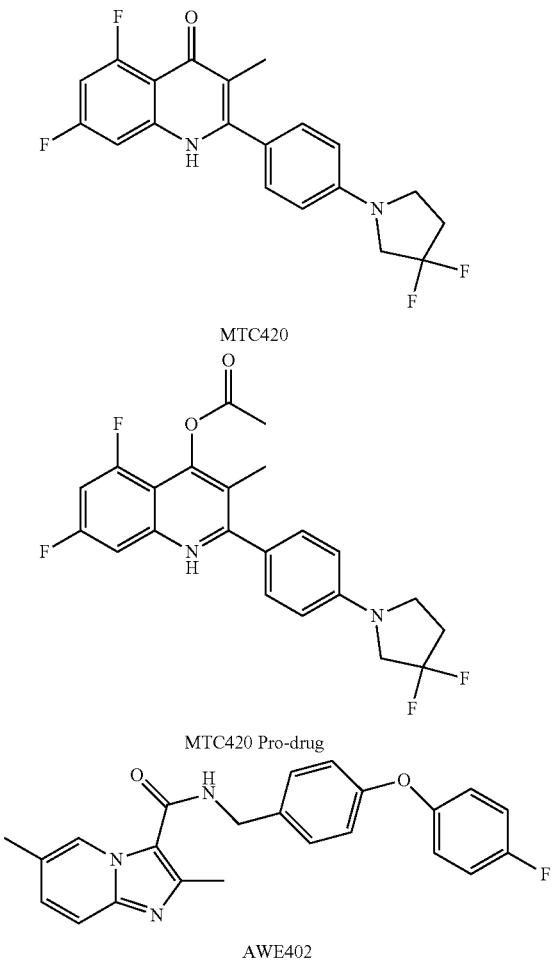

MTC420

MTC420 Pro-drug

AWE402

The Mtb cyt bcc inhibitor AWE402, shown above, is structurally related to the Mycobacterium cyt bcc inhibitor Q203 described by Pethe et al. (28).

From analysis of the growth and inhibition profiles for both the Mtb cyt bcc inhibitor MTC420 and the Mtb cyt bd inhibitor CK-2-62 are shown in Table 5 it was postulated whether the combination of the two inhibitors (MTC420 and CK-2-63), which target different pathways of the same respiratory chain, would give a slight increase in Mtb growth inhibition.

TABLE 5

The growth and enzyme inhibition profiles for MTC420 and CK-2-63

| Compound | In vitro (replicating) growth inhibition Mtb ($IC_{50}$ (μM)) | In vitro ndh enzyme inhibition ($IC_{50}$ (μM)) | In vitro Cyt bd enzyme inhibition ($IC_{50}$ (μM)) |
|---|---|---|---|
| MTC420 | 0.52 | >1 | 5.58 |
| CK263 | 3.28 | 0.25 | $3.0 \times 10^{-3}$ |

MIGIT—Growth Inhibition Assays.

Mycobacteria Growth Indicator Tube (MGIT™) containing 0.5 mL Middlebrook™ OADC enrichment solution and 50 μL test compound ($5 > IC_{90}$ (90% inhibitory concentration) as determined from modified MABA assays) were inoculated with a mid-log phase aerobic Mycobacterium tuberculosis (Mtb) H37Rv culture approximately $1.3 \times 10^4$ cfu.ml/1(in Middlebrook™ 7H9 media (ADC enrichment)). A drug free negative control including DMSO (final concentration 1%) was also included in order to monitor normal Mtb growth along with a positive control of isoniasid ($5 \times IC_{90}$). Tubes were wrapped in foil to protect from light and incubated at 37° C. Readings were taken daily on a BACTEC MicroMGIT™ reader. A fluorescence reading of 13 and above (culture positive tube) is considered a drug fail.

Alamar Blue Assay

For drug susceptibility assays, aerobic cultures of Mtb H37Rv were grown to mid-log phase at 37° C. in 10 mL growth media [Middlebrook 7H9 broth supplemented with 10% albumin-dextrose-catalase solution (Becton Dickinson), 0.2% (v/v) glycerol and 0.05% (v/v) Tween 80].

Mtb drug sensitivities were determined using a microplate Alamar blue assay (MABA) described by Hartkoorn et al. [17]. Measurements of well absorbance at 570 and 600 nm recorded using an Opsys MR plate reader were utilized to calculate IC50 values for the inhibitors. For anaerobic cultures, plates were sealed within GasPak EZ pouches containing an indicator to ensure anaerobic conditions were maintained. The plates were subsequently incubated anaerobically at 37° C. for 7 days before being moved to an aerobic environment for a further 7 days. The IC50 values were calculated as described for aerobic cultures.

Drug competition assays (isobole analyses) were performed using the method of Berenbaum [18]. The IC50 values for each compound to be tested were determined by the MABA technique described above Mtb was grown in MGITs (Mycobacteria Growth Indicator Tubes) in the presence of CK263 or MTC420, alone and in combination. In this growth proliferation inhibition assay it was shown that in the presence of both drugs independently, Mtb growth reached positivity at 11-13 days, consistent with 5-day alamar blue readouts.

However surprisingly, when MTC420 and CK263 where combined, a dramatic increase in Mtb kill was observed, with no outgrowth being observed for up to 50 days (FIG. 3). This experiment was repeated 3 times. Isobole analysis of CK-2-63 and MTC420, based on the 5-day alamar blue readout, was indicative of a synergistic interaction (FIG. 4).

Interestingly, addition of CK-2-63 in combination with imidazo pyridine inhibitors (e.g. AWE402) targeting Mtb cyt b identified by Abrahams et al., (8), also resulted in a significant increase in time to positivity (FIG. 5).

Table 6 tabulates both the time to positivity of Mtb grown in MGITs and the concentrations used for all of the tested inhibitiors, either alone or in combination.

TABLE 6

The time to positivity of Mtb grown in MGITs containing the drug compounds alone or in combination.

| Compound | Concentration (µM) 5x $IC_{90}$ | Time to Positivity (Day) |
| --- | --- | --- |
| Drug Free Control | — | 11 |
| INH | 15 | No effect at 74 days |
| Rifampicin | 0.5 | No effect at 74 days |
| CK-2-63 | 35 | 12 |
| MTC 420 | 5.5 | 18 |
| AWE 402 | 0.025 | 15 |
| CK-2-63/AWE 402 | 35/0.025 | 27 |
| CK-2-63/MTC 420 | 35/5.5 | 57 |
| AWE 402/MTC 420 | 0.025/5.5 | 18 |
| CK-2-63/MTC 420/AWE 402 | 35/5.5/0.025 | No effect at 74 days |

Figure 4:
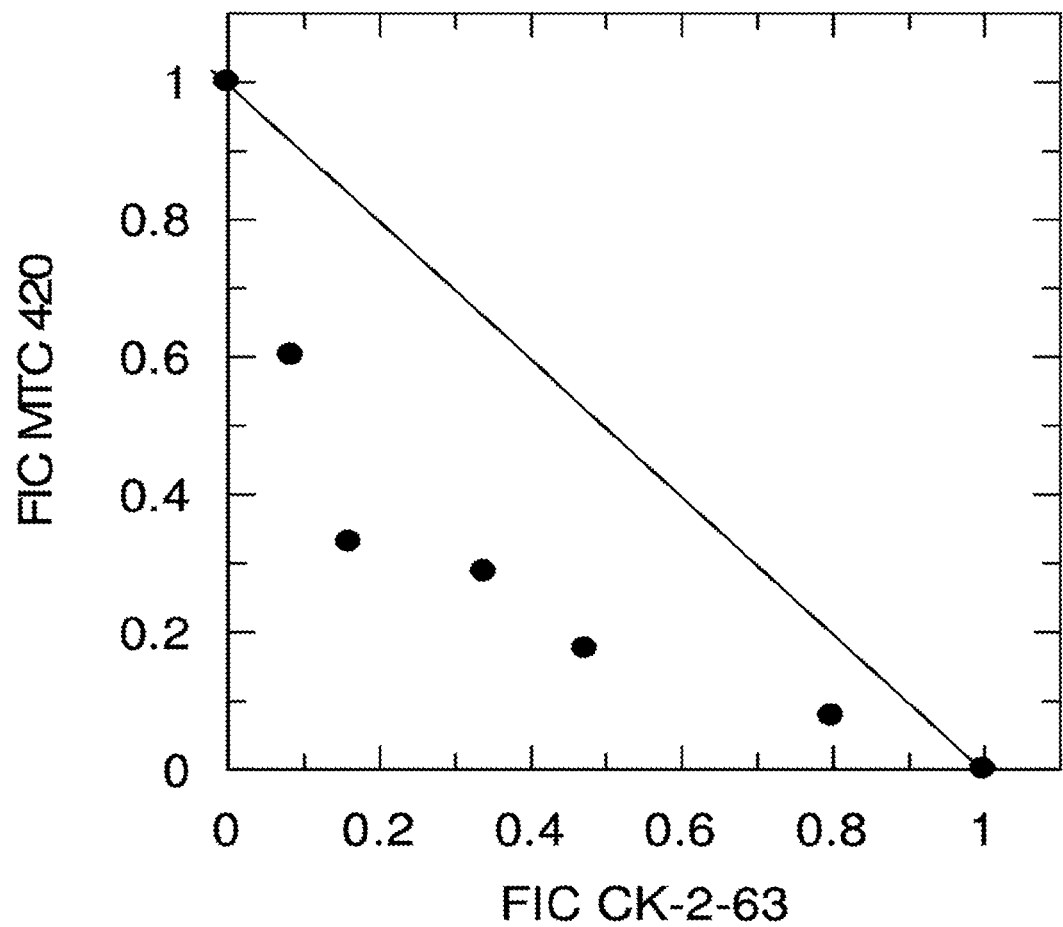
Figure 5:
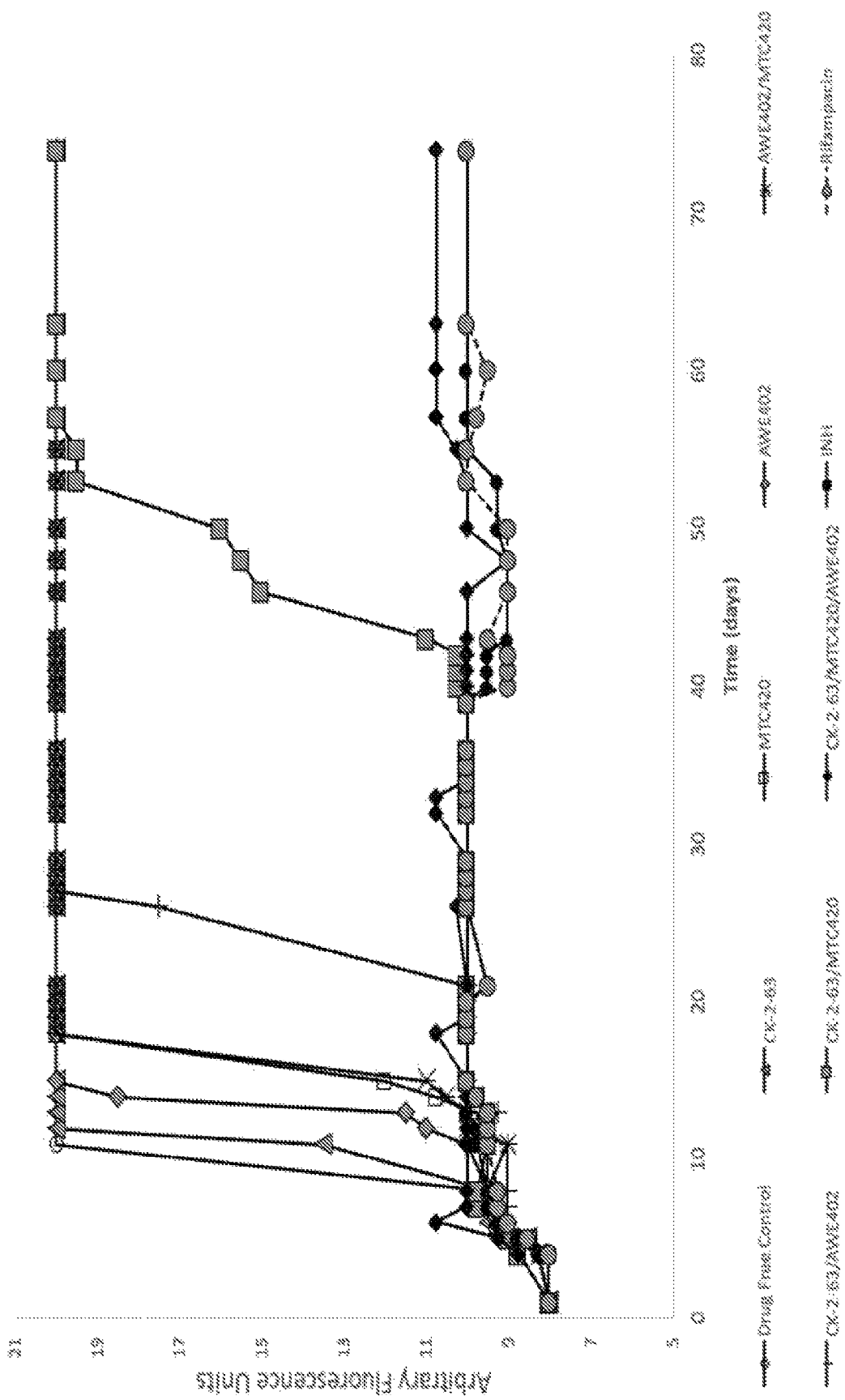

Of note from the data presented in FIG. 4 and Table 6, is that cyt bcc inhibitors AWE402 and MTC420 alone or together do not increase the time to positivity. However, when either compound is combined with the cyt bd inhibitor CK-2-63, dramatic prolongation of the time to positivity is achieved.

Studies Into Combined Treatments Using a cyt bd Inhibitor and an ATPsynthase Inhibitor The combinatory effects of administering a cyt bd inhibitor, CK-2-63, in combination with an ATP synthase inhibitor, benoquline (TMC207), were next investigated.

Figure 7:
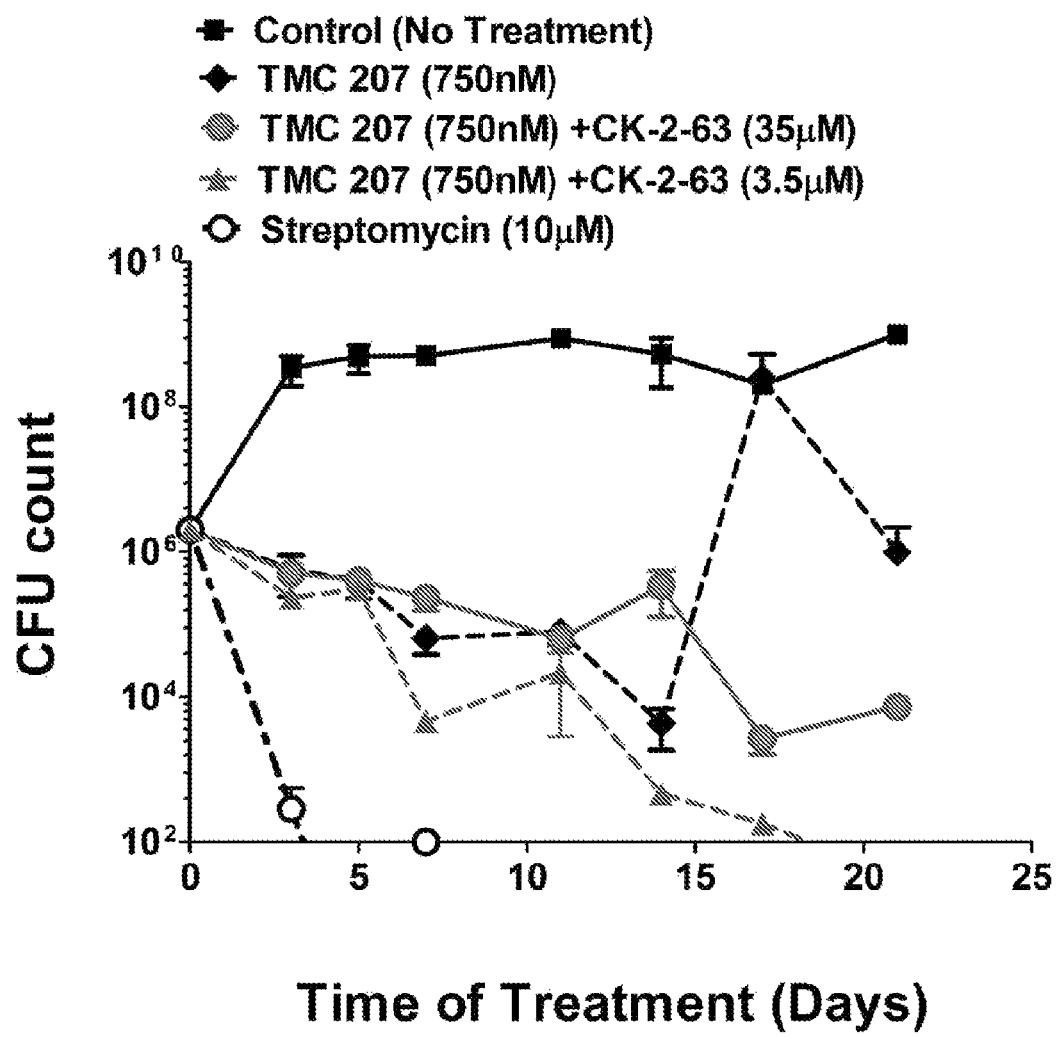

Time kill experiments performed with combinations of CK-2-63 and bedaquiline demonstrated marked enhancement of activity. Critically CK-2-63 showed a dramatic enhancement of bedaquiline activity at low concentrations of bedaquiline, even when this drug either had no observed effect or bactriostatic effect. The dramatic enhancement of bedaquiline activity is seen at both high (35 µM, FIG. 6) and low (3.5 µM, FIG. 7) concentrations of CK-2-63.

Figure 8:
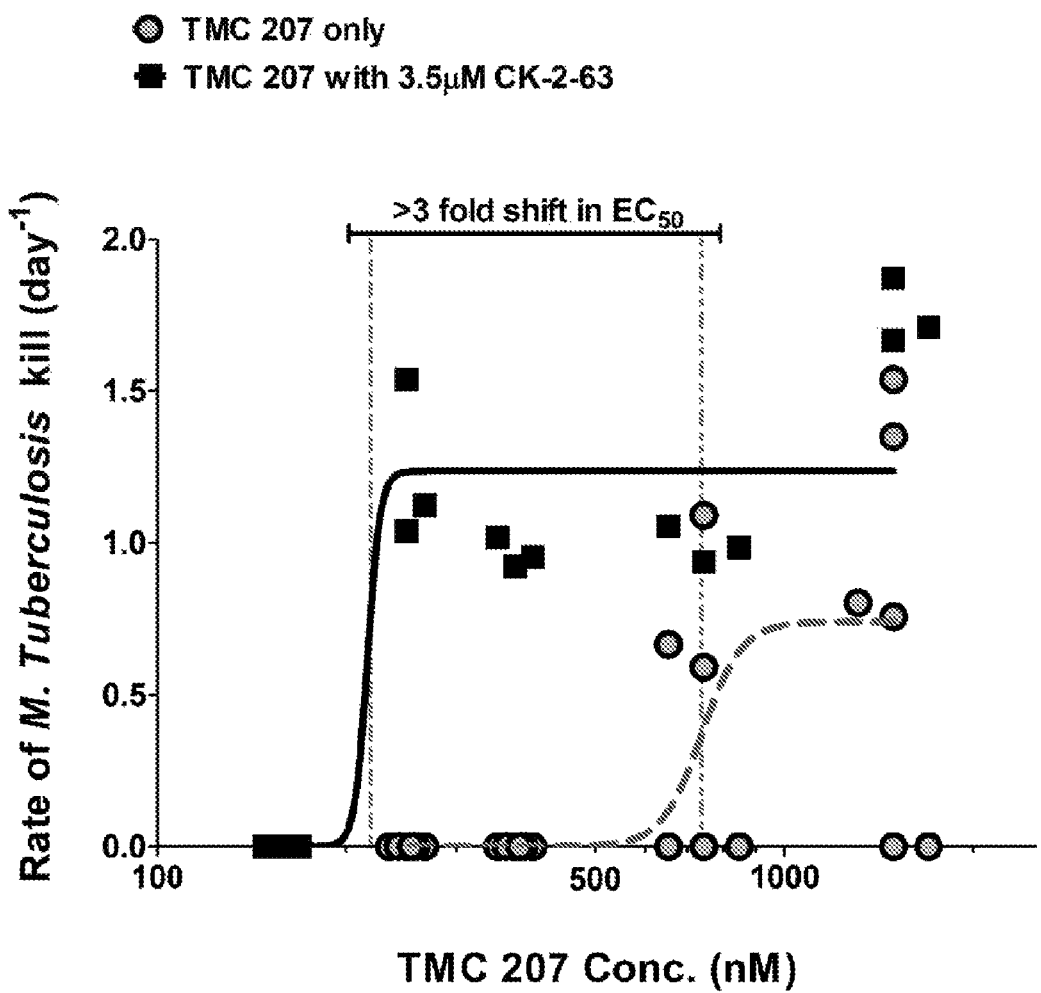

In repeat studies, addition of CK-2-63 is shown to result in >3 fold shift to reach the maximal killing rate of bedaquiline (FIG. 8). These data have major clinical implications indicating that combinatory approaches would result in improved clinical efficacy at reduced levels of bedaquiline.

Targeting of cyt bcc, cyt bd and ATPsynthase with Multiple Inhibitors

Figure 9:
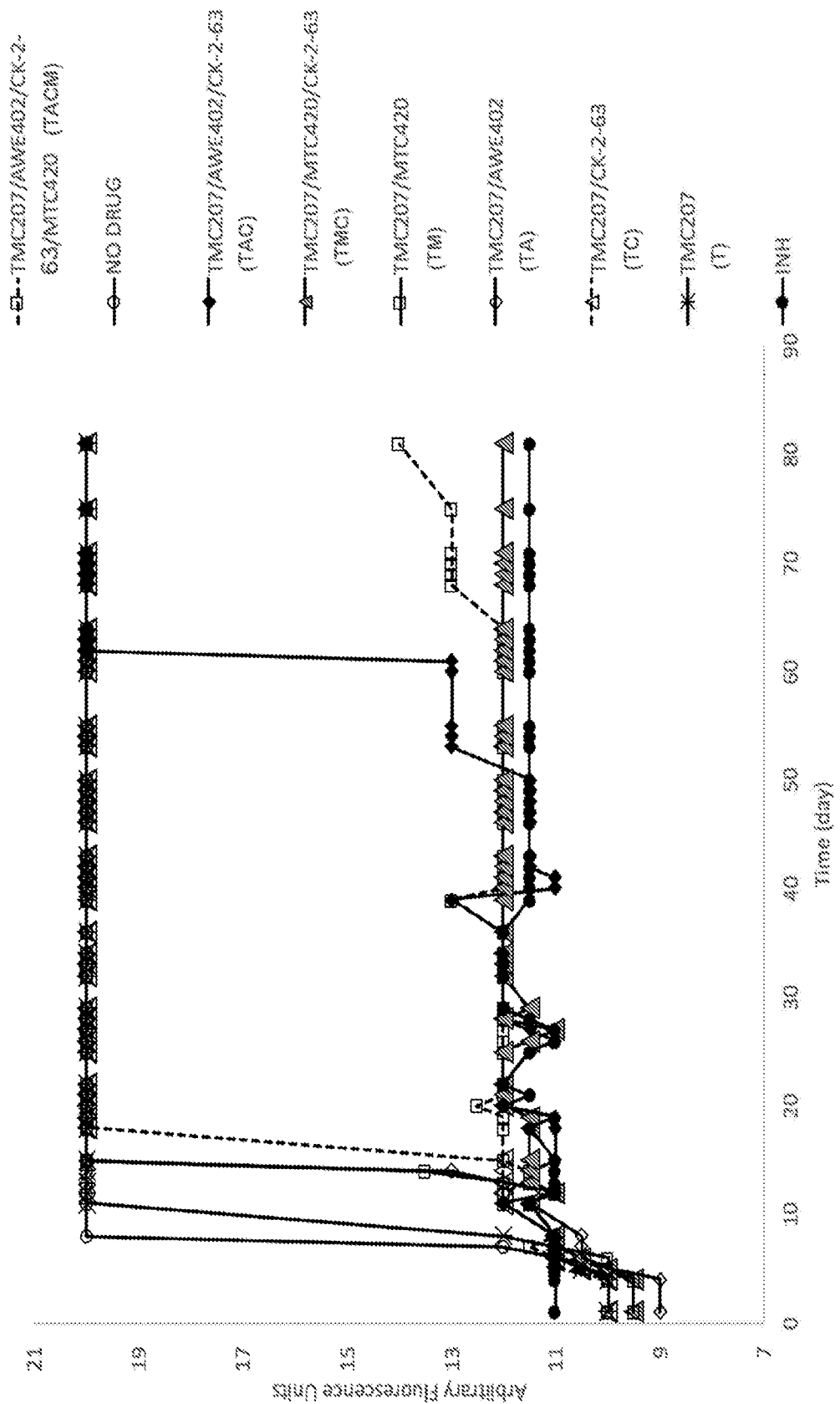

FIG. 9 shows the time to positivity profiles of Mtb grown in MGITs containing cyt bcc, cyt bd and ATPsynthase inhibitors alone and in combination with one another.

FIG. 9 also shows that administering multiple cyt bcc, cyt bd and ATPsynthase inhibitors improves efficacy relative to mono and dual administration.

Table 7 tabulates both the time to positivity of Mtb grown in MGITs and the concentrations used for all of the tested inhibitiors, either alone or in combination.

TABLE 7

Time to positivity of Mtb grown in MGITs containing drugs alone or in multiple combination taken from data presented in FIG. 9.

| FIG. 9 Reference Code | Compound | Concentration (µM) 5x $IC_{90}$ | Time to Positivity (Day) |
| --- | --- | --- | --- |
|  | Drug Free Control | — | 8 |
|  | INH | 15 | No effect at 80 days |
| TACM | TMC 207/AWE402/CK-2-63/MTC420 | 0.25/0.025/35/5.5 | No effect at 80 days |
| TAC | TMC 207/AWE402/CK-2-63 | 0.25/0.025/35 | 62 |
| TCM | TMC 207/CK-2-63/MTC420 | 0.25/35/5.5 | No effect at 80 days |

TABLE 7-continued

Time to positivity of Mtb grown in MGITs containing drugs alone or in multiple combination taken from data presented in FIG. 9.

| FIG. 9 Reference Code | Compound | Concentration (µM) 5x $IC_{90}$ | Time to Positivity (Day) |
| --- | --- | --- | --- |
| TM | TMC 207/MTC420 | 0.25/5.5 | 15 |
| TA | TMC 207/AWE402 | 0.25/0.025 | 15 |
| TC | TMC 207/CK-2-63 | 0.25/35 | 18 |
| T | TMC 207 | 0.25 | 12 |

Further Studies Towards Combined Administration of an Mtb cyt bd Inhibitor and an Mtb cyt bcc Inhibitor Lansoprazole has recently been described as an inhibitor of Mtb cyt $bc_1$ (also known as cyt bcc) complex[19].

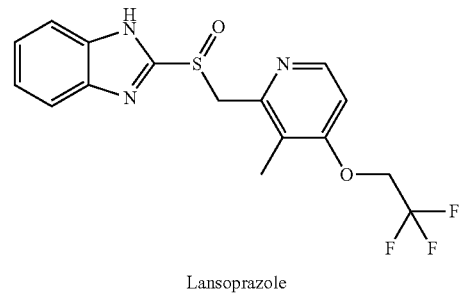 [SMILES: Cc1c(OCC(F)(F)F)ccnc1CS(=O)c1nc2ccccc2[nH]1]

Lansoprazole

Using the in vitro Mtb "Time to positivity"(TtP)-based assay, drug-free control results in an Mtb TtP of 10 days. In direct comparison, addition of lansoprazole sulfide alone (at a final concentration of 26.5 µM) results in a TtP of 13 days whilst CK-2-63 (35 µM, final concentration) addition results in a TtP of 13 days. Addition of a combination of lansoprazole sulphide and CK-2-63 suppresses Mtb growth and TtP is not reached after 45 days, comparable to the positive control using INH (15 µM, final concentration).

Further Studies Towards Targeting of cyt bcc, cyt bd and ATPsynthase with Multiple Inhibitors Additional in vitro combination experiments were performed with the identified Mtb cytochrome bd inhibitor WDG-2G-6. Using the described MIGIT in vitro assay. Time to positivity of Mtb was determined for WDG-2G-6 (final concentration 3 µM) alone or in combination with the cyt bcc (also known as $bc_1$) inhibitors MTC420 (5.5 µM), AWE 402 (0.025 pM) and lansoprazole sulphide (26.5 µM) and in combination with the Mtb ATPsynthase inhibitor TMC207 (also known as bedaquiline at final concentration of 250 nM). In all combinations, WDG-2G-6 was shown to significantly enhance the time-to-positivity compared with inhibitors used alone (Table 8). These data further support the finding that Mtb cyt bd inhibition significantly enhances the antitubercular effect of inhibitors targeting respiratory components bcc and Mtb ATPsynthase.

TABLE 8

Time to positivity of Mtb grown in MGITs containing drugs alone or in combination with WDH-2G-6

| Treatment | Time to positivity (days) |
| --- | --- |
| Media control | 10 |
| WDH-2G-6 | 10 |
| MTC420 | 13 |

TABLE 8-continued

Time to positivity of Mtb grown in MGITs containing
drugs alone or in combination with WDH-2G-6

| Treatment | Time to positivity (days) |
|---|---|
| AWE 402 | 13 |
| Lansoprazole sulphide | 13 |
| TMC 207 | 13 |
| WDH-2G-6 + MTC420 | 17 |
| WDH-2G-6 + AWE402 | 17 |
| WDH-2G-6 + Lansoprazole sulphide | 20 |
| WDH-2G-6 + TMC207 | 17 |

While specific embodiments of the invention have been described herein for the purpose of reference and illustration, various modifications will be apparent to a person skilled in the art without departing from the scope of the invention as defined by the appended claims.

REFERENCES

1. Weinstein E A, et al. (2005) Inhibitors of type II NADH: menaquinone oxidoreductase represent a class of antitubercular drugs. *Proc Natl Acad Sci USA* 102(12):4548-4553.
2. Koul A, et al. (2007) Diarylquinolines target subunit c of mycobacterial ATP synthase. *Nat Chem Biol* 3(6):323-324.
3. Haagsma A C, et al. (2009) Selectivity of TMC207 towards mycobacterial ATP synthase compared with that towards the eukaryotic homologue. *Antimicrob Agents Chemother* 53(3): 1290-1292.
4. Koul A, et al. (2008) Diarylquinolines are bactericidal for dormant mycobacteria as a result of disturbed ATP homeostasis. *J Biol Chem* 283(37):25273-25280.
5. Rao S P, Alonso S, Rand L, Dick T, & Pethe K (2008) The protonmotive force is required for maintaining ATP homeostasis and viability of hypoxic, nonreplicating Mycobacterium tuberculosis. *Proc Natl Acad Sci USA* 105(33):11945-11950.
6. Diacon A H, et al. (2009) The diarylquinoline TMC207 for multidrug-resistant tuberculosis. *N Engl J Med* 360(23):2397-2405.
7. Warman A J, et al. (2013) Antitubercular pharmacodynamics of phenothiazines. *J Antimicrob Chemother* 68(4): 869-880.
8. Wu Y (2002) How might qinghaosu (artemisinin) and related compounds kill the intraerythrocytic malaria parasite? A chemist's view. *Accounts of chemical research* 35(5):255-259.
9. Vitaliy B. Borisov, Robert B Gennis, James Hemp, Michael I. Verkhovsky (2011), The cytochrome bd respiratory oxygen reductases, *Biochimica et Biophysica Acta (BBA)—Bioenergetics*, 1807(11):1398-1413.
10. Miroux B & Walker J E (1996) Over-production of proteins in *Escherichia coli:* Mutant hosts that allow synthesis of some membrane proteins and globular proteins at high levels. *Journal of Molecular Biology* 260(3):289-298
11. Fisher N, Warman A J, Ward S A, & Biagini G A (2009) Chapter 17 Type II NADH: quinone oxidoreductases of Plasmodium falciparum and *Mycobacterium tuberculosis* kinetic and high-throughput assays. *Methods in enzymology* 456:303-320.
12. Fisher N, et al. (2012) Cytochrome b mutation Y268S conferring atovaquone resistance phenotype in malaria parasite results in reduced parasite $bc_1$ catalytic turnover and protein expression. *J. Biol. Chem.* 287(13):9731-9741.
13. Matsumoto Y, et al. (2006) Kinetic mechanism of quinol oxidation by cytochrome bd studied with ubiquinone-2 analogs. *Journal of Biochemistry* 139(4):779-788.
14. Biagini G A, et al. (2008) Acridinediones: selective and potent inhibitors of the malaria parasite mitochondrial bc1 complex. *Molecular pharmacology* 73(5):1347-1355.
15. Kuboyama M, Yong F C, & King T E (1972) Studies on cytochrome oxidase. *J. Biol. Chem.* 247(20):6375-6383.
16. Sirturo datasheet and safety information, https://www.sirturo.com/.
17. Hartkoorn R C, Chandler B, Owen A, et al. Differential drug susceptibility of intracellular and extracellular tuberculosis, and the impact of P-glycoprotein, *Tuberculosis*, 2007; 87(3): 248-55.
18. Berenbaum M C. A method for testing for synergy with any number of agents. *The Journal of Infectious Diseases,* 1978; 137(2): 122-30
19. Rybniker, J. et al. (2015) Lansoprazole is an antituberculous prodrug targeting cytochrome bc1. *Nature communications* 6, 7659, doi:10.1038/ncomms8659.

The invention claimed is:

1. A combination therapeutic product comprising one or more respiratory electron transport chain inhibitors, or a pharmaceutically acceptable salt thereof, and a cytochrome bd inhibitor, or a pharmaceutically acceptable salt thereof;
   wherein the one or more respiratory electron transport chain inhibitors or a pharmaceutically acceptable salt thereof, is selected from lansoprazole, bedaquiline (TMC207), MTC420, AWE402, Q203, Isoniazid and phenothiazines; and
   the cytochrome bd inhibitor, or a pharmaceutically acceptable salt thereof, is selected from
   3-Methyl-2-(6-(4-(trifluoromethoxy)phenoxy)pyridin-3-yl)quinolin-4(1H)-one (CK-3-22);
   2-(6-(4-Fluorophenoxy)pyridin-3-yl)-3-methylquinolin-4(1H)-one (CK-3-14);
   7-Methoxy-3-methyl-2-(6-(4-(trifluoromethoxy)phenoxy)pyridin-3-yl)quinolin-4(1H)-one (RKA-259);
   3-Methyl-2-(4-(piperidin-1-yl)phenyl)quinolin-4(1H)-one (RKA-307);
   7-Methoxy-3-methyl-2-(6-(4-(trifluoromethoxy)phenoxy)pyridin-3-yl)quinolin-4(1H)-one (RKA-310);
   5,7-Difluoro-3-methyl-2-(4-(piperidin-1-yl)phenyl)quinolin-4(1H)-one (MTD-403);
   2-(4-Benzylphenyl)-3-methylquinolin-4(1H)-one (CK-2-88);
   2-(4-Benzylphenyl)-4-methoxy-3-methylquinoline (CK-3-23);
   3-Methyl-2-(4-(4-(trifluoromethoxy)phenoxy)phenyl)quinolin-4(1H)-one (CK-2-63);
   2-Methyl-3-(4-(4-(trifluoromethoxy)phenoxy)phenyl)quinolin-4(1H)-one (PG-203)
   2-(4-(4-(Trifluoromethoxy)benzyl)phenyl)quinolin-4(1H)-one (RKA-70);
   1-Hydroxy-2-(4-(4-(trifluoromethoxy)benzyl)phenyl)quinolin-4(1H)-one (RKA-73);
   2-(4-(4-Fluorobenzyl)phenyl)-3-methylquinolin-4(1H)-one (LT-9);
   Ethyl 4-oxo-2-(4-(4-(trifluoromethoxy)benzyl)phenyl)-1,4-dihydroquinoline-3-carboxylate (GN-171);
   3-Methyl-2-(6'-(trifluoromethyl)[2,3'-bipyridin]-5-yl)quinolin-4(1H)-one (PG-128);
   3-Methyl-2-(6-(4-(trifluoromethoxy)phenyl)pyridin-3-yl)quinolin-4(1H)-one (SL-2-25);
   Ethyl 2-(4'-chloro-[1,1'-biphenyl]-4-yl)-4-oxo-1,4-dihydroquinoline-3-carboxylate (WDH -1U-10);
   2-(1-(4-(Trifluoromethoxy)benzyl)-1H-pyrazol-4-yl)quinolin-4(1H)-one (WDH-1W-5);
   3-Methyl-2-(1-(4-(trifluoromethoxy)benzyl)-1H-pyrazol-4-yl)quinolin-4(1H)-one (WDH -2A-9).
   Ethyl 4-oxo-2-(4'-(trifluoromethoxy)-[1,1'-biphenyl]-4-yl)-1,4-dihydroquinoline-3-carboxylate (WDH-1V-10);
   Ethyl 2-(4'-chloro-[1,1'-biphenyl]-4-yl)-4-oxo-1,4-dihydroquinoline-3-carboxylate (WDH -1V-9);
   3-Isopropyl-2-(1-(4-(trifluoromethoxy)benzyl)-1H-pyrazol-4-yl)quinolin-4(1H)-one (WDH-2G-6);
   3-Methyl-2-(1-(4-(trifluoromethoxy)phenethyl)-1H-pyrazol-4-yl)quinolin-4(1H)-one (WDH-2R-4);
   3-Methyl-2-(4'-(trifluoromethoxy)-[1,1'-biphenyl]-4-yl)quinolin-4(1H)-one (SL-2-34);
   3-Methyl-2-(2'-(trifluoromethyl)[1,1'-biphenyl]-4-yl)quinolin-4(1H)-one (SL-2-36);
   2-(2'-Fluoro-[1,1'-biphenyl]-4-yl)-3-methylquinolin-4(1H)-one (SL-3-3);
   3-Methyl-2-(6-(4-(trifluoromethyl)phenyl)pyridin-3-yl)quinolin-4(1H)-one (RKA 142);
   2-(4-((4,4-Difluorocyclohexyl)oxy)phenyl)-3-methylquinolin-4(1H)-one (PG105);
   3-Methyl-2-(4-(3-(2-morpholinoethoxy)benzyl)phenyl)quinolin-4(1H)-one (PG201);
   2-(Hydroxymethyl)-3-(4-(4-(trifluoromethoxy)phenoxy)phenyl)quinolin-4(1H)-one (PG208);
   7-Hydroxy-3-methyl-2-(4-(4-(trifluoromethoxy)benzyl)phenyl)quinolin-4(1H)-one (SCR -05-01D);
   8-Hydroxy-3-methyl-2-(4-(4-(trifluoromethoxy)benzyl)phenyl)quinolin-4(1H)-one (SCR -06-03D);
   5-Methoxy-3-methyl-2-(6-(4-(trifluoromethoxy)phenyl)pyridin-3-yl)quinolin-4(1H)-one (SCR-04-04);
   6-Methoxy-3-methyl-2-(4-(4-(trifluoromethoxy)benzyl)phenyl)quinolin-4(1H)-one (SCR -05-03);
   3-Methyl-2-(3-(4-(trifluoromethoxy)benzyl)phenyl)quinolin-4(1H)-one (CK-2-58);
   3-Methyl-2-(4-(4-(trifluoromethoxy)benzyl)phenyl)quinolin-4(1H)-one (CK-2-67);
   2-(4-(4-Methoxybenzyl)phenyl)-3-methylquinolin-4(1H)-one (CK-2-96);
   2-(4-Benzylphenyl)-3-methylquinolin-4(1H)-one (CK-2-88);
   6-Fluoro-7-hydroxy-2-(4-(4-(trifluoromethoxy)benzyl)phenyl)quinolin-4(1H)-one (CK-3-68);
   3-Methyl-2-(4-(4-(2-morpholinoethoxy)benzyl)phenyl)quinolin-4(1H)-one (CK-4-2);
   3-Methyl-2-(4-(3-(2-morpholinoethoxy)phenoxy)phenyl)quinolin-4(1H)-one (CK-4-15); and
   3-Methyl-2-(6-(4-(trifluoromethoxy)phenoxy)pyridin-3-yl)quinolin-4(1H)-one (CK-3-22).

2. The combination therapeutic product according to claim 1, wherein the one or more respiratory electron transport chain inhibitors or a pharmaceutically acceptable salt thereof, is selected from bedaquiline (TMC207), MTC420, AWE402, Q203, Isoniazid or phenothiazines.

3. The combination therapeutic product according to claim 1, wherein the one or more respiratory electron transport chain inhibitors or a pharmaceutically acceptable salt thereof, is selected from bedaquiline (TMC207), MTC420 or AWE402.

4. The combination therapeutic product according to claim 1, wherein the one or more respiratory electron transport chain inhibitors or a pharmaceutically acceptable salt thereof is selected from bedaquiline (TMC207) or Q203.

5. The combination therapeutic product according to claim 1, wherein the one or more respiratory electron transport chain inhibitors or a pharmaceutically acceptable salt thereof is bedaquiline (TMC207).

6. The combination therapeutic product according to claim 1, wherein the cytochrome bd inhibitor, or a pharmaceutically acceptable salt thereof, is 3-Methyl-2-(4-(4-(trifluoromethoxy)phenoxy)phenyl)quinolin-4(1H)-one (CK-2-63).

7. The combination therapeutic product according to claim 1, wherein the one or more respiratory electron transport chain inhibitors or a pharmaceutically acceptable salt thereof is selected from bedaquiline (TMC207) or Q203; and the cytochrome bd inhibitor, or a pharmaceutically acceptable salt thereof, is 3-Methyl-2-(4-(4-(trifluoromethoxy)phenoxy)phenyl)quinolin-4(1H)-one (CK-2-63).

8. The combination therapeutic product according to claim 1, wherein the respiratory electron transport chain inhibitors or a pharmaceutically acceptable salt thereof, is bedaquiline (TMC207); and the cytochrome bd inhibitor, or a pharmaceutically acceptable salt thereof, is 3-Methyl-2-(4-(4-(trifluoromethoxy)phenoxy)phenyl)quinolin-4(1H)-one (CK -2-63).

9. A method of treating a mycobacterial infection comprising:
   administering an effective amount of the combination product according to claim 1 to a patient.

10. The method according to claim 9, wherein the combination product is administered simultaneously, sequentially, or separately to the patient.

11. The method according to claim 9, wherein the mycobacterial infection is tuberculosis.

12. The method according to claim 9, wherein the mycobacterial infection is multidrug resistant tuberculosis.

* * * * *